(12) United States Patent
Doi et al.

(10) Patent No.: US 8,951,760 B2
(45) Date of Patent: Feb. 10, 2015

(54) METHOD FOR PRODUCING AN L-AMINO ACID

(71) Applicant: Ajinomoto Co., Inc., Tokyo (JP)

(72) Inventors: Hidetaka Doi, Kanagawa (JP); Yasushi Hoshino, Kanagawa (JP); Yuri Masumitsu, Kanagawa (JP); Yoshihiro Usuda, Kanagawa (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 13/912,313

(22) Filed: Jun. 7, 2013

(65) Prior Publication Data

US 2013/0260425 A1    Oct. 3, 2013

Related U.S. Application Data

(63) Continuation of application No. PCT/JP2011/078380, filed on Dec. 8, 2011.

(30) Foreign Application Priority Data

Dec. 10, 2010  (JP) .................................. 2010-276062

(51) Int. Cl.
| | | |
|---|---|---|
| *C12P 13/08* | (2006.01) | |
| *C12P 13/04* | (2006.01) | |
| *C07K 14/245* | (2006.01) | |
| *C12N 1/20* | (2006.01) | |

(Continued)

(52) U.S. Cl.
CPC .................. *C12P 13/08* (2013.01); *C12P 13/04* (2013.01); *C07K 14/245* (2013.01); *C12N 1/20* (2013.01); *C12N 1/38* (2013.01); *C12N 15/746* (2013.01)
USPC .......................................... 435/115; 435/106

(58) Field of Classification Search
None
See application file for complete search history.

(56) References Cited

U.S. PATENT DOCUMENTS

| | | | |
|---|---|---|---|
| 7,494,801 B2* | 2/2009 | Yazaki et al. ............. | 435/252.33 |
| 7,695,946 B2 | 4/2010 | Usuda et al. | |
| 7,696,315 B2 | 4/2010 | Usuda et al. | |

(Continued)

FOREIGN PATENT DOCUMENTS

| | | |
|---|---|---|
| JP | 2008-167746 | 7/2008 |
| JP | 2009-118740 | 6/2009 |

(Continued)

OTHER PUBLICATIONS

Guo et al., "Protein tolerance to random amino acid change", Proceedings of the National Academy of Sciences USA, vol. 101, No. 5, pp. 9205-9210, 2004.*

(Continued)

*Primary Examiner* — Rebecca Prouty
*Assistant Examiner* — Richard Ekstrom
(74) *Attorney, Agent, or Firm* — Shelly Guest Cermak; Cermak Nakajima & McGowan LLP

(57) ABSTRACT

A method for producing an L-amino acid includes culturing a bacterium which belongs to the family Enterobacteriaceae and has an L-amino acid-producing ability in a medium containing a carbon source selected from a fatty acid and an alcohol, and collecting the L-amino acid from the medium. A bacterium which has been subjected to a modification including at least one of enhancement of oxyS gene expression, enhancement of fixABC gene expression, and combination thereof, is used as the bacterium, or a substance that reduces intracellular hydrogen peroxide concentration of the bacterium is added to the medium.

14 Claims, 4 Drawing Sheets

(51) Int. Cl.
*C12N 1/38* (2006.01)
*C12N 15/74* (2006.01)

(56) References Cited

U.S. PATENT DOCUMENTS

| | | | |
|---|---|---|---|
| 7,833,761 | B2 | 11/2010 | Terashita et al. |
| 8,030,036 | B2 | 10/2011 | Van Dien et al. |
| 8,076,111 | B2 | 12/2011 | Fukui et al. |
| 8,080,396 | B2 | 12/2011 | Shiraga et al. |
| 8,137,938 | B2 | 3/2012 | Nagai et al. |
| 8,192,963 | B2 | 6/2012 | Nishio et al. |
| 8,354,254 | B2 | 1/2013 | Suzuki et al. |
| 8,367,371 | B2 | 2/2013 | Tajima et al. |
| 8,389,249 | B2 | 3/2013 | Hoshino et al. |
| 2005/0233308 | A1 | 10/2005 | Nishio et al. |
| 2007/0065928 | A1* | 3/2007 | Zelder et al. .............. 435/115 |
| 2009/0068712 | A1 | 3/2009 | Terashita et al. |
| 2009/0093029 | A1 | 4/2009 | Usuda et al. |
| 2009/0162908 | A1 | 6/2009 | Yampolskaya et al. |
| 2009/0203090 | A1 | 8/2009 | Ptitsyn et al. |
| 2009/0209012 | A1 | 8/2009 | Hayashi et al. |
| 2009/0246835 | A1 | 10/2009 | Iwatani et al. |
| 2009/0291478 | A1 | 11/2009 | Usuda et al. |
| 2010/0047878 | A1 | 2/2010 | Nagai et al. |
| 2010/0093044 | A1 | 4/2010 | Terashita et al. |
| 2010/0112647 | A1 | 5/2010 | Hara et al. |
| 2010/0190217 | A1 | 7/2010 | Doi et al. |
| 2010/0311137 | A1 | 12/2010 | Brown et al. |
| 2011/0014663 | A1 | 1/2011 | Suzuki et al. |
| 2011/0117613 | A1 | 5/2011 | Hoshino et al. |
| 2011/0189738 | A1* | 8/2011 | Sugiyama et al. .............. 435/106 |
| 2012/0021418 | A1 | 1/2012 | Serata et al. |
| 2012/0219995 | A1 | 8/2012 | Doi et al. |
| 2012/0315678 | A1 | 12/2012 | Hashiro et al. |
| 2013/0005000 | A1 | 1/2013 | Doi et al. |
| 2013/0084609 | A1 | 4/2013 | Suzuki et al. |

FOREIGN PATENT DOCUMENTS

| | | |
|---|---|---|
| JP | 2009-543543 | 12/2009 |
| JP | 2010-110217 | 5/2010 |
| JP | 2010-246483 | 11/2010 |
| JP | 2010-263790 | 11/2010 |
| WO | WO2006/132145 | 12/2006 |
| WO | WO 2009037279 A1 * | 3/2009 |
| WO | WO2009/093703 | 7/2009 |
| WO | WO2009/142286 | 11/2009 |
| WO | WO2009/150856 | 12/2009 |
| WO | WO 2011125015 A2 * | 10/2011 |
| WO | WO2012/077739 | 6/2012 |

OTHER PUBLICATIONS

U.S. Appl. No. 61/651,636, Kunita et al., filed May 25, 2012.*
Buchet, A., et al., "Regulation of the Carnitine Pathway in *Escherichia coli*: Investigation of the cai-fix Divergent Promoter Region," J. Bacteriol. 1998;180(10):2599-2608.
Christman, M. F., et al., "OxyR, a positive regulator of hydrogen peroxide-inducible genes in *Escherichia coli* and *Salmonella typhimurium*, is homologous to a family of bacterial regulatory proteins," Proc. Natl. Acad. Sci. USA 1989;86:3484-3488.
Coves, J., et al., "NADPH-Sulfite Reductase from *Escherichia coli*," J. Biol. Chem. 1993;268(25):18604-18609.
Eichler, K., et al., "The fix *Escherichia coli* region contains four genes related to carnitine metabolism," J. Basic Microbiol. 1995;35(4):217-227.
Fontecave, M., et al., "NAD(P)H:Flavin Oxidoreductase of *Escherichia coli*," J. Biol. Chem. 1987;262 (25):12325-12331.
Keele, B. B., et al., "Superoxide Dismutase from *Escherichia coli* B," J. Biol. Chem. 1970;245(22):6176-6181.
Tsai, M. H., et al., "Phylogenetic characterization of the ubiquitous electron transfer flavoprotein families ETF-alpha and ETF-beta," Res. Microbiol. 1995;146:397-404.
Voet, D., et al., Biochemistry, Second Edition, John Wiley & Sons, Inc., 1995, pp. 666-679.
Walt, A., et al., "The fixA and fixB Genes Are Necessary for Anaerobic Carnitine Reduction in *Escherichia coli*," J. Bacteriol. 2002;184(14):4044-4047.
International Preliminary Report on Patentability for PCT No. PCT/JP2011/078380 (Jun. 20, 2013).
González-Flecha, B., et al., "Role for the *oxyS* Gene in Regulation of Intracellular Hydrogen Peroxide in *Escherichia coli*," J. Bacteriol. 1999;181(12):3833-3836.
Imlay, J. A., et al., "Toxic DNA Damage by Hydrogen Peroxide Through the Fenton Reaction in Vivo and in Vitro," Science 1988;240:640-642.
Imlay, J. A., et al., "Mutagenesis and Stress Responses Induced in *Escherichia coli* by Hydrogen Peroxide," J. Bacteriol. 1987;169(7):2967-2976.
Kohanski, M. A., et al., "Sublethal Antibiotic Treatment Leads to Multidrug Resistance via Radical-Induced Mutagenesis," Mol. Cell 2010;37:311-320.
McDonald, L. C., et al., "Enhanced Recovery of Injured *Escherichia coli* by Compounds That Degrade Hydrogen Peroxide or Block Its Formation," Appl. Environmen. Microbiol. 1983;45(2):360-365.
Usuda, Y., et al., "Dynamic modeling of *Escherichia coli* metabolic and regulatory systems for amino-acid production," J. Biotechnol. 2010;147:17-30.
International Search Report for PCT Patent App. No. PCT/JP2011/078380 (Feb. 7, 2012).

* cited by examiner

SEQUENCE LISTING

<160> NUMBER OF SEQ ID NOS: 17

<210> SEQ ID NO 1
<211> LENGTH: 50
<212> TYPE: DNA
<213> ORGANISM: Artificial Sequence
<220> FEATURE:
<223> OTHER INFORMATION: primer

<400> SEQUENCE: 1
tacccgggga tcctctagag ttccgcgagg cgcaccatat tgttggtgaa                50

<210> SEQ ID NO 2
<211> LENGTH: 49
<212> TYPE: DNA
<213> ORGANISM: Artificial Sequence
<220> FEATURE:
<223> OTHER INFORMATION: primer

<400> SEQUENCE: 2
ttgcatgcct gcaggtcgac agaaacggag cggcacctct tttaaccct                 49

<210> SEQ ID NO 3
<211> LENGTH: 55
<212> TYPE: DNA
<213> ORGANISM: Artificial Sequence
<220> FEATURE:
<223> OTHER INFORMATION: primer

<400> SEQUENCE: 3
tgattacgcc aagcttagga ggttaaatga gctataccct gccatccctg ccgta          55

<210> SEQ ID NO 4
<211> LENGTH: 57
<212> TYPE: DNA
<213> ORGANISM: Artificial Sequence
<220> FEATURE:
<223> OTHER INFORMATION: primer

<400> SEQUENCE: 4
atcctctaga gtcgacgcgg ccgctactta ttttttcgcc gcaaaacgtg ccgctgc        57

<210> SEQ ID NO 5
<211> LENGTH: 45
<212> TYPE: DNA
<213> ORGANISM: Artificial Sequence
<220> FEATURE:
<223> OTHER INFORMATION: primer

<400> SEQUENCE: 5
tacccgggga tcctctagag agagggcgtt ttttcgttaa ttttg                     45

<210> SEQ ID NO 6
<211> LENGTH: 44
<212> TYPE: DNA
<213> ORGANISM: Artificial Sequence
<220> FEATURE:
<223> OTHER INFORMATION: primer

<400> SEQUENCE: 6
ttgcatgcct gcaggtcgat cataaaacgg tcactccttt catg                      44

<210> SEQ ID NO 7
<211> LENGTH: 69
<212> TYPE: DNA
<213> ORGANISM: Artificial Sequence -continued

```
<220> FEATURE:
<223> OTHER INFORMATION: primer

<400> SEQUENCE: 7
cgttattgtt atctagttgt gcaaaacatg ctaatgtagc aactaagcac ttgtctcctg    60
tttactccc                                                           69

<210> SEQ ID NO 8
<211> LENGTH: 66
<212> TYPE: DNA
<213> ORGANISM: Artificial Sequence
<220> FEATURE:
<223> OTHER INFORMATION: primer

<400> SEQUENCE: 8
attagtaaca gccataatgc tctcctgata atgttaaacc tgcttttaag acccactttc    60
acattt                                                              66

<210> SEQ ID NO 9
<211> LENGTH: 110
<212> TYPE: DNA
<213> ORGANISM: Escherichia coli

<400> SEQUENCE: 9
gaaacggagc ggcacctctt ttaacccttg aagtcactgc ccgtttcgag agtttctcaa    60
ctcgaataac taaagccaac gtgaactttt gcggatctcc aggatccgct              110

<210> SEQ ID NO 10
<211> LENGTH: 771
<212> TYPE: DNA
<213> ORGANISM: Escherichia coli
<220> FEATURE:
<221> NAME/KEY: CDS
<222> LOCATION: (1)..(771)

<400> SEQUENCE: 10 atg aag att att act tgc tat aag tgc gtg cct gat gaa cag gat att     48
Met Lys Ile Ile Thr Cys Tyr Lys Cys Val Pro Asp Glu Gln Asp Ile
1               5                   10                  15 gcg gtc aat aat gct gat ggt tca tta gac ttc agc aaa gcc gat gcc    96
Ala Val Asn Asn Ala Asp Gly Ser Leu Asp Phe Ser Lys Ala Asp Ala
                20                  25                  30 aaa ata agc caa tac gat ctc aac gct att gaa gcg gct tgc cag cta   144
Lys Ile Ser Gln Tyr Asp Leu Asn Ala Ile Glu Ala Ala Cys Gln Leu
            35                  40                  45 aag caa cag gca gca gag gcg cag gtg aca gcc tta agt gtg ggc ggt   192
Lys Gln Gln Ala Ala Glu Ala Gln Val Thr Ala Leu Ser Val Gly Gly
        50                  55                  60 aaa gcc ctg acc aac gcc aaa ggg cgt aaa gat gtg cta tcg cgc ggc   240
Lys Ala Leu Thr Asn Ala Lys Gly Arg Lys Asp Val Leu Ser Arg Gly
65                  70                  75                  80 ccg gat gaa ctg att gtg gtg att gat gac cag ttc gag cag gca ctg   288
Pro Asp Glu Leu Ile Val Val Ile Asp Asp Gln Phe Glu Gln Ala Leu
                85                  90                  95 ccg caa caa acg gcg agc gca ctg gct gca gcc gcc cag aaa gca ggc   336
Pro Gln Gln Thr Ala Ser Ala Leu Ala Ala Ala Ala Gln Lys Ala Gly
                100                 105                 110 ttt gat ctg atc ctc tgt ggc gat ggt tct tcc gac ctt tat gcc cag   384
Phe Asp Leu Ile Leu Cys Gly Asp Gly Ser Ser Asp Leu Tyr Ala Gln
            115                 120                 125 cag gtt ggt ctg ctg gtg ggc gaa atc ctc aat att ccg gca gtt aac   432
```

```
                                                                                        Gln Val Gly Leu Leu Val Gly Glu Ile Leu Asn Ile Pro Ala Val Asn
                                                                                                        130                 135                 140 ggc gtc agc aaa att atc tcc ctg acg gca gat acc ctc acc gtt gag           480
Gly Val Ser Lys Ile Ile Ser Leu Thr Ala Asp Thr Leu Thr Val Glu
145                 150                 155                 160 cgc gaa ctg gaa gat gaa acc gaa acc tta agc att ccg ctg cct gcg           528
Arg Glu Leu Glu Asp Glu Thr Glu Thr Leu Ser Ile Pro Leu Pro Ala
                        165                 170                 175 gtt gct gtt tcc act gat atc aac tcc cca caa att cct tcg atg               576
Val Val Ala Val Ser Thr Asp Ile Asn Ser Pro Gln Ile Pro Ser Met
                180                 185                 190 aaa gcc att ctc ggc gcg gcg aaa aag ccc gtc cag gta tgg tcg gcg           624
Lys Ala Ile Leu Gly Ala Ala Lys Lys Pro Val Gln Val Trp Ser Ala
            195                 200                 205 gcg gat att ggt ttt aac gca gag gca gcc tgg tca gaa caa cag gtt           672
Ala Asp Ile Gly Phe Asn Ala Glu Ala Ala Trp Ser Glu Gln Gln Val
210                 215                 220 gcc gcg ccg aaa cag cgc gaa cgt cag cgc atc gtg att gaa ggc gac           720
Ala Ala Pro Lys Gln Arg Glu Arg Gln Arg Ile Val Ile Glu Gly Asp
225                 230                 235                 240 ggc gaa gaa cag atc gcc gca ttt gct gaa aat ctt cgc aaa gtc att           768
Gly Glu Glu Gln Ile Ala Ala Phe Ala Glu Asn Leu Arg Lys Val Ile
                        245                 250                 255 taa                                                                       771

<210> SEQ ID NO 11
<211> LENGTH: 256
<212> TYPE: PRT
<213> ORGANISM: Escherichia coli

<400> SEQUENCE: 11

Met Lys Ile Ile Thr Cys Tyr Lys Cys Val Pro Asp Glu Gln Asp Ile
1               5                   10                  15

Ala Val Asn Asn Ala Asp Gly Ser Leu Asp Phe Ser Lys Ala Asp Ala
                20                  25                  30

Lys Ile Ser Gln Tyr Asp Leu Asn Ala Ile Glu Ala Ala Cys Gln Leu
            35                  40                  45

Lys Gln Gln Ala Ala Glu Ala Gln Val Thr Ala Leu Ser Val Gly Gly
        50                  55                  60

Lys Ala Leu Thr Asn Ala Lys Gly Arg Lys Asp Val Leu Ser Arg Gly
65                  70                  75                  80

Pro Asp Glu Leu Ile Val Ile Asp Asp Gln Phe Glu Gln Ala Leu
                85                  90                  95

Pro Gln Gln Thr Ala Ser Ala Leu Ala Ala Ala Gln Lys Ala Gly
            100                 105                 110

Phe Asp Leu Ile Leu Cys Gly Asp Gly Ser Ser Asp Leu Tyr Ala Gln
        115                 120                 125

Gln Val Gly Leu Leu Val Gly Glu Ile Leu Asn Ile Pro Ala Val Asn
    130                 135                 140

Gly Val Ser Lys Ile Ile Ser Leu Thr Ala Asp Thr Leu Thr Val Glu
145                 150                 155                 160

Arg Glu Leu Glu Asp Glu Thr Glu Thr Leu Ser Ile Pro Leu Pro Ala
                165                 170                 175

Val Val Ala Val Ser Thr Asp Ile Asn Ser Pro Gln Ile Pro Ser Met
            180                 185                 190

Lys Ala Ile Leu Gly Ala Ala Lys Lys Pro Val Gln Val Trp Ser Ala
        195                 200                 205
```

```
Ala Asp Ile Gly Phe Asn Ala Glu Ala Trp Ser Glu Gln Gln Val
    210                 215                 220

Ala Ala Pro Lys Gln Arg Glu Arg Gln Arg Ile Val Ile Glu Gly Asp
225                 230                 235                 240

Gly Glu Glu Gln Ile Ala Ala Phe Ala Glu Asn Leu Arg Lys Val Ile
                245                 250                 255

<210> SEQ ID NO 12
<211> LENGTH: 942
<212> TYPE: DNA
<213> ORGANISM: Escherichia coli
<220> FEATURE:
<221> NAME/KEY: CDS
<222> LOCATION: (1)..(942)

<400> SEQUENCE: 12 atg aac acg ttt tct caa gtc tgg gta ttc agc gat acc cct tct cgt      48
Met Asn Thr Phe Ser Gln Val Trp Val Phe Ser Asp Thr Pro Ser Arg
1               5                   10                  15 ctg ccg gaa ctg atg aac ggt gcg cag gct tta gct aat caa atc aac      96
Leu Pro Glu Leu Met Asn Gly Ala Gln Ala Leu Ala Asn Gln Ile Asn
                20                  25                  30 acc ttt gtc ctc aat gat gcc gac ggc gca cag gca atc cag ctc ggc     144
Thr Phe Val Leu Asn Asp Ala Asp Gly Ala Gln Ala Ile Gln Leu Gly
            35                  40                  45 gct aat cat gtc tgg aaa tta aac ggc aaa ccg gac gat cgg atg atc     192
Ala Asn His Val Trp Lys Leu Asn Gly Lys Pro Asp Asp Arg Met Ile
        50                  55                  60 gaa gat tac gcc ggt gtc atg gct gac act att cgc cag cac ggc gca     240
Glu Asp Tyr Ala Gly Val Met Ala Asp Thr Ile Arg Gln His Gly Ala
65                  70                  75                  80 gac ggc ctg gtg ctg ctg cca aac acc cgt cgc ggc aaa tta ctg gcg     288
Asp Gly Leu Val Leu Leu Pro Asn Thr Arg Arg Gly Lys Leu Leu Ala
                85                  90                  95 gca aaa ctg ggt tat cgc ctt aaa gcg gcg gtg tct aac gat gcc agc     336
Ala Lys Leu Gly Tyr Arg Leu Lys Ala Ala Val Ser Asn Asp Ala Ser
            100                 105                 110 acc gtc agc gta cag gac ggt aaa gcg aca gtg aaa cac atg gtt tac     384
Thr Val Ser Val Gln Asp Gly Lys Ala Thr Val Lys His Met Val Tyr
        115                 120                 125 ggt ggt ctg gcg att ggc gaa gaa cgc att gcc acg ccg tat gcg gta     432
Gly Gly Leu Ala Ile Gly Glu Glu Arg Ile Ala Thr Pro Tyr Ala Val
130                 135                 140 ctg acc atc agc agc ggc acg ttc gat gcg gct cag cca gac gcg tca     480
Leu Thr Ile Ser Ser Gly Thr Phe Asp Ala Ala Gln Pro Asp Ala Ser
145                 150                 155                 160 cgc act ggc gaa acg cac acc gtg gag tgg cag gct ccg gct gtg gcg     528
Arg Thr Gly Glu Thr His Thr Val Glu Trp Gln Ala Pro Ala Val Ala
                165                 170                 175 att acc cgc acg gca acc cag gcg cgc cag agc aac agc gtc gat ctc     576
Ile Thr Arg Thr Ala Thr Gln Ala Arg Gln Ser Asn Ser Val Asp Leu
            180                 185                 190 gac aaa gcc cgt ctg gtg gtc agc gtc ggt cgc ggt att ggc agc aaa     624
Asp Lys Ala Arg Leu Val Val Ser Val Gly Arg Gly Ile Gly Ser Lys
        195                 200                 205 gag aac att gcg ctg gca gaa cag ctt tgc aag gcg ata ggt gcg gag     672
Glu Asn Ile Ala Leu Ala Glu Gln Leu Cys Lys Ala Ile Gly Ala Glu
    210                 215                 220 ttg gcc tgt tct cgt ccg gtg gcg gaa aac gaa aaa tgg atg gag cac     720
Leu Ala Cys Ser Arg Pro Val Ala Glu Asn Glu Lys Trp Met Glu His
```

```
                    225                 230                 235                 240
gaa cgc tat gtc ggt atc tcc aac ctg atg ctg aaa cct gaa ctg tac        768
Glu Arg Tyr Val Gly Ile Ser Asn Leu Met Leu Lys Pro Glu Leu Tyr
                245                 250                 255 ctg gcg gtg ggg atc tcc ggg cag atc cag cac atg gtt ggc gct aac        816
Leu Ala Val Gly Ile Ser Gly Gln Ile Gln His Met Val Gly Ala Asn
                260                 265                 270 gcg tcg caa acc att ttc gcc atc aat aaa gat aaa aat gcg ccg atc        864
Ala Ser Gln Thr Ile Phe Ala Ile Asn Lys Asp Lys Asn Ala Pro Ile
            275                 280                 285 ttc cag tac gcg gat tac ggc att gtt ggc gac gcc gtg aag atc ctt        912
Phe Gln Tyr Ala Asp Tyr Gly Ile Val Gly Asp Ala Val Lys Ile Leu
        290                 295                 300 ccg gcg ctg acc gca gct tta gcg cgt tga                                942
Pro Ala Leu Thr Ala Ala Leu Ala Arg
305                 310
```

<210> SEQ ID NO 13
<211> LENGTH: 313
<212> TYPE: PRT
<213> ORGANISM: Escherichia coli

<400> SEQUENCE: 13

```
Met Asn Thr Phe Ser Gln Val Trp Val Phe Ser Asp Thr Pro Ser Arg
1               5                   10                  15

Leu Pro Glu Leu Met Asn Gly Ala Gln Ala Leu Ala Asn Gln Ile Asn
                20                  25                  30

Thr Phe Val Leu Asn Asp Ala Asp Gly Ala Gln Ala Ile Gln Leu Gly
            35                  40                  45

Ala Asn His Val Trp Lys Leu Asn Gly Lys Pro Asp Asp Arg Met Ile
        50                  55                  60

Glu Asp Tyr Ala Gly Val Met Ala Asp Thr Ile Arg Gln His Gly Ala
65                  70                  75                  80

Asp Gly Leu Val Leu Leu Pro Asn Thr Arg Arg Gly Lys Leu Leu Ala
                85                  90                  95

Ala Lys Leu Gly Tyr Arg Leu Lys Ala Ala Val Ser Asn Asp Ala Ser
            100                 105                 110

Thr Val Ser Val Gln Asp Gly Lys Ala Thr Val Lys His Met Val Tyr
        115                 120                 125

Gly Gly Leu Ala Ile Gly Glu Glu Arg Ile Ala Thr Pro Tyr Ala Val
    130                 135                 140

Leu Thr Ile Ser Ser Gly Thr Phe Asp Ala Ala Gln Pro Asp Ala Ser
145                 150                 155                 160

Arg Thr Gly Glu Thr His Thr Val Glu Trp Gln Ala Pro Ala Val Ala
                165                 170                 175

Ile Thr Arg Thr Ala Thr Gln Ala Arg Gln Ser Asn Ser Val Asp Leu
            180                 185                 190

Asp Lys Ala Arg Leu Val Val Ser Val Gly Arg Gly Ile Gly Ser Lys
        195                 200                 205

Glu Asn Ile Ala Leu Ala Glu Gln Leu Cys Lys Ala Ile Gly Ala Glu
    210                 215                 220

Leu Ala Cys Ser Arg Pro Val Ala Glu Asn Glu Lys Trp Met Glu His
225                 230                 235                 240

Glu Arg Tyr Val Gly Ile Ser Asn Leu Met Leu Lys Pro Glu Leu Tyr
                245                 250                 255

Leu Ala Val Gly Ile Ser Gly Gln Ile Gln His Met Val Gly Ala Asn
```

```
                    260                     265                     270
Ala Ser Gln Thr Ile Phe Ala Ile Asn Lys Asp Lys Asn Ala Pro Ile
            275                     280                     285

Phe Gln Tyr Ala Asp Tyr Gly Ile Val Gly Asp Ala Val Lys Ile Leu
            290                     295                     300

Pro Ala Leu Thr Ala Ala Leu Ala Arg
305                 310

<210> SEQ ID NO 14
<211> LENGTH: 1287
<212> TYPE: DNA
<213> ORGANISM: Artificial Sequence
<220> FEATURE:
<223> OTHER INFORMATION: primer
<220> FEATURE:
<221> NAME/KEY: CDS
<222> LOCATION: (1)..(1287)

<400> SEQUENCE: 14 atg tcc gaa gat atc ttt gac gcc atc atc gtc ggt gca ggg ctt gcc      48
Met Ser Glu Asp Ile Phe Asp Ala Ile Ile Val Gly Ala Gly Leu Ala
1               5                   10                  15 ggt tcg gtt gcc gca ctg gtg ctc gcc cgc gaa ggt gcg caa gtg tta      96
Gly Ser Val Ala Ala Leu Val Leu Ala Arg Glu Gly Ala Gln Val Leu
            20                  25                  30 gtt atc gag cgt ggc aat tcc gca ggt gcc aag aac gtc acc ggc ggg     144
Val Ile Glu Arg Gly Asn Ser Ala Gly Ala Lys Asn Val Thr Gly Gly
        35                  40                  45 cgt ctc tat gcc cac agt ctg gaa cac att att cct ggt ttc gcc gac     192
Arg Leu Tyr Ala His Ser Leu Glu His Ile Ile Pro Gly Phe Ala Asp
    50                  55                  60 tcc gcc ccc gta gaa cgc ctg atc acc cat gaa aaa ctc gcg ttt atg     240
Ser Ala Pro Val Glu Arg Leu Ile Thr His Glu Lys Leu Ala Phe Met
65                  70                  75                  80 acg gaa aag tca gcg atg act atg gac tac tgc aat ggt gac gaa acc     288
Thr Glu Lys Ser Ala Met Thr Met Asp Tyr Cys Asn Gly Asp Glu Thr
                85                  90                  95 tcg cca tcc cag cgt tct tac tcc gtt ttg cgc agt aaa ttt gat gcc     336
Ser Pro Ser Gln Arg Ser Tyr Ser Val Leu Arg Ser Lys Phe Asp Ala
            100                 105                 110 tgg ctg atg gag cag gcc gaa gaa gcg ggc gcg cag tta att acc ggg     384
Trp Leu Met Glu Gln Ala Glu Glu Ala Gly Ala Gln Leu Ile Thr Gly
        115                 120                 125 atc cgc gtc gat aac ctc gta cag cgc gat ggc aaa gtc gtc ggt gta     432
Ile Arg Val Asp Asn Leu Val Gln Arg Asp Gly Lys Val Val Gly Val
    130                 135                 140 gaa gcc gat ggc gat gtg att gaa gcg aaa acg gtg atc ctt gct gat     480
Glu Ala Asp Gly Asp Val Ile Glu Ala Lys Thr Val Ile Leu Ala Asp
145                 150                 155                 160 ggg gtg aac tcc atc ctt gcc gaa aaa ttg ggg atg gca aaa cgc gtc     528
Gly Val Asn Ser Ile Leu Ala Glu Lys Leu Gly Met Ala Lys Arg Val
                165                 170                 175 aaa ccg acg gat gtg gcg gtt ggc gtg aag gaa ctg atc gag tta ccg     576
Lys Pro Thr Asp Val Ala Val Gly Val Lys Glu Leu Ile Glu Leu Pro
            180                 185                 190 aag tcg gtt att gaa gac cgt ttt cag ttg cag ggt aat cag ggg gcg     624
Lys Ser Val Ile Glu Asp Arg Phe Gln Leu Gln Gly Asn Gln Gly Ala
        195                 200                 205 gct tgc ctg ttt gcg gga tca ccc acc gat ggc ctg atg ggc ggc ggc     672
Ala Cys Leu Phe Ala Gly Ser Pro Thr Asp Gly Leu Met Gly Gly Gly
    210                 215                 220
```

-continued

| | | | | | | | | | | | | | | | | |
|---|---|---|---|---|---|---|---|---|---|---|---|---|---|---|---|---|
| ttc | ctt | tat | acc | aat | gaa | aac | acc | ctg | tcg | ctg | ggg | ctg | gtt | tgt | ggt | 720 |
| Phe | Leu | Tyr | Thr | Asn | Glu | Asn | Thr | Leu | Ser | Leu | Gly | Leu | Val | Cys | Gly | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| ttg | cat | cat | ctg | cat | gac | gcg | aaa | aaa | tcg | gtg | ccg | caa | atg | ctg | gaa | 768 |
| Leu | His | His | Leu | His | Asp | Ala | Lys | Lys | Ser | Val | Pro | Gln | Met | Leu | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| gat | ttc | aaa | cag | cat | ccg | gcc | gtt | gca | ccg | ctg | atc | gcg | ggc | ggc | aag | 816 |
| Asp | Phe | Lys | Gln | His | Pro | Ala | Val | Ala | Pro | Leu | Ile | Ala | Gly | Gly | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| ctg | gtg | gaa | tat | tcc | gct | cac | gta | gtg | ccg | gaa | gca | ggc | atc | aac | atg | 864 |
| Leu | Val | Glu | Tyr | Ser | Ala | His | Val | Val | Pro | Glu | Ala | Gly | Ile | Asn | Met | |
| | | 275 | | | | | 280 | | | | | 285 | | | | |

| | | | | | | | | | | | | | | | | |
|---|---|---|---|---|---|---|---|---|---|---|---|---|---|---|---|---|
| ctg | ccg | gag | ttg | gtt | ggt | gac | ggc | gta | ttg | att | gcc | ggt | gat | gcc | gcc | 912 |
| Leu | Pro | Glu | Leu | Val | Gly | Asp | Gly | Val | Leu | Ile | Ala | Gly | Asp | Ala | Ala | |
| | 290 | | | | | 295 | | | | | 300 | | | | | |

| | | | | | | | | | | | | | | | | |
|---|---|---|---|---|---|---|---|---|---|---|---|---|---|---|---|---|
| gga | atg | tgt | atg | aac | ctc | ggt | ttt | acc | att | cgc | ggt | atg | gat | ctg | gcg | 960 |
| Gly | Met | Cys | Met | Asn | Leu | Gly | Phe | Thr | Ile | Arg | Gly | Met | Asp | Leu | Ala | |
| 305 | | | | 310 | | | | | 315 | | | | | 320 | | |

| | | | | | | | | | | | | | | | | |
|---|---|---|---|---|---|---|---|---|---|---|---|---|---|---|---|---|
| att | gcc | gcc | ggg | gaa | gcc | gca | gca | aaa | acc | gtg | ctt | tca | gcg | atg | aaa | 1008 |
| Ile | Ala | Ala | Gly | Glu | Ala | Ala | Ala | Lys | Thr | Val | Leu | Ser | Ala | Met | Lys | |
| | | | | 325 | | | | | 330 | | | | | 335 | | |

| | | | | | | | | | | | | | | | | |
|---|---|---|---|---|---|---|---|---|---|---|---|---|---|---|---|---|
| agc | gac | gat | ttc | agt | aag | caa | aaa | ctg | gcg | gaa | tat | cgt | cag | cat | ctt | 1056 |
| Ser | Asp | Asp | Phe | Ser | Lys | Gln | Lys | Leu | Ala | Glu | Tyr | Arg | Gln | His | Leu | |
| | | | 340 | | | | | 345 | | | | | 350 | | | |

| | | | | | | | | | | | | | | | | |
|---|---|---|---|---|---|---|---|---|---|---|---|---|---|---|---|---|
| gag | agt | ggt | ccg | ctg | cgc | gat | atg | cgt | atg | tac | cag | aaa | cta | ccg | gcg | 1104 |
| Glu | Ser | Gly | Pro | Leu | Arg | Asp | Met | Arg | Met | Tyr | Gln | Lys | Leu | Pro | Ala | |
| | | 355 | | | | | 360 | | | | | 365 | | | | |

| | | | | | | | | | | | | | | | | |
|---|---|---|---|---|---|---|---|---|---|---|---|---|---|---|---|---|
| ttc | ctt | gat | aac | cca | cgc | atg | ttt | agc | ggc | tac | ccg | gag | ctg | gcg | gtg | 1152 |
| Phe | Leu | Asp | Asn | Pro | Arg | Met | Phe | Ser | Gly | Tyr | Pro | Glu | Leu | Ala | Val | |
| | 370 | | | | | 375 | | | | | 380 | | | | | |

| | | | | | | | | | | | | | | | | |
|---|---|---|---|---|---|---|---|---|---|---|---|---|---|---|---|---|
| ggt | gtg | gcg | cgt | gac | ctg | ttc | acc | att | gat | ggc | agc | gcg | ccg | gaa | ctg | 1200 |
| Gly | Val | Ala | Arg | Asp | Leu | Phe | Thr | Ile | Asp | Gly | Ser | Ala | Pro | Glu | Leu | |
| 385 | | | | 390 | | | | | 395 | | | | | 400 | | |

| | | | | | | | | | | | | | | | | |
|---|---|---|---|---|---|---|---|---|---|---|---|---|---|---|---|---|
| atg | cgc | aag | aaa | atc | ctc | cgc | cac | ggc | aag | aaa | gtg | ggc | ttc | atc | aat | 1248 |
| Met | Arg | Lys | Lys | Ile | Leu | Arg | His | Gly | Lys | Lys | Val | Gly | Phe | Ile | Asn | |
| | | | | 405 | | | | | 410 | | | | | 415 | | |

| | | | | | | | | | | |
|---|---|---|---|---|---|---|---|---|---|---|
| cta | atc | aag | gat | ggc | atg | aaa | gga | gtg | acc | gtt | tta | tga | 1287 |
| Leu | Ile | Lys | Asp | Gly | Met | Lys | Gly | Val | Thr | Val | Leu | | |
| | | | 420 | | | | | 425 | | | | | |

<210> SEQ ID NO 15
<211> LENGTH: 428
<212> TYPE: PRT
<213> ORGANISM: Artificial Sequence
<220> FEATURE:
<223> OTHER INFORMATION: Synthetic Construct

<400> SEQUENCE: 15

Met Ser Glu Asp Ile Phe Asp Ala Ile Ile Val Gly Ala Gly Leu Ala
1               5                   10                  15

Gly Ser Val Ala Ala Leu Val Leu Ala Arg Glu Gly Ala Gln Val Leu
            20                  25                  30

Val Ile Glu Arg Gly Asn Ser Ala Gly Ala Lys Asn Val Thr Gly Gly
        35                  40                  45

Arg Leu Tyr Ala His Ser Leu Glu His Ile Ile Pro Gly Phe Ala Asp
    50                  55                  60

Ser Ala Pro Val Glu Arg Leu Ile Thr His Glu Lys Leu Ala Phe Met
65                  70                  75                  80

Thr Glu Lys Ser Ala Met Thr Met Asp Tyr Cys Asn Gly Asp Glu Thr

|   |   |   |   |   | 85  |   |   |   |   | 90  |   |   |   |   | 95  |   |
|---|---|---|---|---|---|---|---|---|---|---|---|---|---|---|---|---|

Ser Pro Ser Gln Arg Ser Tyr Ser Val Leu Arg Ser Lys Phe Asp Ala
                    100                 105                 110

Trp Leu Met Glu Gln Ala Glu Glu Ala Gly Ala Gln Leu Ile Thr Gly
            115                 120                 125

Ile Arg Val Asp Asn Leu Val Gln Arg Asp Gly Lys Val Val Gly Val
    130                 135                 140

Glu Ala Asp Gly Asp Val Ile Glu Ala Lys Thr Val Ile Leu Ala Asp
145                 150                 155                 160

Gly Val Asn Ser Ile Leu Ala Glu Lys Leu Gly Met Ala Lys Arg Val
                165                 170                 175

Lys Pro Thr Asp Val Ala Val Gly Val Lys Glu Leu Ile Glu Leu Pro
            180                 185                 190

Lys Ser Val Ile Glu Asp Arg Phe Gln Leu Gln Gly Asn Gln Gly Ala
        195                 200                 205

Ala Cys Leu Phe Ala Gly Ser Pro Thr Asp Gly Leu Met Gly Gly Gly
    210                 215                 220

Phe Leu Tyr Thr Asn Glu Asn Thr Leu Ser Leu Gly Leu Val Cys Gly
225                 230                 235                 240

Leu His His Leu His Asp Ala Lys Lys Ser Val Pro Gln Met Leu Glu
                245                 250                 255

Asp Phe Lys Gln His Pro Ala Val Ala Pro Leu Ile Ala Gly Gly Lys
            260                 265                 270

Leu Val Glu Tyr Ser Ala His Val Val Pro Glu Ala Gly Ile Asn Met
        275                 280                 285

Leu Pro Glu Leu Val Gly Asp Gly Val Leu Ile Ala Gly Asp Ala Ala
    290                 295                 300

Gly Met Cys Met Asn Leu Gly Phe Thr Ile Arg Gly Met Asp Leu Ala
305                 310                 315                 320

Ile Ala Ala Gly Glu Ala Ala Lys Thr Val Leu Ser Ala Met Lys
                325                 330                 335

Ser Asp Asp Phe Ser Lys Gln Lys Leu Ala Glu Tyr Arg Gln His Leu
            340                 345                 350

Glu Ser Gly Pro Leu Arg Asp Met Arg Met Tyr Gln Lys Leu Pro Ala
        355                 360                 365

Phe Leu Asp Asn Pro Arg Met Phe Ser Gly Tyr Pro Glu Leu Ala Val
    370                 375                 380

Gly Val Ala Arg Asp Leu Phe Thr Ile Asp Gly Ser Ala Pro Glu Leu
385                 390                 395                 400

Met Arg Lys Lys Ile Leu Arg His Gly Lys Lys Val Gly Phe Ile Asn
                405                 410                 415

Leu Ile Lys Asp Gly Met Lys Gly Val Thr Val Leu
            420                 425

<210> SEQ ID NO 16
<211> LENGTH: 621
<212> TYPE: DNA
<213> ORGANISM: Escherichia coli
<220> FEATURE:
<221> NAME/KEY: CDS
<222> LOCATION: (1)..(621)

<400> SEQUENCE: 16 atg agc tat acc ctg cca tcc ctg ccg tat gct tac gat gcc ctg gaa    48
Met Ser Tyr Thr Leu Pro Ser Leu Pro Tyr Ala Tyr Asp Ala Leu Glu
1               5                   10                  15

```
ccg cac ttc gat aag cag acc atg gaa atc cac cac acc aaa cac cat      96
Pro His Phe Asp Lys Gln Thr Met Glu Ile His His Thr Lys His His
         20                  25                  30 cag acc tac gta aac aac gcc aac gcg gcg ctg gaa agc ctg cca gaa     144
Gln Thr Tyr Val Asn Asn Ala Asn Ala Ala Leu Glu Ser Leu Pro Glu
         35                  40                  45 ttt gcc aac ctg ccg gtt gaa gag ctg atc acc aaa ctg gac cag ctg     192
Phe Ala Asn Leu Pro Val Glu Glu Leu Ile Thr Lys Leu Asp Gln Leu
 50                  55                  60 cca gca gac aag aaa acc gta ctg cgc aac aac gct ggc ggt cac gct     240
Pro Ala Asp Lys Lys Thr Val Leu Arg Asn Asn Ala Gly Gly His Ala
 65                  70                  75                  80 aac cac agc ctg ttc tgg aaa ggt ctg aaa aaa ggc acc acc ctg cag     288
Asn His Ser Leu Phe Trp Lys Gly Leu Lys Lys Gly Thr Thr Leu Gln
                 85                  90                  95 ggt gac ctg aaa gcg gct atc gaa cgt gac ttc ggt tcc gtt gat aac     336
Gly Asp Leu Lys Ala Ala Ile Glu Arg Asp Phe Gly Ser Val Asp Asn
            100                 105                 110 ttc aaa gca gaa ttt gaa aaa gcg gca gct tcc cgc ttt ggt tcc ggc     384
Phe Lys Ala Glu Phe Glu Lys Ala Ala Ala Ser Arg Phe Gly Ser Gly
        115                 120                 125 tgg gca tgg ctg gtg ctg aaa ggc gat aaa ctg gcg gtg gtt tct act     432
Trp Ala Trp Leu Val Leu Lys Gly Asp Lys Leu Ala Val Val Ser Thr
130                 135                 140 gct aac cag gat tct ccg ctg atg ggt gaa gct att tct ggc gct tcc     480
Ala Asn Gln Asp Ser Pro Leu Met Gly Glu Ala Ile Ser Gly Ala Ser
145                 150                 155                 160 ggc ttc ccg att atg ggc ctg gat gtg tgg gaa cat gct tac tac ctg     528
Gly Phe Pro Ile Met Gly Leu Asp Val Trp Glu His Ala Tyr Tyr Leu
                165                 170                 175 aaa ttc cag aac cgc cgt ccg gac tac att aaa gag ttc tgg aac gtg     576
Lys Phe Gln Asn Arg Arg Pro Asp Tyr Ile Lys Glu Phe Trp Asn Val
            180                 185                 190 gtg aac tgg gac gaa gca gcg gca cgt ttt gcg gcg aaa aaa taa         621
Val Asn Trp Asp Glu Ala Ala Ala Arg Phe Ala Ala Lys Lys
        195                 200                 205

<210> SEQ ID NO 17
<211> LENGTH: 206
<212> TYPE: PRT
<213> ORGANISM: Escherichia coli

<400> SEQUENCE: 17

Met Ser Tyr Thr Leu Pro Ser Leu Pro Tyr Ala Tyr Asp Ala Leu Glu
 1               5                  10                  15

Pro His Phe Asp Lys Gln Thr Met Glu Ile His His Thr Lys His His
             20                  25                  30

Gln Thr Tyr Val Asn Asn Ala Asn Ala Ala Leu Glu Ser Leu Pro Glu
         35                  40                  45

Phe Ala Asn Leu Pro Val Glu Glu Leu Ile Thr Lys Leu Asp Gln Leu
     50                  55                  60

Pro Ala Asp Lys Lys Thr Val Leu Arg Asn Asn Ala Gly Gly His Ala
 65                  70                  75                  80

Asn His Ser Leu Phe Trp Lys Gly Leu Lys Lys Gly Thr Thr Leu Gln
                 85                  90                  95

Gly Asp Leu Lys Ala Ala Ile Glu Arg Asp Phe Gly Ser Val Asp Asn
            100                 105                 110

Phe Lys Ala Glu Phe Glu Lys Ala Ala Ala Ser Arg Phe Gly Ser Gly
```

```
                115                 120                 125
Trp Ala Trp Leu Val Leu Lys Gly Asp Lys Leu Ala Val Val Ser Thr
        130                 135                 140

Ala Asn Gln Asp Ser Pro Leu Met Gly Glu Ala Ile Ser Gly Ala Ser
145                 150                 155                 160

Gly Phe Pro Ile Met Gly Leu Asp Val Trp Glu His Ala Tyr Tyr Leu
                165                 170                 175

Lys Phe Gln Asn Arg Arg Pro Asp Tyr Ile Lys Glu Phe Trp Asn Val
                180                 185                 190

Val Asn Trp Asp Glu Ala Ala Ala Arg Phe Ala Ala Lys Lys
        195                 200                 205
```

METHOD FOR PRODUCING AN L-AMINO ACID

This application is a Continuation of, and claims priority under 35 U.S.C. §120 to, International Application No. PCT/JP2011/078380, filed Dec. 8, 2011, and claims priority therethrough under 35 U.S.C. §119 to Japanese Patent Application No. 2010-276062, filed Dec. 10, 2010, the entireties of which are incorporated by reference herein. Also, the Sequence Listing filed electronically herewith is hereby incorporated by reference (File name: 2013-06-07T_US-497_Seq_List; File size: 30 KB; Date recorded: Jun. 7, 2013).

BACKGROUND OF THE INVENTION

1. Field of the Invention

The present invention relates to methods for producing an L-amino acid utilizing a bacterium, in particular, such a method for producing an L-amino acid utilizing a fatty acid or an alcohol such as glycerol as a raw material, and a bacterium used for the method. L-Amino acids are industrially useful as additives for animal feed, components of health food, amino acid infusions, and so forth.

2. Brief Description of the Related Art

In the industrial production of L-amino acids by fermentation, saccharides, i.e., glucose, fructose, sucrose, blackstrap molasses, starch hydrolysate, and so forth, are used as a carbon source. Moreover, methods for producing an L-amino acid using a fatty acid (WO2009/142286), glycerol (U.S. Patent App. Pub. No. 2009093029), or ethanol (WO2008/010565) as a carbon source have also been disclosed.

In various organisms, in general, an electron withdrawn from Acyl-CoA by Acyl-CoA dehydrogenase at the time of fatty acid utilization is transferred to the oxidized electron transferring flavoprotein ($ETF_{ox}$) via $FADH_2$ to form the reduced electron transferring flavoprotein, $ETF_{red}$, and an electron is further transferred from $ETF_{red}$ to ubiquinone by ETF ubiquinone oxidoreductase, and then to the respiratory chain (Voet, D. et al., 1995, Biochemistry, Second edition, John Wiley & Sons, Inc., New York). However, for bacteria belonging to the family Enterobacteriaceae, electron transferring flavoprotein (ETF) and ETF ubiquinone oxidoreductase have not been reported to date.

Furthermore, it can be estimated from the descriptions of Coves, J. et al., 1993, J. Biol. Chem., 268(25):18604-18609, Fontecave, M. et al., 1987, J. Biol. Chem., 262(25):12325-12331, and so forth, that at the time of the ethanol utilization in bacteria belonging to the family Enterobacteriaceae, an electron is transferred from NADH, which is considered to be abundantly generated in bacterial cells, or from NADH via NADPH to FAD, and a marked amount of $FADH_2$ accumulates as a result.

For *Escherichia coli*, fixA (yaaQ) and fixB (yaaR) have been reported as genes coding for ETF homologues that can transfer electrons from $FADH_2$ (Tsai, M. H. et al., 1995, Res. Microbiol., 146:397-404). The fixA and fixB genes constitute the fixABCX operon together with the fixC and fixX genes, and expression thereof is induced under anaerobic conditions in the presence of carnitine (Eichler, K. et al., 1995, J. Basic Microbiol., 35:217-227 and Buchet, A. et al., 1998, J. Bacteriol., 180:2599-2608). There is a report suggesting that the proteins encoded by these genes transfer an electron to crotonobetaine reductase which participates in carnitine metabolism (Walt, A. et al., 2002, J. Bacteriol., 184:4044-4047). In addition, it is predicted that fixA encodes the electron transferring flavoprotein β subunit, fixB encodes the α subunit of the same protein, fixC encodes the electron transferring flavoprotein-quinone oxidoreductase, and fixX encodes a ferredoxin-like protein (Buchet, A. et al., 1998, J. Bacteriol., 180: 2599-2608). As described above, although there are reports suggesting involvement of fixA, fixB, and fixC in the carnitine metabolism, it has not been reported to date that they participate in the electron transport from Acyl-CoA dehydrogenase to the respiratory chain.

sodA encodes superoxide dismutase, which catalyzes the conversion of superoxide into hydrogen peroxide (Keele, B. B. et al., 1970, J. Biol. Chem., 245 (22):6176-6181). However, there has not been reported a relationship between the superoxide dismutase activity and production of an amino acid.

As a defense system against intracellular hydrogen peroxide in the bacteria belonging to the family Enterobacteriaceae, the action of the transcription factor OxyR has been reported, which activates the genes for eliminating oxidation stress (Christman, M. F. et al., 1989, Proc. Natl. Acad. Sci. USA., 86(10):3484-3488). It has been reported that, among the genes activated by OxyR, the low molecular RNA coding gene oxyS controls secretion of hydrogen peroxide from bacterial cells (Gonzalez-Flecha, B. et al., 1999, J. Bacteriol., 181(12):3833-3836). However, there has not been reported production of L-amino acid using a microorganism in which oxyS gene expression is enhanced.

It has been reported that thiourea has an effect of suppressing oxidation stress including hydrogen peroxide for *Escherichia coli* (Kohanski, M. A. et al., 2010, Molecular Cell, 37:311-320). However, any relation between thiourea and L-amino acid production is not known.

SUMMARY OF THE INVENTION

One of numerous aspects of the present invention includes a method for efficiently producing an L-amino acid utilizing a bacterium belonging to the family Enterobacteriaceae from a carbon source, especially a fatty acid or an alcohol such as ethanol and glycerol, as a raw material, and a bacterium used for the method.

As described above, it is known that at the time of the ethanol utilization in the bacteria belonging to the family Enterobacteriaceae, an electron withdrawn from Acyl-CoA by the Acyl-CoA dehydrogenase is transferred to the respiratory chain via $FADH_2$. The inventors of the present disclosure estimated that this electron was finally transferred to free oxygen to generate hydrogen peroxide, and as a result, cells were injured by hydrogen peroxide generated at the time of the fatty acid utilization, and further estimated that secretion of hydrogen peroxide generated in the cells was promoted by enhancement of the oxyS gene expression, and thus the injury by hydrogen peroxide was reduced. Therefore, the inventors enhanced expression of the oxyS gene in bacteria belonging to the family Enterobacteriaceae. As a result, reduction of intracellular hydrogen peroxide concentration and improvement in growth were confirmed, and it was further found that L-amino acid-producing ability was improved.

The inventors of the present disclosure further estimated that cells of the bacteria belonging to the family Enterobacteriaceae were injured by hydrogen peroxide generated from the electron derived from $FADH_2$ and oxygen not only at the time of fatty acid utilization, but also at the time of ethanol utilization, but this injury could be reduced by enhancing expression of ETF. Therefore, expression of ETF was enhanced in bacteria belonging to the family Enterobacteriaceae, and it was found that L-amino acid-producing ability was improved.

The inventors of the present disclosure further estimated that, in the bacteria belonging to the family Enterobacteriaceae, hydrogen peroxide was generated by superoxide dismutase, and as a result, cells were injured. Therefore, the inventors amplified the sodA gene in bacteria belonging to the family Enterobacteriaceae, and it was found that intracellular hydrogen peroxide concentration increased, and growth was degraded. It was further found that if bacteria belonging to the family Enterobacteriaceae were cultured in a medium containing thiourea, hydrogen peroxide concentration in the bacterial cells reduced, and L-amino acid-producing ability was improved.

The subject matter described herein was accomplished on the basis of the aforementioned findings that, by reducing hydrogen peroxide concentration in the cells of bacteria belonging to the family Enterobacteriaceae, L-amino acid-producing ability could be improved.

Other aspects of the present invention thus include the following.

(1) A method for producing an L-amino acid comprising culturing a bacterium which belongs to the family Enterobacteriaceae and has an L-amino acid-producing ability in a medium containing a carbon source selected from the group consisting of a fatty acid and an alcohol, and collecting the L-amino acid from the medium, wherein the method comprises intracellular hydrogen peroxide concentration of the bacterium.

(2) The method as described above, wherein the bacterium has been modified so that the intracellular hydrogen peroxide concentration is reduced.

(3) The method as described above, wherein a substance that reduces intracellular hydrogen peroxide concentration of the bacterium is added to the medium.

(4) The method as described above, wherein the bacterium belongs to the genus *Escherichia*, *Pantoea*, or *Enterobacter*.

(5) The method as described above, wherein the bacterium is *Escherichia coli*, *Pantoea ananatis*, or *Enterobacter aerogenes*.

(6) The method as described above, wherein the bacterium has been subjected to a modification selected from the group consisting of enhancement of oxyS gene expression, enhancement of fixABC gene expression, and a combination thereof.

(7) The method as described above, wherein the oxyS gene encodes RNA having the nucleotide sequence of SEQ ID NO: 9, or a conservative variant thereof.

(8) The method as described above, wherein the fixABC genes encode proteins having the amino acid sequences of SEQ ID NOS: 11, 13, and 15, or a conservative variant thereof.

(9) The method as described above, wherein the substance that reduces the intracellular hydrogen peroxide concentration is thiourea.

(10) The method as described above, wherein the carbon source is a fatty acid.

(11) The method as described above, wherein the fatty acid is oleic acid.

(12) The method as described above, wherein the fatty acid is a mixture of fatty acids derived from a fat or oil.

(13) The method as described above, wherein the carbon source is an alcohol.

(14) The method as described above, wherein the alcohol is glycerol.

(15) The method as described above, wherein the alcohol is ethanol.

(16) The method as described above, wherein the carbon source is a mixture of a fatty acid and glycerol obtained by hydrolyzing a fat or oil.

(17) The method as described above, wherein the bacterium is *Escherichia coli*, and has been modified so that it can aerobically utilize ethanol.

(18) The method as described above, wherein the L-amino acid is L-lysine.

(19) The method as described above, wherein activity or activities of one or more kinds of enzymes selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyldiaminopimelate deacylase are enhanced, and/or activity of lysine decarboxylase is attenuated.

DETAILED DESCRIPTION OF EXEMPLARY EMBODIMENTS

Bacterium

Figure 1:
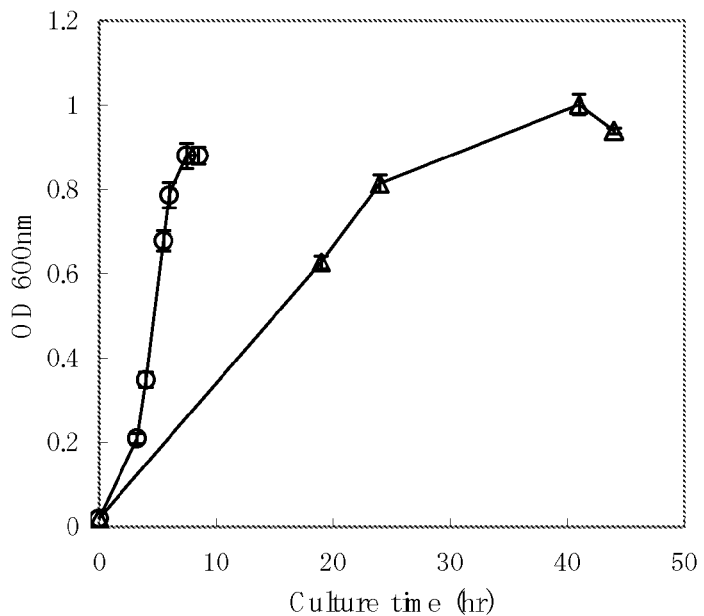
FIG. 1 shows growth of *Escherichia coli* in a minimal medium containing glucose (O) or oleic acid (Δ) as a carbon source.

The bacterium used herein is a bacterium which belongs to the family Enterobacteriaceae and has an L-amino acid-producing ability. According to one embodiment, the bacterium belongs to the family Enterobacteriaceae, has an L-amino acid-producing ability, and has been modified so that intracellular hydrogen peroxide concentration of the bacterium is reduced.

The L-amino acid-producing ability refers to an ability of the bacterium used to produce and accumulate an L-amino acid in a medium or the cells, when the bacterium is cultured in the medium. It can mean an ability to accumulate a target L-amino acid in the medium in an amount not less than 0.5 g/L, or not less than 1.0 g/L. The bacterium having an L-amino acid-producing ability can be a bacterium inherently having an L-amino acid-producing ability, or can be a bacterium obtained by modifying such a bacterium as described herein, so that it has an L-amino acid-producing ability using a mutagenesis method or a recombinant DNA method.

Although the type of the L-amino acid is not particularly limited, examples thereof include: basic amino acids such as L-lysine, L-ornithine, L-arginine, L-histidine and L-citrulline; aliphatic amino acids such as L-isoleucine, L-alanine, L-valine, L-leucine and glycine; amino acids which are hydroxy-monoaminocarboxylic acids, such as L-threonine and L-serine; cyclic amino acids such as L-proline; aromatic amino acids such as L-phenylalanine, L-tyrosine and L-tryptophan; sulfur-containing amino acids such as L-cysteine, L-cystine, and L-methionine; acidic amino acids such as L-glutamic acid and L-aspartic acid; and amino acids having an amide group in the side chain, such as L-glutamine and L-asparagine. The bacterium can have the ability to produce two or more kinds of amino acids.

In this disclosure, the "L-amino acid" includes the L-amino acid in a free form and salts thereof, such as sulfate salt, hydrochloride salt, and carbonate salt. The "L-amino acid" also includes glycine, unless otherwise indicated.

Although the bacteria belonging to the family Enterobacteriaceae used for obtaining the bacterium are not particularly limited, they include bacteria belonging to the genera of *Escherichia, Enterobacter, Erwinia, Klebsiella, Pantoea, Photorhabdus, Providencia, Salmonella, Serratia, Shigella, Morganella, Yersinia*, and so forth. In particular, bacteria classified into the family Enterobacteriaceae according to the taxonomy used by the NCBI (National Center for Biotechnology Information) database (www.ncbi.nlm.nih.gov/Taxonomy/Browser/wwwtax.cgi?id=91347), are examples.

A bacterium which belongs to the genus *Escherichia* means that the bacterium is classified into the genus *Escherichia* according to classification known to a person skilled in the art of microbiology, although the bacterium is not particularly limited. Examples thereof include, for example, the bacteria of the phylesis described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples thereof include *Escherichia coli* W3110 (ATCC 27325), *Escherichia coli* MG1655 (ATCC 47076), and so forth, which are derived from the prototype wild-type strain, K12 strain.

These strains are available from, for example, American Type Culture Collection (Address: P.O. Box 1549 Manassas, Va. 20108, U.S.A.). That is, registration numbers are given to each of the strains, and the strains can be ordered by using these numbers. The registration numbers of the strains are listed in the catalogue of the American Type Culture Collection. The same shall apply to the strains mentioned below with registration numbers of ATCC.

A bacterium which belongs to the genus *Pantoea* means that the bacterium is classified into the genus *Pantoea* according to classification known to a person skilled in the art of microbiology. Some of *Enterobacter agglomerans* have been recently re-classified into *Pantoea agglomerans, Pantoea ananatis, Pantoea stewartii*, or the like, on the basis of the nucleotide sequence analysis of 16S rRNA etc. (Int. J. Syst. Bacteriol., 43, 162-173 (1993)). Herein, bacteria belonging to the genus *Pantoea* can encompass such bacteria re-classified into the genus *Pantoea* as described above.

As *Pantoea ananatis*, the *Pantoea ananatis* AJ13355 strain (FERM BP-6614), AJ13356 strain (FERM BP-6615), AJ13601 strain (FERM BP-7207), and derivatives thereof can be used. These strains were identified as *Enterobacter agglomerans* when they were isolated, and deposited as *Enterobacter agglomerans*. However, they were re-classified into *Pantoea* ananatis on the basis of nucleotide sequence analysis of 16S rRNA etc. as described above.

An *Enterobacter* bacterium means that the bacterium is classified into the genus *Enterobacter* according to classification known to a person skilled in the art of microbiology, although the bacterium is not particularly limited. Examples thereof include *Enterobacter agglomerans, Enterobacter aerogenes*, and the like. Specifically, the strains exemplified in European Patent Application Laid-open (EP-A) No. 952221 can be used. Examples of typical strains of the genus *Enterobacter* include the *Enterobacter agglomerans* ATCC 12287 strain, *Enterobacter aerogenes* ATCC 13048 strain, *Enterobacter aerogenes* NBRC 12010 strain (Biotechnol Bioeng., 2007, Mar. 27; 98(2):340-348), *Enterobacter aerogenes* AJ110637 (FERM ABP-10955) strain, and so forth.

L-Amino Acid-Producing Bacteria and Impartation or Enhancement of L-Amino Acid-Producing Ability Hereafter, L-Amino acid-producing bacteria belonging to the family Enterobacteriaceae, and methods for imparting an L-amino acid-producing ability to bacteria or methods for enhancing an L-amino acid-producing ability of bacteria, are described.

To impart an L-amino acid-producing ability, methods conventionally employed in the breeding of amino acid-producing strains of *Escherichia* bacteria, and so forth (see "Amino Acid Fermentation", Gakkai Shuppan Center (Ltd.), 1st Edition, published May 30, 1986, pp. 77-100), can be used. Such methods include acquiring an auxotrophic mutant strain, an L-amino acid analogue-resistant strain, or a metabolic regulation mutant strain, or constructing a recombinant strain in which an L-amino acid biosynthetic enzyme is overexpressed. In the breeding of L-amino acid-producing bacteria, the above-described property(s), such as auxotrophy, analogue resistance, and metabolic regulation mutation, can be imparted alone or in combinations of two, three, or more thereof. Expression of L-amino acid biosynthetic enzyme(s) can be enhanced alone or in combinations of two, three, or more thereof. Furthermore, imparting such properties as auxotrophy, analogue resistance, and metabolic regulation mutation can be combined with enhancing a biosynthetic enzyme.

An auxotrophic mutant strain, L-amino acid analogue-resistant strain, or metabolic regulation mutant strain, having an L-amino acid-producing ability can be obtained by subjecting a parent strain or wild-type strain to conventional mutagenesis, such as exposure to X-rays or UV irradiation or a treatment with a mutagen such as N-methyl-N'-nitro-N-nitrosoguanidine, and then selecting a strain exhibiting autotrophy, analogue resistance, or a metabolic regulation mutation, and having an L-amino acid-producing ability from the obtained mutant strains.

Moreover, the L-amino acid-producing ability can also be imparted or enhanced by increasing an enzymatic activity by gene recombination. Enhancement of an enzymatic activity can be attained by, for example, modifying a bacterium so that expression of a gene coding for an enzyme involved in the biosynthesis of an L-amino acid is enhanced. Expression of a gene can also be increased by introducing an amplification plasmid prepared by introducing a DNA fragment containing the gene into an appropriate plasmid, for example, a plasmid vector containing at least a gene responsible for replication and proliferation of the plasmid in microorganisms, increasing the copy number of the gene on a chromosome by conjugation, transfer, or the like, or introducing a mutation into the promoter region of the gene (refer to WO95/34672).

When an objective gene is introduced into the aforementioned amplification plasmid or chromosome, any promoter can be used to express the gene so long as the chosen promoter functions in Enterobacteriaceae bacteria. The promoter can be a native promoter for the gene, or a modified promoter. Expression amount of a gene can also be controlled by suitably choosing a promoter that strongly functions in Enterobacteriaceae bacteria, or by making the −35 and −10 regions of the promoter closer to the consensus sequence. These methods for enhancing expression of enzyme genes are described in WO00/18935, EP 1010755 A, and so forth.

Methods for imparting an L-amino acid-producing ability to bacteria and bacteria imparted with L-amino acid-producing ability are exemplified below.

L-Lysine-Producing Bacteria

Examples of L-lysine-producing bacteria of *Escherichia coli* include mutants having resistance to an L-lysine analogue. L-Lysine analogues inhibit growth of *Escherichia coli*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting *Escherichia coli* to a conventional artificial mutagenesis treatment. Specific examples of bacterial strains useful for producing L-lysine include *Escherichia coli* AJ11442 (FERM BP-1543, NRRL B-12185, see U.S. Pat. No. 4,346,170) and *Escherichia coli* VL611. In these microorganisms, feedback inhibition of aspartokinase by L-lysine is desensitized.

The WC1-96 strain can be used as an L-lysine-producing bacterium of *Escherichia coli*. This bacterial strain was bred from the W3110 strain, which was derived from *Escherichia coli* K-12, by replacing the wild-type lysC gene on the chromosome of the W3110 strain with a mutant lysC gene encoding a mutant aspartokinase III in which threonine at position 352 had been replaced with isoleucine, resulting in desensitization of feedback inhibition by L-lysine (U.S. Pat. No. 5,661,012), and then imparting AEC resistance to the resulting strain (U.S. Pat. No. 5,827,698). This strain was designated *Escherichia coli* AJ13069 and was deposited at the National Institute of Bioscience and Human-Technology, Agency of Industrial Science and Technology (currently, independent administrative agency, National Institute of Advanced Industrial Science and Technology, International Patent Organism Depositary, Central 6, 1-1, Higashi 1-Chome, Tsukuba-shi, Ibaraki-ken, 305-8566, Japan) on Dec. 6, 1994 and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

Examples of L-lysine-producing bacteria and parent strains for deriving them also include strains in which expression of one or more genes encoding an L-lysine biosynthetic enzyme is increased. Examples of such genes include, but are not limited to, dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (U.S. Pat. No. 6,040,160), phosphoenolpyruvate carboxylase gene (ppc), aspartate semialdehyde dehydrogenase gene (asd), diaminopimelate epimerase (dapF), tetrahydrodipicolinate succinylase (dapD), succinyl diaminopimelate deacylase (dapE), and aspartase gene (aspA) (EP 1253195 A). Among these enzymes, dihydrodipicolinate reductase, diaminopimelate decarboxylase, diaminopimelate dehydrogenase, phosphoenolpyrvate carboxylase, aspartate aminotransferase, diaminopimelate epimerase, aspartate semialdehyde dehydrogenase, tetrahydrodipicolinate succinylase, and succinyl diaminopimelate deacylase are particular examples. In addition, the parent strains may have an increased level of expression of the gene involved in energy efficiency (cyo) (EP 1170376A), the gene encoding nicotinamide nucleotide transhydrogenase (pntAB) (U.S. Pat. No. 5,830,716), the ybjE gene (WO2005/073390), or combinations thereof. Abbreviations of the genes are indicated in the parentheses.

It is known that the wild-type dihydrodipicolinate synthase derived from *Escherichia coli* suffers from feedback inhibition by L-lysine, and the wild-type aspartokinase derived from *Escherichia coli* suffers from expression suppression and feedback inhibition by L-lysine. Therefore, when the dapA and lysC genes are used, these genes can be mutant genes that do not suffer from the feedback inhibition by L-lysine.

Examples of DNA encoding a mutant dihydrodipicolinate synthase desensitized to feedback inhibition by L-lysine include a DNA encoding a protein that has the amino acid sequence in which the histidine residue at the position 118 is replaced by tyrosine residue. Examples of DNA encoding a mutant aspartokinase desensitized to feedback inhibition by L-lysine include a DNA encoding an AKIII having the amino acid sequence in which the threonine residue at the position 352, the glycine residue at the position 323, and the methionine residue at the position 318 are replaced by isoleucine, asparagine, and isoleucine residues, respectively (for these mutants, see U.S. Pat. Nos. 5,661,012 and 6,040,160). Such mutant DNAs can be obtained by site-specific mutagenesis using PCR or the like.

Wide host-range plasmids RSFD80, pCAB 1, and pCABD2 are known as plasmids containing a mutant dapA gene encoding a mutant dihydrodipicolinate synthase and a mutant lysC gene encoding a mutant aspartokinase (U.S. Pat. No. 6,040,160). *Escherichia coli* JM109 strain transformed with RSFD80 was named AJ12396 (U.S. Pat. No. 6,040,160), the strain was deposited at the National Institute of Bioscience and Human-Technology, Agency of Industrial Science and Technology, Ministry of International Trade and Industry (currently, independent administrative agency, National Institute of Advanced Industrial Science and Technology, International Patent Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a known method.

Examples of L-lysine-producing bacteria and parent strains for deriving them also include strains in which the activity of an enzyme that catalyzes a reaction that generates a compound other than L-lysine, by branching away from the biosynthetic pathway of L-lysine, is decreased or eliminated. Examples of the enzymes that catalyze a reaction for generating a compound other than L-lysine by branching away from the biosynthetic pathway of L-lysine include homoserine dehydrogenase, lysine decarboxylase (U.S. Pat. No. 5,827,698), and the malic enzyme (WO2005/010175). In order to decrease or eliminate the lysine decarboxylase activity, it is possible to reduce expression of both the cadA gene and ldcC gene coding for lysine decarboxylase (International Patent Publication WO2006/038695).

Examples of the strain in which cadA gene and ldcC gene are disrupted include the *Escherichia coli* WC196LC strain (WC196ΔcadAΔldc) (U.S. Pat. No. 5,827,698, U.S. Patent Application Pub. No. 2006/0160191). The WC196LC strain, which was designated AJ110692, was deposited at National Institute of Advanced Industrial Science and Technology, International Patent Organism Depositary (Central 6, 1-1, Higashi 1-Chome, Tsukuba-shi, Ibaraki-ken, 305-8566, Japan) on Oct. 7, 2008 as an international deposit, and assigned an accession number of FERM BP-11027.

L-Threonine-Producing Bacteria

Examples of L-threonine-producing bacteria and parent strains for deriving them include, but are not limited to, *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and so forth.

The TDH-6 strain is deficient in the thrC gene, as well as having sucrose-utilizing ability, and the ilvA gene thereof has a leaky mutation. This strain also has a mutation in the rhtA gene, which imparts resistance to high concentrations of threonine or homoserine. The B-3996 strain harbors the plasmid pVIC40 obtained by inserting a thrA*BC operon containing a mutant thrA gene into an RSF1010-derived vector. This mutant thrA gene encodes aspartokinase homoserine dehydrogenase I which is substantially desensitized to feedback inhibition by threonine. The B-3996 strain was deposited on Nov. 19, 1987, at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM) on Apr. 7, 1987 under the accession number VKPM B-3996.

*E. coli* VKPM B-5318 (EP 0593792 B) can also be used as an L-threonine-producing bacterium or a parent strain for deriving it. The B-5318 strain is prototrophic with regard to isoleucine, and in this strain, the regulatory region of the threonine operon in the plasmid pVIC40 is replaced with a temperature-sensitive λ-phage C1 repressor and PR promoter. The strain VKPM B-5318 was deposited at the Russian National Collection of Industrial Microorganisms (VKPM) (1 Dorozhny proezd., 1 Moscow 117545, Russia) on May 3, 1990, under the accession number of VKPM B-5318.

The bacterium used herein can be additionally modified to increase expression of one or more of the following genes:
the mutant thrA gene which codes for aspartokinase-homoserine dehydrogenase I resistant to feed back inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase).

The thrA gene which encodes aspartokinase-homoserine dehydrogenase I of *Escherichia coli* has been elucidated (nucleotide numbers 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide numbers 3734 to 5020, GenBank accession NC_000913.2, gi: 49175990). The thrC gene is located between the thrB gene and the yaaX open reading frame on the chromosome of *E. coli* K-12. All three of these genes function as a single threonine operon. To increase expression of the threonine operon, the attenuator region which affects the transcription can be removed from the operon (WO2005/049808, WO2003/097839).

The mutant thrA gene, which codes for aspartokinase-homoserine dehydrogenase I resistant to feedback inhibition by threonine, the thrB and thrC genes can be obtained as one operon from the well-known plasmid pVIC40 which is present in the threonine-producing *E. coli* strain VKPM B-3996. The plasmid pVIC40 is described in detail in U.S. Pat. No. 5,705,371.

The rhtA gene is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated rhtA gene (rht: resistance to homoserine and threonine). It has also been revealed that the rhtA23 mutation is an A-for-G substitution at position −1 with respect to the ATG start codon (ABSTRACTS of the 17th International Congress of Biochemistry and Molecular Biology in conjunction with Annual Meeting of the American Society for Biochemistry and Molecular Biology, San Francisco, Calif. Aug. 24-29, 1997, abstract No. 457; EP 1013765 A).

The asd gene of *E. coli* has already been elucidated (nucleotide numbers 3572511 to 3571408, GenBank accession NC_000913.1, gi:16131307), and can be obtained by PCR (refer to White, T. J., Arnheim, N., Erlich, H. A., 1989, Trends Genet, 5:185-189) utilizing primers prepared on the basis of the nucleotide sequence of the gene. The asd genes of other microorganisms can also be obtained in a similar manner.

The aspC gene coding for aspartate aminotransferase of *E. coli* has also already been elucidated (nucleotide numbers 983742 to 984932, GenBank accession NC_000913.1, gi:16128895), and can be obtained by PCR. The aspC genes of other microorganisms can also be obtained in a similar manner.

L-Cysteine-Producing Bacteria

Examples of L-cysteine-producing bacteria and parent strains deriving them include, but are not limited to, *E. coli* JM15 which is transformed with different cysE alleles encoding feedback inhibition-resistant serine acetyltransferases (U.S. Pat. No. 6,218,168, Russian Patent Application No. 2003121601), *E. coli* W3110 with overexpressed genes encoding proteins suitable for excretion of substances toxic to the cells (U.S. Pat. No. 5,972,663), *E. coli* strains with reduced cysteine desulfhydrase activity (Japanese Patent Laid-open No. 11-155571), *E. coli* W3110 with increased activity of a positive transcriptional regulator for cysteine regulon encoded by the cysB gene (WO01/27307A1), and so forth.

L-Leucine-Producing Bacteria

Examples of L-leucine-producing bacteria and parent strains for deriving them include, but are not limited to, *E. coli* strains resistant to leucine (for example, the 57 strain (VKPM B-7386, U.S. Pat. No. 6,124,121)) or *E. coli* strains resistant to an leucine analogue such as β-2-thienylalanine, 3-hydroxyleucine, 4-azaleucine, and 5,5,5-trifluoroleucine (Japanese Patent Publication (Kokoku) No. 62-34397 and Japanese Patent Laid-open No. 8-70879); *E. coli* strains obtained by a gene engineering technique described in WO96/06926; *E. coli* H-9068 (Japanese Patent Laid-open No. 8-70879), and so forth.

The bacterium used herein can be improved by enhancing expression of one or more genes involved in the L-leucine biosynthesis. Examples of such genes include the genes of the leuABCD operon, a typical example of which is a mutant leuA gene coding for isopropyl malate synthase desensitized to feedback inhibition by L-leucine (U.S. Pat. No. 6,403,342). In addition, the bacterium used herein can be improved by increasing expression of one or more genes coding for proteins which excrete L-amino acid from the bacterial cells. Examples of such genes include the b2682 and b2683 genes (ygaZH genes) (EP 1239041 A2).

L-Histidine-Producing Bacteria

Examples of L-histidine-producing bacteria and parent strains for deriving them include, but are not limited to: *E. coli* strain 24 (VKPM B-5945, RU 2003677); *E. coli* strain 80 (VKPM B-7270, RU 2119536); *E. coli* NRRL B-12116 to B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP 1085087); *E. coli* AI80/pFM201 (U.S. Pat. No. 6,258,554); and so forth.

Examples of L-histidine-producing bacteria and parent strains for deriving them also include strains in which expression of one or more genes encoding an L-histidine biosynthetic enzyme is increased. Examples of such genes include ATP phosphoribosyl transferase gene (hisG), phosphoribosyl AMP cyclohydrolase gene (hisI), phosphoribosyl-ATP pyrophosphohydrolase gene (hisI), phosphoribosylformimino-5-aminoimidazole carboxamide ribotide isomerase gene (hisA), amidotransferase gene (hisH), histidinol phosphate aminotransferase gene (hisC), histidinol phosphatase gene (hisB), histidinol dehydrogenase gene (hisD), and so forth.

It is known that the L-histidine biosynthetic enzymes encoded by hisG and hisBHAFI are inhibited by L-histidine, and therefore L-histidine-producing ability can be efficiently enhanced by introducing a mutation which imparts resistance to feedback inhibition into the ATP phosphoribosyl transferase gene (hisG) (Russian Patent Nos. 2003677 and 2119536).

Specific examples of strains having L-histidine-producing ability include *E. coli* FERM-P 5038 and 5048 which are introduced with a vector carrying a DNA encoding an L-histidine biosynthetic enzyme (Japanese Patent Laid-open No. 56-005099), *E. coli* strains introduced with a gene for amino acid transport (EP 1016710A), *E. coli* 80 strain imparted with sulfaguanidine, DL-1,2,4-triazole-3-alanine, and streptomycin resistance (VKPM B-7270, Russian Patent No. 2119536), and so forth.

L-Glutamic Acid-Producing Bacteria

Examples of L-glutamic acid-producing bacteria and parent strains for deriving them include, but are not limited to, *E. coli* VL334thrC+(EP 1172433), and so forth. *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* K12 strain (VKPM B-7) cells. As a result, an L-isoleucine auxotrophic L-glutamic acid-producing strain VL334thrC+(VKPM B-8961) was obtained.

Examples of L-glutamic acid-producing bacteria and parent strains for deriving them include, but are not limited to, strains in which expression of one or more genes encoding an L-glutamic acid biosynthetic enzyme is increased. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains modified to increase expression of the citrate synthetase gene, the phosphoenolpyruvate carboxylase gene, and/or the glutamate dehydrogenase gene include those disclosed in EP 1078989 A, EP 955368 A, and EP 952221 A.

Examples of L-glutamic acid-producing bacteria and parent strains for deriving them also include strains in which the activity of an enzyme that catalyzes synthesis of a compound other than L-glutamic acid, by branching away from the L-glutamic acid biosynthesis pathway, is decreased or eliminated. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), γ-glutamyl transferase (ggt), γ-glutamylcysteine synthetase (gshA), γ-glutamylputrescine synthetase (ycjK), and so forth. *Escherichia coli* deficient in α-ketoglutarate dehydrogenase activity or having reduced α-ketoglutarate dehydrogenase activity, and methods for obtaining them, are described in U.S. Pat. Nos. 5,378,616 and 5,573,945.

Specific examples include the following:

*E. coli* W3110sucA::Km$^r$
*E. coli* AJ12624 (FERM BP-3853)
*E. coli* AJ12628 (FERM BP-3854)
*E. coli* AJ12949 (FERM BP-4881)

*E. coli* W3110sucA::Kmr is a strain obtained by disrupting the α-ketoglutarate dehydrogenase gene (hereinafter also referred to as "sucA gene") of *E. coli* W3110. This strain is completely deficient in α-ketoglutarate dehydrogenase.

Other examples of L-glutamic acid-producing bacteria include *Escherichia coli* having resistance to an aspartic acid antimetabolite. Such a strain can also be deficient in α-ketoglutarate dehydrogenase, and examples thereof include, for example, *E. coli* AJ 13199 (FERM BP-5807, U.S. Pat. No. 5,908,768), FFRM P-12379, which additionally has a lowered L-glutamic acid-decomposing ability (U.S. Pat. No. 5,393,671), AJ13138 (FERM BP-5565, U.S. Pat. No. 6,110, 714), and so forth.

Examples of L-glutamic acid-producing bacteria of *Pantoea ananatis* include the *Pantoea ananatis* AJ13355 strain. This strain was isolated from soil in Iwata-shi, Shizuoka-ken, and was identified as being able to proliferate in a medium containing L-glutamic acid and a carbon source at a low pH. The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998, and assigned an accession number of FERM P-16644. It was then converted to an international deposit under the provisions of Budapest Treaty on Jan. 11, 1999 and assigned an accession number of FERM BP-6614. This strain was originally identified as *Enterobacter agglomerans* when it was isolated, and deposited as *Enterobacter agglomerans* AJ13355. However, it was recently re-classified into *Pantoea ananatis* on the basis of nucleotide sequencing of 16S rRNA and so forth.

Furthermore, examples of L-glutamic acid-producing bacteria of *Pantoea ananatis* also include *Pantoea* bacteria deficient in α-ketoglutarate dehydrogenase (αKGDH) activity or having reduced αKGDH activity. Examples of such a strain include AJ13356 (U.S. Pat. No. 6,331,419), which was derived by deleting the αKGDH-E1 subunit gene (sucA) in AJ13355, and the SC17sucA strain (U.S. Pat. No. 6,596,517), which is a sucA gene-deficient strain derived from the SC17 strain selected from AJ13355 as a low phlegm-producing mutant strain. The AJ13356 strain was deposited at the National Institute of Bioscience and Human-Technology, Agency of Industrial Science and Technology (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. Although the AJ13355 and AJ13356 strains are deposited at the aforementioned depository as *Enterobacter agglomerans*, they are referred to as *Pantoea ananatis* in this specification. The SC17sucA strain was assigned a private number of AJ417, and deposited at the National Institute of Advanced Industrial Science and Technology, International Patent Organism Depositary on Feb. 26, 2004, under an accession number of FERM BP-08646.

Furthermore, examples of L-glutamic acid-producing bacteria of *Pantoea ananatis* also include SC17sucA/RSFCPG+ pSTVCB, AJ13601, NP106, and NA1 strains. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain was selected from the SC17sucA/RSFCPG+pSTVCB strain as a strain resistant to a high concentration of L-glutamic acid at a low pH. The NP106 strain was derived from the AJ13601 strain by eliminating the RSFCPG+ pSTVCB plasmid. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

L-Phenylalanine-Producing Bacteria

Examples of L-phenylalanine-producing bacteria and parent strains for deriving them include, but are not limited to, *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR 8903681), *E. coli* NRRL B-12141, NRRL B-12145, NRRL B-12146, NRRL B-12147 (U.S. Pat. No. 4,407,952), and so forth. As parent strains, *E. coli* K-12 [W3110 (tyrA)/pPHAB] (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) can also be used (EP 488424 B1). Furthermore, L-phenylalanine-producing bacteria of *Escherichia coli*, with an enhanced activity of the protein encoded by the yedA gene or the yddG gene, can also be used (U.S. Patent Published Application Nos. 2003/0148473 A1 and 2003/0157667 A1).

L-Tryptophan-Producing Bacteria

Examples of tryptophan-producing bacteria and parent strains for deriving them include, but are not limited to, *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180, 373), *E. coli* AGX17(pGX44) (NRRL B-12263) and AGX6 (pGX50)aroP (NRRL B-12264) deficient in tryptophanase (U.S. Pat. No. 4,371,614), *E. coli* AGX17/pGX50, pACKG4-pps of which phosphoenolpyruvate-producing ability is enhanced (WO97/08333, U.S. Pat. No. 6,319,696), and so forth. L-Tryptophan-producing bacteria of *Escherichia coli* with an enhanced activity of the protein encoded by the yedA gene or the yddG gene can also be used (U.S. Patent Application Pub. Nos. 2003/0148473 A1 and 2003/0157667 A1).

Examples of L-tryptophan-producing bacteria and parent strains for deriving them also include strains in which one or more activities of the enzymes selected from anthranilate synthase (trpE), phosphoglycerate dehydrogenase (serA), and tryptophan synthase (trpAB) are increased. The anthranilate synthase and phosphoglycerate dehydrogenase both suffer from feedback inhibition by L-tryptophan and L-serine, and therefore a mutation desensitizing them to the feedback inhibition can be introduced into these enzymes. Specific examples of strains having such a mutation include *E. coli* SV164 which harbors desensitized anthranilate synthase and a transformant strain obtained by introducing the plasmid pGH5 (WO94/08031), which contains a mutant serA gene encoding feedback inhibition-desensitized phosphoglycerate dehydrogenase, into the *E. coli* SV164.

Examples of L-tryptophan-producing bacteria and parent strains for deriving them also include strains into which the tryptophan operon, containing a gene encoding inhibition-desensitized anthranilate synthase, is introduced (Japanese Patent Laid-open Nos. 57-71397, 62-244382, U.S. Pat. No. 4,371,614). Moreover, L-tryptophan-producing ability can be imparted by increasing expression of a gene encoding tryptophan synthase (trpBA) in the tryptophan operon. The tryptophan synthase consists of α and β subunits encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of L-proline-producing bacteria and parent strains for deriving them include, but are not limited to, *E. coli* 702ilvA (VKPM B-8012), which is deficient in the ilvA gene and is able to produce L-proline (EP 1172433), and so forth.

The bacterium used herein can be improved by increasing expression of one or more genes involved in the L-proline biosynthesis. Examples of a gene for L-proline-producing bacteria include the proB gene coding for glutamate kinase desensitized to feedback inhibition by L-proline (DE 3127361). In addition, the bacterium used herein can be improved by increasing expression of one or more genes coding for proteins excreting L-amino acid from the bacterial cells. Examples of such genes include the b2682 and b2683 genes (ygaZH genes) (EP 1239041 A2).

Examples of *Escherichia coli* having L-proline-producing ability include the following *E. coli* strains: NRRL B-12403 and NRRL B-12404 (British Patent No. 2075056), VKPM B-8012 (Russian Patent Application No. 2000124295), plasmid mutants described in German Patent No. 3127361, plasmid mutants described by Bloom F. R. et al. (The 15th Miami winter symposium, 1983, p. 34), and so forth.

L-Arginine-Producing Bacteria

Examples of L-arginine-producing bacteria and parent strains for deriving them include, but are not limited to, *E. coli* strain 237 (VKPM B-7925) (U.S. Patent Application Pub. No. 2002/058315A1) and derivative strains thereof harboring a mutant N-acetylglutamate synthase (Russian Patent Application No. 2001112869), *E. coli* strain 382 (VKPM B-7926) (EP 1170358 A1), an arginine-producing strain into which argA gene encoding N-acetylglutamate synthetase is introduced (EP 1170361 A1), and so forth.

Examples of L-arginine-producing bacteria and parent strains for deriving them also include strains in which expression of one or more genes encoding an L-arginine biosynthetic enzyme is increased. Examples of such genes include N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

L-Valine-Producing Bacteria

Example of L-valine-producing bacteria and parent strains for deriving them include, but are not limited to, strains which have been modified to overexpress the ilvGMEDA operon (U.S. Pat. No. 5,998,178). The region required for attenuation in the ilvGMEDA operon can be removed so that expression of the operon is not attenuated by produced L-valine. Furthermore, the ilvA gene in the operon can be disrupted so that threonine deaminase activity is decreased.

Examples of L-valine-producing bacteria and parent strains for deriving them also include mutant strains having a mutation in amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 was deposited at the Russian National Collection of Industrial Microorganisms (VKPM) (1 Dorozhny Proezd, 1 Moscow 117545, Russia) on Jun. 24, 1988, under the accession number of VKPM B-4411.

Furthermore, mutant strains requiring lipoic acid for growth and/or lacking H+-ATPase (WO96/06926) can also be used as the parent strains.

L-Isoleucine-Producing Bacteria

Examples of L-isoleucine-producing bacteria and parent strains for deriving them include, but are not limited to, mutant strains having resistance to 6-dimethylaminopurine (Japanese Patent Laid-open No. 5-304969), mutant strains having resistance to an isoleucine analogue such as thiaisoleucine and isoleucine hydroxamate, and such mutant strains further having resistance to DL-ethionine and/or arginine hydroxamate (Japanese Patent Laid-open No. 5-130882). In addition, recombinant strains transformed with genes encoding proteins involved in the L-isoleucine biosynthesis, such as threonine deaminase and acetohydroxy acid synthase, can also be used as the parent strains (Japanese Patent Laid-open No. 2-458, FR 0356739, and U.S. Pat. No. 5,998,178).

L-Asparagine-Producing Bacteria

L-Asparagine is produced by transferring an amino group to aspartic acid (Boehlein, S. K., Richards, N. G. J., & Schuster, S. M. (1994a), J. Biol. Chem., 269, 7450-7457). Therefore, examples of L-asparagine-producing bacteria of *Escherichia coli* include L-aspartic acid-producing *Escherichia coli* strains in which asparagine synthetase is enhanced.

The ability of the bacterium used herein to utilize a fatty acid or an alcohol such as glycerol can be enhanced.

Fatty acid-utilizing ability can be enhanced by, for example, attenuating expression of the fadR gene or deleting this gene, or enhancing expression of a gene involved in the fatty acid utilization, such as fadI, fadJ, fadL, fadE, fadD, fadB, or fadA gene (WO2009/142286).

The glycerol-utilizing ability can be enhanced by attenuating expression of the glpR gene (European Patent No. 1715056), enhancing expression of a glycerol metabolism gene such as glpA, glpB, glpC, glpD, glpE, glpF, glpG, glpK, glpQ, glpT, glpX, tpiA, gldA, dhaK, dhaL, dhaM, dhaR, fsa and talC genes (EP 1715055 A), or enhancing expression of the glycerol dehydrogenase gene (gldA), dihydroxyacetone kinase gene (dhaKLM, dak), and fructose-6-phosphate aldolase gene (fsaB) (WO2008/102861).

The bacterium used herein can be a bacterium having an ethanol-utilizing ability. Such a strain can be a bacterium inherently having ethanol-utilizing ability, a recombinant strain to which ethanol-utilizing ability is imparted, or a mutant strain of which ethanol-utilizing ability is increased.

As for *Escherichia coli*, as an enzyme anaerobically generating ethanol, presence of AdhE, which has activities of acetaldehyde dehydrogenase and alcohol dehydrogenase reversibly catalyzing the reactions mentioned below, is known. The sequence of the adhE gene coding for AdhE of *Escherichia coli* is disclosed in WO2009/031565 and U.S. Patent Published Application No. 2009/068712.

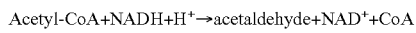

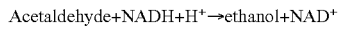

When ethanol is used as the carbon source, a particular example is to use a bacterium that can aerobically utilize ethanol. Although *Escherichia coli* usually cannot utilize ethanol under an aerobic condition, a strain modified so as to be able to aerobically utilize ethanol can be used. Examples of the method for modifying a bacterium that inherently cannot aerobically utilize ethanol, so as to be able to aerobically utilize ethanol, include making the bacterium harbor the adhE gene modified so as to be expressed under the control of a non-native promoter that functions under an aerobic condition, and making the bacterium harbor the adhE gene having a mutation that enables aerobic utilization of ethanol in the coding region (Clark D. P., and Cronan, J. E. Jr., 1980, J. Bacteriol., 144:179-184; Membrillo-Hernandez, J. et al., 2000, J. Biol. Chem., 275:33869-33875). Furthermore, this mutant adhE gene can be expressed under control of a non-native promoter that functions under an aerobic condition.

In *Escherichia coli*, if the promoter located upstream of the gene coding for alcohol dehydrogenase is replaced with a promoter that functions aerobically, alcohol dehydrogenase is expressed under an aerobic condition, and *Escherichia coli* becomes able to aerobically utilize ethanol (WO2008/010565). As the non-native promoter that functions under an aerobic condition, an arbitrary promoter that can express the adhE gene at a level exceeding a certain specific level under an aerobic condition can be used. The aerobic condition can be a condition typically used for culture of bacteria in which oxygen is supplied by a method such as shaking, aeration, stifling, or the like. Specifically, an arbitrary promoter that is known to express a gene under an aerobic condition can be used. For example, promoters of genes involved in the glycolysis, pentose phosphate pathway, TCA cycle, amino acid biosynthesis pathways, and so forth, can be used. Furthermore, it is known that the Ptac promoter of λ phage, lac promoter, trp promoter, trc promoter, PR promoters, and PL promoter are all strong promoters that function under an aerobic condition and are particular examples.

As a mutant AdhE having such a mutation as mentioned above, specifically, the mutant AdhE of *Escherichia coli* in which the glutamic acid residue at position 568 is replaced with an amino acid residue other than glutamic acid and aspartic acid residues, e.g., lysine residue, is known (Glu568Lys, E568K, WO2008/010565).

The aforementioned mutant AdhE can further include the following additional mutation(s).

A) Replacement of the glutamic acid residue at position 560 with another amino acid residue such as lysine residue, B) Replacement of the phenylalanine residue at position 566 with another amino acid residue such as valine residue, C) Replacement of the glutamic acid residue at position 22, methionine residue at position 236, tyrosine residue at position 461, isoleucine residue at position 544, and alanine residue at position 786, with other amino acid residues such as glycine residue, valine residue, cysteine residue, serine residue, and valine residue, respectively, or D) a combination of the aforementioned mutations.

The expression "a bacterium can aerobically utilize ethanol" means that the bacterium can grow in a minimum liquid medium or solid medium containing ethanol as the sole carbon source under an aerobic condition. The "aerobic condition" can be a condition usually used for culture of bacteria in which oxygen is supplied by a method such as shaking, aeration, stifling, or the like, as mentioned above. The expression "a bacterium can aerobically utilize ethanol" also means that, as for the level of the AdhE protein, the activity of alcohol dehydrogenase in a cell-free extract measured according to the method of Clark and Cronan (J. Bacteriol., 1980, 141, 177-183) is 1.5 units or higher, 5 units or higher, or 10 units or higher, per mg of the protein.

In particular, when ethanol is used as the carbon source, the bacterium used herein may be modified so that the activity of ribonuclease G is reduced.

The bacterium used herein can be a strain modified so that the activity of pyruvate synthase or pyruvate:NADP+ oxidoreductase is increased. The pyruvate synthase or pyruvate:NADP+ oxidoreductase activity can be increased as compared to that of the parent strain, for example, a wild type strain or a non-modified strain. In addition, when the microorganism does not originally have the pyruvate synthase activity, the microorganism which has been modified so that it has the pyruvate synthase activity has increased pyruvate synthase or pyruvate:NADP+ oxidoreductase activity as compared to a non-modified strain.

The "pyruvate synthase" referred to herein means an enzyme reversibly catalyzing the following reaction, which generates pyruvic acid from acetyl-CoA and $CO_2$, in the presence of an electron donor such as ferredoxin or flavodoxin (EC 1.2.7.1). Pyruvate synthase can be abbreviated as PS, and can be designated pyruvate oxidoreductase, pyruvate ferredoxin oxidoreductase, pyruvate flavodoxin oxidoreductase, or pyruvate oxidoreductase. As the electron donor, ferredoxin or flavodoxin can be used.

Reduced ferredoxin+acetyl-CoA+$CO_2$→oxidized ferredoxin+pyruvic acid+CoA

Enhancement of the pyruvate synthase activity can be confirmed by preparing crude enzyme solutions from the microorganism before the enhancement and the microorganism after the enhancement, and comparing the pyruvate synthase activities of them. The activity of pyruvate synthase can be measured by, for example, the method of Yoon et al. (Yoon, K. S. et al., Arch. Microbiol. 167:275-279, 1997). For example, the measurement can be attained by adding pyruvic acid to a reaction solution containing oxidized methylviologen as an electron acceptor, CoA, and a crude enzyme solution, and spectroscopically measuring the amount of reduced methylviologen, which increases due to the decarboxylation reaction of pyruvic acid. One unit (U) of the enzymatic activity is defined as an activity of reducing 1 μmol of methylviologen per 1 minute. When the parent strain has the pyruvate synthase activity, the activity increases, for example, 1.5 times or more, 2 times or more, or 3 times or more, as compared with that of the parent strain. When the parent strain does not have the pyruvate synthase activity, although it is sufficient that pyruvate synthase is produced due to the introduction of the pyruvate synthase gene, the activity can be enhanced to such an extent that the enzymatic activity can be measured, and the activity can be 0.001 U/mg (cell protein) or higher, 0.005 U/mg or higher, or 0.01 U/mg or higher. The pyruvate synthase is sensitive to oxygen, and expression of the activity and measurement of the activity are often difficult (Buckel, W. and Golding, B. T., 2006, Ann. Rev. of Microbiol., 60:27-49). Therefore, when the enzymatic activity is measured, the enzymatic reaction can be performed while reducing the oxygen concentration in the reaction vessel.

As the gene encoding pyruvate synthase, it is possible to use pyruvate synthase genes of bacteria having the reductive TCA cycle such as *Chlorobium tepidum* and *Hydrogenobacter thermophilus*. Moreover, it is also possible to use pyruvate synthase genes of bacteria belonging to the family Enterobacteriaceae including *Escherichia coli*. Furthermore, as the gene encoding pyruvate synthase, pyruvate synthase genes of autotrophic methanogens, such as *Methanococcus maripaludis*, *Methanocaldococcus jannaschii*, and *Methanothermobacter thermautotrophicus*, can be used.

Specific examples include a gene having the nucleotide sequence locating at the nucleotide numbers 1534432 to 1537989 of the genome sequence of *Chlorobium tepidum* (Genbank Accession No. NC_002932) and shown in SEQ ID NO: 1, as the pyruvate synthase gene of *Chlorobium tepidum*. The amino acid sequence encoded by this gene is disclosed as Genbank Accession No. AAC76906. Furthermore, it is known that the pyruvate synthase of *Hydrogenobacter thermophilus* forms a complex of four subunits, δ-subunit (Genbank Accession No. BAA95604), α-subunit (Genbank Accession No. BAA95605), β-subunit (Genbank Accession No. BAA95606) and γ-subunit (Genbank Accession No. BAA95607) (Ikeda, T. et al., 2006, Biochem. Biophys. Res. Commun., 340:76-82). Examples of the gene further include the pyruvate synthase gene consisting of four genes, HP1108, HP1109, HP1110 and HP1111, locating at the nucleotide numbers of 1170138 to 1173296 of the genome sequence of *Helicobacter pylori* (GenBank Accession No. NC 000915), and the pyruvate synthase gene consisting of four genes, SSO1208, SSO7412, SSO1207 and SSO1206, identified by the nucleotide numbers of 1047593 to 1044711 in the genome sequence of *Sulfolobus solfataricus* (GenBank Accession No. NC 002754). Furthermore, the pyruvate synthase gene may be those cloned from *Chlorobium, Desulfobacter, Aquifex, Hydrogenobacter, Thermoproteus, Pyrobaculum* bacteria or the like on the basis of homology to the genes exemplified above.

It is predicted that, in *Escherichia coli*, the ydbK gene (b1378) having the nucleotide sequence locating at the nucleotide numbers 1435284 to 1438808 in the genome sequence of the K-12 strain (GenBank Accession No. U00096) encodes pyruvate flavodoxin oxidoreductase, i.e., pyruvate synthase, on the basis of homology of the sequences. The amino acid sequence encoded by this gene is disclosed as GenBank Accession No. AAC76906. Furthermore, the pyruvate synthase gene can be any of pyruvate synthase genes of Enterobacteriaceae bacteria such as *Escherichia, Salmonella, Serratia, Enterobacter, Shigella*, and *Citrobacter* bacteria, which show high homology to the pyruvate synthase gene of *Escherichia coli* (ydbK).

The pyruvate synthase gene of *Methanococcus maripaludis* is encoded by the porCDABEF operon which locates at the nucleotide numbers 1462535 to 1466397 in the genome sequence of *Methanococcus maripaludis* (GenBank Accession No. NC_005791) (Hendrickson, E. L. et al., J. Bacteriol., 186: 6956-6969, 2004). This pyruvate synthase includes four subunits γ, α, β, and δ, and it has been known that PorE and PorF in addition to these subunits are important for pyruvate synthase activity (Lin, W. and Whitman, W. B., Arch. Microbiol., 181: 68-73, 2004). The γ subunit is encoded by the porA gene corresponding to the nucleotide numbers 1465867 to 1466397 (complementary strand) of the genome sequence, and the amino acid sequence encoded by this gene is disclosed as GenBank Accession No. NP_988626. The δ subunit is encoded by the porB gene corresponding to the nucleotide numbers 1465595 to 1465852 (complementary strand) of the genome sequence, and the amino acid sequence encoded by this gene is disclosed as GenBank Accession No. NP_988627. The α subunit is encoded by the porC gene corresponding to the nucleotide numbers 1464410 to 1465573 (complementary strand) of the genome sequence, and the amino acid sequence encoded by this gene is disclosed as GenBank Accession No. NP_988625. The β subunit is encoded by the porD gene corresponding to the nucleotide numbers 1463497 to 1464393 (complementary strand) of the genome sequence, and the amino acid sequence encoded by this gene is disclosed as GenBank Accession No. NP_988624. The PorE is encoded by the porE gene corresponding to the nucleotide numbers 1462970 to 1463473 (complementary strand) of the genome sequence, and the amino acid sequence encoded by this gene is disclosed as GenBank Accession No. NP_988623. The PorF is encoded by the porF gene corresponding to the nucleotide numbers 1462535 to 1462951 (complementary strand) of the genome sequence, and the amino acid sequence encoded by this gene is disclosed as GenBank Accession No. NP_988622.

It has been known that *Methanocaldococcus jannaschii, Methanothermobacter thermautotrophicus* and the like, which are autotrophic methanogenic archaebacteria, have a pyruvate synthase gene having the same structure, and therefore, these genes can be used.

The "pyruvate:NADP+ oxidoreductase" referred to herein is an enzyme reversibly catalyzing the following reaction, which generates pyruvic acid from acetyl CoA and CO2, in the presence of an electron donor such as NADPH or NADH (EC 1.2.1.15). The pyruvate:NADP+ oxidoreductase may be abbreviated as PNO, and may be designated pyruvate dehydrogenase. However, the "pyruvate dehydrogenase activity" referred to herein is the activity of catalyzing the oxidative decarboxylation of pyruvic acid to generate acetyl-CoA, as described later, and pyruvate dehydrogenase (PDH) which catalyses this reaction is an enzyme different from pyruvate: NADP+ oxidoreductase. Pyruvate:NADP+ oxidoreductase can use NADPH or NADH as the electron donor.

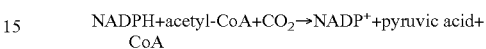

Enhancement of the pyruvate:NADP+ oxidoreductase activity can be confirmed by preparing crude enzyme solutions from the microorganism before the enhancement and the microorganism after the enhancement, and comparing the pyruvate:NADP+ oxidoreductase activities of them. The activity of pyruvate:NADP+ oxidoreductase can be measured by, for example, the method of Inui et al. (Inui, H. et al., J. Biol. Chem., 262:9130-9135, 1987). For example, the measurement can be attained by adding pyruvic acid to a reaction mixture containing oxidized methylviologen as an electron acceptor, CoA, and crude enzyme solution, and spectroscopically measuring amount of reduced methylviologen, which increases due to the decarboxylation of pyruvic acid. One unit (U) of the enzymatic activity is defined as an activity of reducing 1 μmol of methylviologen per 1 minute. When the parent strain has the pyruvate:NADP+ oxidoreductase activity, the activity increases, for example, 1.5 times or more, 2 times or more, or 3 times or more, compared with that of the parent strain. When the parent strain does not have the pyruvate:NADP+ oxidoreductase activity, although it is sufficient that pyruvate:NADP+ oxidoreductase is produced by the introduction of the pyruvate:NADP+ oxidoreductase gene, the activity can be enhanced to such an extent that the enzymatic activity can be measured, and the activity is 0.001 U/mg (cell protein) or higher, 0.005 U/mg or higher, or 0.01 U/mg or higher. Pyruvate:NADP+ oxidoreductase is sensitive to oxygen, and activity expression and measurement are often generally difficult (Inui, H. et al., 1987, J. Biol. Chem., 262: 9130-9135; Rotte, C. et al., 2001, Mol. Biol. Evol., 18:710-720).

As for the gene encoding pyruvate:NADP+ oxidoreductase, besides the pyruvate:NADP+ oxidoreductase gene of *Euglena gracilis*, which is a photosynthetic eukaryotic microorganism and is also classified into protozoans (Nakazawa et al., 2000, FEBS Lett., 479:155-156), and the pyruvate: NADP+ oxidoreductase gene of a protist, *Cryptosporidium parvum* (Rotte, C. et al., 2001, Mol. Biol. Evol., 18:710-720), it is known that a homologous gene also exists in *Bacillariophyta, Tharassiosira pseudonana* (Ctrnacta, V. et al., 2006, J. Eukaryot. Microbiol., 53:225-231).

Specifically, a gene having the nucleotide sequence disclosed as GenBank Accession No. AB021127 can be exemplified as the pyruvate:NADP+ oxidoreductase gene of *Euglena gracilis*. The amino acid sequence encoded by this gene is disclosed as GenBank Accession No. BAB12024.

The microorganism described herein may be a microorganism modified so that the pyruvate synthase activity is increased by such a modification that the activity of recycling oxidized electron donor to reduced electron donor, which is required for the pyruvate synthase activity, is increased compared with a parent strain, for example, a wild type strain or a non-modified strain. An example of the activity for recycling oxidized electron donor to reduced electron donor include ferredoxin NADP+ reductase activity. Furthermore, the microorganism may be a microorganism modified so that the activity of pyruvate synthase is increased by such a modification that pyruvate synthase activity is increased, in addition to the enhancement of the electron donor recycling activity. The aforementioned parent strain may be a strain inherently having a gene encoding the electron donor recycling activity, or a strain which does not inherently have the electron donor recycling activity, but can be imparted with the activity by introduction of a gene encoding the activity, and improve an L-amino acid-producing ability.

The "ferredoxin NADP+ reductase" means an enzyme that reversibly catalyzes the following reaction (EC 1.18.1.2).

Reduced ferredoxin+NADP$^+$→Oxidized ferredoxin+ NADPH+H$^+$

This reaction is a reversible reaction, and can generate the reduced ferredoxin in the presence of NADPH and the oxidized ferredoxin. Ferredoxin is replaceable with flavodoxin, and the enzyme has a function equivalent to that of the enzyme designated flavodoxin NADP+ reductase. Existence of ferredoxin NADP+ reductase is confirmed in a wide variety of organisms ranging from microorganisms to higher organisms (refer to Carrillo, N. and Ceccarelli, E. A., 2003, Eur. J. Biochem., 270:1900-1915; Ceccarelli, E. A. et al., 2004, Biochim. Biophys. Acta., 1698:155-165), and some of the enzymes are also named ferredoxin NADP+ oxidoreductase or NADPH-ferredoxin oxidoreductase.

Enhancement of the ferredoxin NADP+ reductase activity can be confirmed by preparing crude enzyme solutions from the microorganism before the modification and the microorganism after the modification, and comparing the ferredoxin NADP+ reductase activities of them. The activity of ferredoxin NADP+ reductase can be measured by, for example, the method of Blaschkowski et al. (Blaschkowski, H. P. et al., 1982, Eur. J. Biochem., 123:563-569). For example, the activity can be measured by using ferredoxin as a substrate to spectroscopically measure a decrease of the amount of NADPH. One unit (U) of the enzymatic activity is defined as activity for oxidizing 1 µmol of NADPH per 1 minute. When the parent strain has the ferredoxin NADP+ reductase activity, and the activity of the parent strain is sufficiently high, it is not necessary to enhance the activity. However, the enzymatic activity is increased 1.5 times or more, 2 times or more, or 3 times or more, compared with that of the parent strain.

Genes encoding the ferredoxin NADP+ reductase are found in many biological species, and any of them showing the activity in the objective L-amino acid-producing strain can be used. As for *Escherichia coli*, the fpr gene has been identified as a gene for flavodoxin NADP+ reductase (Bianchi, V. et al., 1993, 175:1590-1595). Moreover, it is known that, in *Pseudomonas putida*, an NADPH-putidaredoxin reductase gene and a putidaredoxin gene exist as an operon (Koga, H. et al., 1989, J. Biochem. (Tokyo), 106:831-836).

Examples of the flavodoxin NADP+ reductase gene of *Escherichia coli* include the fpr gene which locates at the nucleotide numbers 4111749 to 4112495 (complementary strand) of the genome sequence of the *Escherichia coli* K-12 strain (Genbank Accession No. U00096). The amino acid sequence of Fpr is the sequence encoded by the gene disclosed as Genbank Accession No. AAC76906. Moreover, a ferredoxin NADP+ reductase gene (Genbank Accession No. BAB99777) is also found at the nucleotide numbers 2526234 to 2527211 of the genome sequence of *Corynebacterium glutamicum* (Genbank Accession No. BA00036).

The pyruvate synthase activity requires presence of ferredoxin or flavodoxin as an electron donor. Therefore, the microorganism may be a microorganism modified so that the activity of pyruvate synthase is increased by such a modification that the production ability for ferredoxin or flavodoxin is improved.

Moreover, the microorganism may also be modified so that the production ability for ferredoxin or flavodoxin is improved, in addition to being modified so that pyruvate synthase activity or flavodoxin NADP+ reductase and pyruvate synthase activities are enhanced.

Herein, the "ferredoxin" refers to a protein containing non-heme iron atoms (Fe) and sulfur atoms, bound with an iron-sulfur cluster called 4Fe-4S, 3Fe-4S or 2Fe-2S cluster, and functioning as a one-electron carrier. The "flavodoxin" refers to a protein containing FMN (flavin-mononucleotide) as a prosthetic group and functioning as a one- or two-electron carrier. Ferredoxin and flavodoxin are described in the reference of McLean et al. (McLean K. J. et al., 2005, Biochem. Soc. Trans., 33:796-801).

The parent strains to be subjected to the modification may be strains which inherently have an endogenous gene encoding ferredoxin or flavodoxin. Alternatively, the parent strains may be strains which do not inherently have a gene encoding ferredoxin or flavodoxin, but which can produce these proteins by introduction of a ferredoxin or flavodoxin gene to show improved L-glutamic acid-producing ability.

Improvement of ferredoxin or flavodoxin-producing ability compared with the parent strain, such as a wild-type or non-modified strain, can be confirmed by, for example, comparing amount of mRNA for ferredoxin or flavodoxin with that of a wild type strain or non-modified strain. Examples of the method for confirming the expression amount include Northern hybridization and RT-PCR (Sambrook, J. Et al., 1989, Molecular Cloning A Laboratory Manual/Second Edition, Cold Spring Harbor Laboratory Press, New York.). Degree of the increase of the expression is not particularly limited, so long as it increases compared with that of a wild type strain or non-modified strain. However, it increases, for example, 1.5 times or more, 2 times or more, or 3 times or more, compared with that of a wild type strain or non-modified strain.

Improvement of the ferredoxin or flavodoxin-producing ability as compared to a parent strain, for example, a wild type or non-modified strain, can be detected by SDS-PAGE, two-dimensional electrophoresis, or Western blotting using antibodies (Sambrook J. et al., Molecular Cloning A Laboratory Manual/Second Edition, 1989, Cold Spring Harbor Laboratory Press, New York). Degree of the improvement of the production is not particularly limited so long as it increases compared with that of a wild type strain or non-modified strain. However, it increases, for example, 1.5 times or more, 2 times or more, or 3 times or more, compared with that of a wild type strain or non-modified strain.

The activities of ferredoxin and flavodoxin can be measured by adding them to a suitable oxidation-reduction reaction system. For example, a method including reducing produced ferredoxin with ferredoxin NADP+ reductase and quantifying reduction of cytochrome C by the produced reduced ferredoxin, is disclosed by Boyer et al. (Boyer, M. E. et al., 2006, Biotechnol. Bioeng., 94:128-138). Furthermore, the activity of flavodoxin can be measured by the same method using flavodoxin NADP+ reductase.

Genes encoding ferredoxin or flavodoxin are widely distributed, and any of those can be used so long as ferredoxin or flavodoxin encoded by the genes can be utilized by pyruvate synthase and an electron donor recycling system. For example, in *Escherichia coli*, the fdx gene exists as a gene encoding ferredoxin which has a 2Fe-2S cluster (Ta, D. T. and Vickery, L. E., 1992, J. Biol. Chem., 267:11120-11125), and the yfhL gene is expected as a gene encoding ferredoxin which has a 4Fe-4S cluster. Furthermore, as the flavodoxin gene, the fldA gene (Osborne C. et al., 1991, J. Bacteriol., 173:1729-1737) and the fldB gene (Gaudu, P. and Weiss, B., 2000, J. Bacteriol., 182:1788-1793) are known. In the genome sequence of *Corynebacterium glutamicum* (Genbank Accession No. BA00036), multiple ferredoxin genes, fdx (Genbank Accession No. BAB97942) were found at the nucleotide numbers of 562643 to 562963, and the fer gene was found at the nucleotide numbers of 1148953 to 1149270 (Genbank Accession No. BAB98495). Furthermore, in *Chlorobium tepidum*, many ferredoxin genes exist, and ferredoxin I and ferredoxin II have been identified as ferredoxin genes for the 4Fe-4S type which serves as the electron acceptor of pyruvate synthase (Yoon, K. S. et al., 2001, J. Biol. Chem., 276:44027-44036). Ferredoxin gene or flavodoxin gene of bacteria having the reductive TCA cycle such as the ferredoxin gene of *Hydrogenobacter thermophilus* and the like can also be used.

Specific examples of the ferredoxin gene of *Escherichia coli* include the fdx gene locating at the nucleotide numbers of 2654770 to 2655105 (complementary strand) of the genome sequence of the *Escherichia coli* K-12 strain (Genbank Accession No. U00096), and the yfhL gene locating at the nucleotide numbers of 2697685 to 2697945 of the same. The amino acid sequences of Fdx and YfhL are disclosed as Genbank Accession Nos. AAC75578 and AAC75615, respectively. Examples of the flavodoxin gene of *Escherichia coli* include the fldA gene locating at the nucleotide numbers of 710688 to 710158 (complementary strand) of the genome sequence of the *Escherichia coli* K-12 strain (Genbank Accession No. U00096), and the fldB gene locating at the nucleotide numbers 3037877 to 3038398 of the same. The amino acid sequences encoded by the fldA gene and the fldB gene are disclosed as Genbank Accession Nos. AAC73778 and AAC75933, respectively.

Examples of the ferredoxin gene of *Chlorobium tepidum* include the ferredoxin I gene locating at the nucleotide numbers of 1184078 to 1184266 in the genome sequence of *Chlorobium tepidum* (Genbank Accession No. NC_002932), and the ferredoxin II gene locating at the nucleotide numbers of 1184476 to 1184664 of the same. The amino acid sequences of Ferredoxin I and Ferredoxin II are disclosed as Genbank Accession Nos. AAM72491 and AAM72490, respectively. Examples further include the ferredoxin gene of *Hydrogenobacter thermophilus* (Genbank Accession No. BAE02673) and the ferredoxin gene of *Sulfolobus solfataricus* indicated with the nucleotide numbers of 2345414 to 2345728 in the genome of *Sulfolobus solfataricus*. Furthermore, the gene may be those cloned from *Chlorobium, Desulfobacter, Aquifex, Hydrogenobacter, Thermoproteus, Pyrobaculum* bacteria or the like on the basis of homology to the genes exemplified above, or those cloned from γ-proteobacteria, such as those of the genus *Enterobacter, Klebsiella, Serratia, Erwinia, Yersinia* or the like, coryneform bacteria such as *Corynebacterium glutamicum* and *Brevibacterium lactofermentum, Pseudomonas* bacteria such as *Pseudomonas aeruginosa, Mycobacterium* bacteria such as *Mycobacterium tuberculosis*, and so forth.

Furthermore, in the bacterium herein, malic enzyme activity can be decreased, in addition to enhancing pyruvate synthase activity or pyruvate:NADH+ oxidoreductase activity. Especially, it is a particular example that malic enzyme activity is reduced when the bacterium is one belonging to the genus *Escherichia, Enterobacter, Pantoea, Klebsiella,* or *Serattia*.

Herein, malic enzyme activity means an activity for reversibly catalyzing the reaction of oxidatively decarboxylating malic acid to produce pyruvic acid. The aforementioned reaction is catalyzed by two kinds of enzymes: NADP-dependent malic enzyme which uses NADP as an electron acceptor (also noted as "malate dehydrogenase (oxaloacetate-decarboxylating) (NADP+)" (EC:1.1.1.40 b2463 gene (also noted as maeB gene)); and NAD-dependent malic enzyme which uses NAD as an electron acceptor (also noted as "malate dehydrogenase (oxaloacetate-decarboxylating)(NAP+)" (EC:1.1.1.38 sfc gene (also noted as maeA gene). Malic enzyme activity can be measured by the method of Bologna et al. (Bologna, F. P. et al., 2007, J. Bacteriol., 2007 189: 5937-5946).

NADP-dependent malic enzyme: $NADP^+ +$ malate$\rightarrow NADPH+CO_2+$pyruvate

NAD-dependent malic enzyme: $NAD^+ +$ malate$\rightarrow NADH+CO_2+$pyruvate

Herein, activities of both of NADP-dependent malic enzyme and NAD-dependent malic enzyme can be decreased. It is a particular example that activities of both type of malic enzymes are decreased when the bacterium of the present invention is a bacterium belonging to the genus *Escherichia, Enterobacter, Pantoea, Klebsiella,* or *Serattia*.

Furthermore, in the microorganism herein, pyruvate dehydrogenase activity can be reduced, in addition to enhancing pyruvate synthase activity or pyruvate:NADH+ oxidoreductase activity.

Herein, pyruvate dehydrogenase (henceforth also referred to as "PDH") activity means an activity for catalyzing the reaction of oxidatively decarboxylating pyruvic acid to produce acetyl-CoA. The aforementioned reaction is catalyzed by three kinds of enzymes: PDH (E1p, pyruvate dehydrogenase, EC:1.2.4.1, encoded by aceE gene), dihydrolipoyl transacetylase (E2p, EC:2.3.1.12, encoded by aceF gene), and dihydrolipoamide dehydrogenase (E3, EC:1.8.1.4, encoded by lpdA gene). That is, these three kinds of subunits catalyze the following reactions, respectively, and the activity for catalyzing the reaction corresponding to the total of these three reactions is called PDH activity. As for confirmation of the PDH activity, the activity can be measured according to the method of Visser and Strating (Visser, J. and Strating, M., 1982, Methods Enzymol., 89:391-399).

E1p: Pyruvate+[dihydrolipoyllysine-residue succinyl-transferase]lipoyllysine->[dihydrolipoyllysine-residue acetyltransferase]S-acetyldihydrolipoyll-ysine+$CO_2$ E2p: CoA+enzyme N6-(S-acetyldihydrolipoyl) lysine$\rightarrow$acetyl-CoA+enzyme N6-(dihydrolipoyl) lysine E3: Protein N6-(dihydrolipoyl)lysine+$NAD^+\rightarrow$protein N6-(lipoyl)lysine+$NADH+H^+$ Furthermore, the bacterium may be strain modified so that maleate synthase-isocitrate lyase-isocitrate dehydrogenase kinase/phosphatase operon (ace operon) is constitutively expressed, or expression of this operon is enhanced. The expression that maleate synthase-isocitrate lyase-isocitrate dehydrogenase kinase/phosphatase operon is constitutively expressed means that the promoter of the ace operon is not suppressed by iclR, which is a repressor protein, or this suppression is released.

The constitutive expression of the ace operon, or enhancement of the expression of this operon, can be confirmed on the basis of increase of the enzymatic activities of maleate synthase (aceB), isocitrate lyase (aceA), and isocitrate dehydrogenase kinase/phosphatase (aceK), which are proteins encoded by the ace operon, as compared to those of a non-modified, wild type strain.

As for measurement of the enzymatic activities, for example, the maleate synthase activity can be measured by measuring glyoxylic acid-dependent decomposition of thioester bond of acetyl-CoA through measurement of reduction of A232 (Dixon, G. H., Kornberg, H. L., 1960, Biochem. J, 1, 41:217-233), the isocitrate lyase activity can be measured by measuring glyoxylic acid produced from isocitrate as a 2,4-dinitrophenylhydrazone derivative (Roche, T. E., Williams J. O., 1970, Biochim. Biophys. Acta, 22, 206(1):pp 193-195), and the isocitrate dehydrogenase kinase activity can be measured by measuring desorption of phosphate from isocitrate dehydrogenase using $^{32}P$ (Wang, J. Y. J., Koshland, D. E., Jr., 1982, Arch. Biochem. Biophys., 218, pp 59-67).

The suppression can be released by, for example, modifying the repressor (iclR)-binding site on the ace operon so that iclR cannot bind to the operon. The suppression can also be released by replacing the promoter of the operon with a potent promoter that does not suffer from suppression of expression by iclR (lac promoter, etc.).

Furthermore, expression of the ace operon can be made constitutive by modifying the bacterium so that expression of the iclR gene is reduced or eliminated. Specifically, by modifying an expression control sequence of the gene coding for iclR so that that gene is not expressed, or modifying the coding region of the repressor so that the function of the repressor is lost.

Method for Decreasing Intracellular Hydrogen Peroxide Concentration

An Enterobacteriaceae bacterium which has an L-amino acid-producing ability and has been modified so that intracellular hydrogen peroxide concentration is reduced, which is an embodiment of the bacterium described herein, can be obtained by modifying such an Enterobacteriaceae bacterium having an L-amino acid-producing ability as described above, so that intracellular hydrogen peroxide concentration thereof is reduced. The bacterium can also be obtained by imparting an L-amino acid-producing ability to a bacterium modified so that intracellular hydrogen peroxide concentration is reduced.

The expression that "intracellular hydrogen peroxide concentration is reduced" means both the case where concentration of hydrogen peroxide is relatively reduced as compared to that of a non-modified strain such as a parent or wild type strain, and the case where hydrogen peroxide does not substantially exist in the cell.

Such modification of a bacterium, in which intracellular hydrogen peroxide concentration is reduced, can be attained by, for example, enhancing expression of the oxyS gene, or increasing expression of electron transferring flavoprotein (ETF), or a combination of these.

The expression of ETF can be increased by, for example, enhancing expression of the fixABC operon.

The term "oxyS" means a gene coding for oxyS, which is a low molecular weight RNA abundantly expressed in Enterobacteriaceae bacteria. Specifically, as a gene coding for oxyS, a gene having the nucleotide sequence locating at the nucleotide numbers 4,156,308 to 4,156,417 in the genome sequence of *Escherichia coli* (GenBank Accession No. U00096), which is shown in SEQ ID NO: 9, can be exemplified as the oxyS gene of *Escherichia coli*.

The term "fixABC" used herein refers to a gene containing at least fixA, fixB, and fixC among the genes of the fixABCX operon. The fixX gene may be contained, or may not be contained. Specifically, as the fixA gene of *Escherichia coli*, a gene having the nucleotide sequence locating at the nucleotide numbers of 42403 to 43173 in the genome sequence of *Escherichia coli* (GenBank Accession No. U00096) and shown in SEQ ID NO: 10, can be exemplified. The amino acid sequence encoded by this gene is shown in SEQ ID NO: 11.

As the gene coding for fixB, there can be specifically exemplified a gene having the nucleotide sequence locating at the nucleotide numbers of 43188 to 44129 in the genome sequence of *Escherichia coli* (GenBank Accession No. U00096) and shown in SEQ ID NO: 12, as the fixB gene of *Escherichia coli*. The amino acid sequence encoded by this gene is shown in SEQ ID NO: 13.

As the gene coding for fixC, there can be specifically exemplified a gene having the nucleotide sequence locating at the nucleotide numbers of 44180 to 45466 in the genome sequence of *Escherichia coli* (GenBank Accession No. U00096) and shown in SEQ ID NO: 14, as the fixC gene of *Escherichia coli*. The amino acid sequence encoded by this gene is shown in SEQ ID NO: 15.

The term "sodA" means a gene coding for SodA utilizing manganese as a cofactor, which is one of the superoxide dismutases existing in Enterobacteriaceae bacteria. Specifically, as the gene coding for SodA, a gene having the nucleotide sequence locating at the nucleotide numbers 4,098,833 to 4,099,453 in the genome sequence of *Escherichia coli* (GenBank Accession No. U00096) and shown in SEQ ID NO: 16 can be exemplified as the sodA gene of *Escherichia coli*. The amino acid sequence encoded by this gene is shown in SEQ ID NO: 17.

RNA encoded by the oxyS gene and the proteins encoded by the fixA gene, fixB gene, and fixC gene may be homologues, artificially modified versions thereof, or the like, or RNA or proteins having conservative mutation(s), so long as intracellular hydrogen peroxide concentration is reduced when expression of such genes is enhanced.

Such homologues, artificially modified versions, RNAs, and proteins having conservative mutation(s) as described above are referred to as conservative variants.

Such a conservative variant of the protein encoded by the fixA, fixB, or fixC gene may be, for example, a protein having the amino acid sequence of SEQ ID NO: 11, 13 or 15, but including substitutions, deletions, insertions, additions, or the like of one or several amino acid residues at one or several positions.

Although the number meant by the term "one or several" can differ depending on the positions of amino acid residues in the three-dimensional structure of the protein or the types of amino acid residues, specifically, it is 1 to 20, 1 to 10, or 1 to 5. The conservative mutation is typically a conservative substitution. The conservative substitution is a mutation wherein substitution takes place mutually among Phe, Trp, and Tyr, if the substitution site is an aromatic amino acid; among Leu, Ile and Val, if the substitution site is a hydrophobic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having a hydroxyl group. Substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like can be a result of a naturally-occurring mutation due to an individual difference, difference of species, or the like, of a microorganism from which the genes are derived (mutant or variant). Such a protein can be obtained by, for example, modifying the nucleotide sequence of a wild-type fixA, fixB, or fixC gene by site-specific mutagenesis so that the amino acid residues at the specific sites of the encoded protein include substitutions, deletions, insertions, or additions of amino acid residues.

Furthermore, such a protein having a conservative mutation as described above can be a protein showing a homology of, for example, 80% or more, 90% or more, 95% or more, 97% or more, 98% or more, or 99% or more, to the entire amino acid sequence of corresponding wild-type protein, and having a function equivalent to that of the wild-type protein. In this specification, "homology" can mean "identity".

The wild-type fixA, fixB and fixC genes are not limited to the genes of Escherichia coli, Pantoea ananatis, Enterobacter aerogenes, and so forth, and they can be any of those in which arbitrary codon(s) is/are replaced with equivalent codon(s), so long as they codes for such amino acid sequences as described above.

The wild-type fixA, fixB and fixC genes can also be a DNA that is able to hybridize with a nucleotide sequence complementary to the nucleotide sequence of SEQ ID NO: 10, 12, 14, 16, or 18, or a probe that can be prepared from the complementary sequence under stringent conditions, and codes for a protein having a function equivalent to that of a protein having the amino acid sequence of SEQ ID NO: 11, 13 or 15. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, not less than 98% homologous, or not less than 99% homologous, hybridize to each other, and DNAs less homologous than the above do not hybridize to each other, or conditions of washing of typical Southern hybridization, i.e., conditions of washing once, 2 or 3 times, at a salt concentration and temperature corresponding to 1×SSC, 0.1% SDS at 60° C., or 0.1×SSC, 0.1% SDS at 60° C., or 0.1×SSC, 0.1% SDS at 68° C.

As the probe, a part of a sequence that is complementary to one of the genes can also be used. Such a probe can be prepared by PCR using oligonucleotides prepared on the basis of a known gene sequence as primers and a DNA fragment containing these nucleotide sequences as a template. For example, when a DNA fragment having a length of about 300 bp is used as the probe, the washing conditions of the hybridization can be, for example, 50° C., 2×SSC and 0.1% SDS.

The aforementioned descriptions concerning conservative variants of the aforementioned proteins and genes coding for them are similarly applied to the other genes mentioned below for the L-amino acid-producing bacteria.

Examples of conservative variant of RNA encoded by the oxyS gene include RNA that can hybridize with a sequence complementary to the sequence of SEQ ID NO: 1 or a probe that can be prepared from the complementary sequence under stringent conditions, and can reduce intracellular hydrogen peroxide concentration. The meaning of the "stringent conditions" is the same as that described above.

Furthermore, the conservative variant of RNA encoded by the oxyS gene may be RNA that shows a homology of, for example, 80% or more, 90% or more, 95% or more, 97% or more, 98% or more, 99% or more, to the entire nucleotide sequence, and can reduce intracellular hydrogen peroxide concentration.

Genes coding for such conservative variants of the RNA or proteins as described above are also the "conservative variants" of wild type genes.

Hereafter, the modification for reducing intracellular hydrogen peroxide concentration will be specifically explained. The enhancement of expression of the oxyS gene and the enhancement of expression of the fixABC genes can be performed in an arbitrary order.

Enhancement of Gene Expression

Methods for enhancing expression of a target gene will be explained below. These methods can also be applied to the genes described for the aforementioned L-amino acid-producing bacteria.

The first method is increasing copy number of a target gene. For example, copy number of the target gene can be increased by cloning the gene on an appropriate vector and transforming a host microorganism with the obtained vector.

The vector used for transformation may be a plasmid autonomously replicable in a cell of the host microorganism. Examples of the plasmid autonomously replicable in bacteria of the Enterobacteriaceae include plasmid vectors pUC19, pUC18, pBR322, RSF1010, pHSG299, pHSG298, pHSG399, pHSG398, pSTV28, pSTV29 (pHSG and pSTV vectors are available from Takara Bio Inc.), pMW119, pMW118, pMW219, pMW218 (pMW vectors are available from Nippon Gene Co., Ltd.) and so forth. In addition, a phage DNA may also be used as the vector instead of a plasmid.

Examples of transformation methods include treating recipient cells with calcium chloride so to increase permeability of the DNA, which has been reported for Escherichia coli K-12 (Mandel, M. and Higa, A., 1970, J. Mol. Biol., 53:159-162), the electric pulse method (Japanese Patent Laid-open No. 2-207791), and so forth.

Increasing the copy number of a target gene can also be achieved by introducing multiple copies of the gene into the chromosomal DNA of the microorganism. Introducing multiple copies of the gene into the chromosomal DNA of the microorganism may be performed by homologous recombination (MillerI, J. H. Experiments in Molecular Genetics, 1972, Cold Spring Harbor Laboratory) using a sequence whose multiple copies exist as targets in the chromosomal DNA. Sequences having multiple copies in the chromosomal DNA include, but are not limited to, repetitive DNA, and inverted repeats existing at the end of a transposable element. Also, as disclosed in Japanese Patent Laid-open No. 2-109985, it is possible to incorporate the target gene into a transposon, and allow it to be transferred to introduce multiple copies of the gene into the chromosomal DNA. Introduction of a target gene into a bacterial chromosome can be also achieved by the method using Mu phage (Japanese Patent Laid-open No. 2-109985), or the like. Transfer of a target gene to a chromosome can be confirmed by Southern hybridization using a part of the gene as a probe.

When copy number of a gene is increased, the copy number is not particularly limited so long as activity of the product of the target gene can be enhanced. However, when the microorganism originally has the target gene, the copy number can be 2 or more. When the microorganism does not originally have the gene of the present invention, the copy number of the gene introduced may be 1, but it may also be 2 or more.

The second method is enhancing expression of a target gene by replacing an expression regulatory sequence of the target gene such as promoter on the chromosomal DNA or plasmid with a promoter which has an appropriate strength. For example, the thr promoter, lac promoter, trp promoter, trc promoter, pL promoter, tac promoter, etc., are known as promoters frequently used. Examples of methods for evaluating strength of promoters and strong promoters are described in an article by Goldstein and Doi (Goldstein, M. A. and Doi R. H., 1995, Prokaryotic Promoters in Biotechnology, Biotechnol. Annu. Rev., 1:105-128), etc.

Moreover, it is also possible to substitute several nucleotides in a promoter region of a gene, so that the promoter has an appropriate strength, as disclosed in International Patent Publication WO00/18935. Substitution of the expression regulatory sequence can be performed, for example, in the same manner as in gene substitution using a temperature sensitive plasmid. Examples of vectors having a temperature sensitive replication origin which can be used for *Escherichia coli* or *Pantoea ananatis* include, for example, the temperature sensitive plasmid pMAN997 described in International Publication WO99/03988, its derivative, and so forth. Furthermore, substitution of an expression regulatory sequence can also be performed by methods which employ linear DNA, for example, a method called "Red-driven integration" using Red recombinase of λ phage (Datsenko, K. A. and Wanner, B. L., 2000, Proc. Natl. Acad. Sci. USA., 97:6640-6645), a method combining the Red-driven integration method and the λ phage excision system (Cho, E. H. et al., 2002, J. Bacteriol., 184:5200-5203) (WO2005/010175), and so forth. The modification of an expression regulatory sequence can be combined with the increasing gene copy number described above.

Furthermore, it is known that substitution of several nucleotides in a spacer between the ribosome-binding site (RBS) and the start codon, in particular, the sequences immediately upstream of the start codon, profoundly affect the mRNA translatability. Translation can be enhanced by modifying these sequences.

Enhancement of expression of the oxyS gene or the fix-ABC genes as compared to the parent strain, such as a wild-type or non-modified strain, can be confirmed by, for example, comparing amount of mRNA of each gene with that of the wild type or non-modified strain. Examples of the method for confirming the expression amount include Northern hybridization and RT-PCR (Molecular Cloning, Cold Spring Harbor Laboratory Press, Cold Spring Harbor, USA, 2001). The degree of the increase of the expression amount is not particularly limited so long as it increases as compared to that of a wild type or non-modified strain. However, it is increased, for example, 1.5 times or more, 2 times or more, or 3 times or more, compared with that of a wild type or non-modified strain.

Expression of the fixA, fixB, and fixC genes may be individually enhanced, or may be simultaneously enhanced as a polycistron. Furthermore, when the genes are introduced into a microorganism by using a vector, the genes encoding the subunits may be simultaneously carried by a single vector molecule, or may be separately carried by different vector molecules. Also when the genes encoding the subunits are inserted into a chromosome, the genes may be simultaneously inserted into the same site on the genome, or may be separately inserted on different sites.

Reduction of Gene Expression

Expression of a target gene can be reduced by modifying the target gene on a chromosome so that wild-type RNA or wild-type protein is not expressed, for example, by disrupting the target gene. Examples of the method for such gene disruption include, for example, methods using a linear DNA such as the method called "Red-driven integration" (Datsenko, K. A., and Wanner, B. L., 2000, Proc. Natl. Acad. Sci. USA, 97:6640-6645) and the method of utilizing the Red driven integration in combination with an excision system derived from λ phage (Cho, E. H., Gumport, R. I., Gardner, J. F., 2002, J. Bacteriol., 184:5200-5203) (refer to WO2005/010175), methods using a plasmid containing a temperature sensitive replication origin, methods using a plasmid capable of conjugative transfer, methods utilizing a suicide vector without a replication origin in a host (U.S. Pat. No. 6,303,383, Japanese Patent Laid-open No. 05-007491), and so forth.

Method for Producing L-Amino Acid

The methods described herein include a method for producing an L-amino acid by culturing a bacterium which belongs to the family Enterobacteriaceae and has an L-amino acid-producing ability in a medium containing a carbon source selected from a fatty acid and an alcohol, and collecting the L-amino acid from the medium, wherein the intracellular hydrogen peroxide concentration of the bacterium is reduced.

The intracellular hydrogen peroxide concentration of the bacterium can be reduced by, for example, using a bacterium modified so that intracellular hydrogen peroxide concentration of the bacterium is reduced, or by adding a substance that reduces intracellular hydrogen peroxide concentration of the bacterium to the medium.

Thus, the method encompasses:

a method for producing an L-amino acid including culturing a bacterium which belongs to the family Enterobacteriaceae and has an L-amino acid-producing ability in a medium containing a carbon source selected from a fatty acid and an alcohol, and collecting the L-amino acid from the medium, wherein the bacterium has been modified so that intracellular hydrogen peroxide concentration is reduced, and a method for producing an L-amino acid including culturing a bacterium which belongs to the family Enterobacteriaceae and has an L-amino acid-producing ability in a medium containing a carbon source selected from a fatty acid and an alcohol, and collecting the L-amino acid from the medium, wherein the medium contains a substance that reduces intracellular hydrogen peroxide concentration of the bacterium.

Furthermore, in the method, the bacterium may be modified so that intracellular hydrogen peroxide concentration is reduced, and in addition, the medium may contain a substance that reduces intracellular hydrogen peroxide concentration of the bacterium.

Examples of the substance that reduces intracellular hydrogen peroxide concentration of the bacterium include a substance that catalyzes a disproportionation reaction of hydrogen peroxide. Examples of such a substance include, for example, thiourea and so forth.

The term "fatty acid" refers to a monovalent carboxylic acid of long chain hydrocarbon represented by the general formula $C_nH_mCOOH$ (n+1 and m+1 represent the number of carbon atoms and the number of hydrogen atoms contained in the fatty acid, respectively). In general, a fatty acid having 12 or more carbon atoms is often referred to as a long chain fatty acid. There are a variety of fatty acids with varying number of carbons and varying degree of unsaturation. It is also known that fatty acids are constituents of fats and oils, and the compositions of fatty acids vary according to the types of fats and oils. Myristic acid ($C_{13}H_{27}COOH$) is a saturated fatty acid having 14 carbon atoms and is contained in coconut oil and palm oil. Palmitic acid ($C_{15}H_{31}COOH$) is a saturated fatty acid having 16 carbon atoms and is abundantly contained in vegetable fats and oils in general. Stearic acid ($C_{17}H_{35}COOH$) is a saturated fatty acid having 18 carbon atoms and is abundantly contained in animal fats and vegetable oils. Oleic acid ($C_{17}H_{33}COOH$) is a monovalent unsaturated fatty acid having 18 carbon atoms and is abundantly contained in animal fats or vegetable oils. Linoleic acid ($C_{17}H_{31}COOH$) is a multivalent unsaturated fatty acid having 18 carbon atoms and two double bonds of cis-configuration at positions 9 and 12. As the fatty acid, a mixture of the aforementioned long chain fatty acids can also be used. When a mixture of fatty acids is used as a carbon source, any mixing ratio of the fatty acids can be used, so long as the mixing ratio is a concentration ratio at which the bacterium used in the methods described herein can utilize the mixture as the carbon source. A mixture of fatty acids obtained by removing glycerol from a hydrolysate of fat or oil can also be used.

Examples of the alcohol include glycerol, ethanol, butanol, propanol, aliphatic alcohols, aromatic alcohols, and so forth.

The term "glycerol" refers to a substance having the nomenclature propane-1,2,3-triol. Glycerol can be pure glycerol, or crude glycerol. Crude glycerol refers to industrially produced glycerol which contains impurities. Crude glycerol is industrially produced by contacting fat or oil with water at a high temperature and under high pressure thereby to hydrolyze it, or by the esterification reaction for biodiesel fuel production. Biodiesel fuel refers to fatty acid methyl esters produced from fat or oil and methanol by a transesterification, and crude glycerol is produced as a by-product of this reaction (refer to Fukuda, H., Kondo, A., and Noda, H., 2001, J. Biosci. Bioeng., 92, 405-416). In the biodiesel fuel production process, in many cases, the alkaline catalyst method is used for the transesterification and acids are added for neutralization, and hence, crude glycerol with a purity of about 70 to 95% by weight containing water and impurities is produced. Crude glycerol produced in the biodiesel fuel production contains residual methanol, and salts of alkali such as NaOH as a catalyst and an acid such as $H_2SO_4$ used for neutralizing the alkali as impurities, in addition to water. Although it depends on the manufacturers and production methods, the content of such salts and methanol reaches several percent. The crude glycerol can contain ions derived from the alkali and the acid used for the neutralization of the alkali, such as sodium ions, potassium ions, chloride ions, and sulfate ions, in an amount of 2 to 7%, 3 to 6%, 4 to 5.8%, based on the weight of the crude glycerol. Although methanol may not be present as an impurity, it can be present in an amount of 0.01% or less.

The crude glycerol can further contain trace amounts of metals, organic acids, phosphorus, fatty acids, and so forth. Examples of the organic acids include formic acid, acetic acid, and so forth, and although they may not be present as impurities, they can be present in an amount of 0.01% or less. As the trace amounts of metals contained in the crude glycerol, trace metals required for growth of microorganisms can be present, and examples thereof include, for example, magnesium, iron, calcium, manganese, copper, zinc, and so forth. Magnesium, iron and calcium can be present in an amount of from 0.00001 to 0.1%, 0.0005 to 0.1%, 0.004 to 0.05%, 0.007 to 0.01%, in terms of the total amount based on the weight of the crude glycerol. Manganese, copper and zinc can be present in an amount of from 0.000005 to 0.01%, 0.000007 to 0.005%, or 0.00001 to 0.001%, in terms of the total amount.

It is sufficient that the purity of glycerol in the crude glycerol is 10% or higher, and it can be 50% or higher, 70% or higher, or 80% or higher. So long as the contained amounts of the impurities are within the aforementioned range, the purity of the glycerol can be 90% or higher.

When crude glycerol is used, the crude glycerol can be added to the medium according to the glycerol purity thereof so that the above glycerol concentration is obtained. Both glycerol and crude glycerol can also be added to the medium.

The carbon source can be a hydrolysate of fat or oil. So long as a fatty acid and/or glycerol is contained, a medium containing a hydrolysate of fat or oil is a "medium containing a fatty acid or an alcohol".

Fats and oils are esters of a fatty acid and glycerol, and they are also called triglycerides. As the fats and oils, any kinds of fats and oils including oils, which refer to those in a liquid state at ordinary temperature, and fats, which refer to those in a solid state at ordinary temperature, can be used, so long as hydrolysable fat or oil is chosen. Furthermore, any of animal fats and oils (including fish fats and oils) and vegetable fats and oils can be used, and they can be used independently or as a combination of two or more kinds of them. Fat or oil used as a raw material can be pure fat or oil, or a mixture containing fat or oil and substances other than the fat or oil. In the case of vegetable fats and oils, examples thereof include, for example, a plant extract containing fat or oil and a fractionation product thereof.

Examples of animal fats and oils include butter, lard, beef tallow, mutton tallow, whale oil, sardine oil, herring oil, and so forth. Examples of vegetable fats and oils include, but not limited to, palm oil, olive oil, rapeseed oil, soybean oil, rice bran oil, walnut oil, sesame oil, peanut oil, and so forth. Palm oil is oil that can be obtained from fruits of oil palm, and has come to be widely used as biodiesel fuel in recent years, and the production amount thereof is increasing. Oil palm is a generic name for the plants classified into the genus *Elaeis* of the family Palmae. Crude palm oil generally refers to unrefined palm oil produced at oil mills, and such palm oil is traded as crude palm oil. Microalgae that accumulate fat or oil are also known (Chisti, Y., Biotechnol. Adv., 2007, 25: 294-306), and the fat or oil can also be extracted from the alga cells. Although the alga cells also contains organic substances other than the fat or oil such as saccharides, proteins, or amino acids, a mixture containing these substances can be hydrolyzed and used as the carbon source.

As the fats and oils, fats and oils of which fatty acid species obtainable by hydrolysis can be utilized by the bacterium used in the methods described herein and which include the fatty acid species at a higher content, are particular examples. Examples of long chain fatty acid species that can be utilized by bacteria having an L-amino acid-producing ability include lauric acid, myristic acid, palmitic acid, stearic acid, oleic acid, and so forth.

A hydrolysate of fat or oil refers to a substance obtained by chemically or enzymatically hydrolyzing the aforementioned fat or oil, and refers to a mixture of a fatty acid and glycerol. As an industrial hydrolysis method, a continuous high temperature hydrolysis method in which fat or oil is brought into contact with water by countercurrent contacting at a high temperature (250 to 260° C.) under a high pressure (5 to 6 MPa) is commonly performed. A reaction performed at low temperature (about 30° C.) by using an enzyme is also industrially used (Jaeger, K. E. et al., 1994, FEMS Microbial. Rev., 15:29-63). As the aforementioned enzyme, a lipase, which is an enzyme that catalyzes a hydrolysis reaction of fats and oils, can be used. Lipases are industrially important enzymes and used for various industrial applications (Hasan, F. et al., 2006, Enzyme and Microbiol. Technol., 39:235-251). A hydrolysate of fat or oil is a mixture of a fatty acid and glycerol, and it is known that weight ratio of glycerol to the fatty acid contained in a hydrolysate of common fat or oil such as palm oil is about 10%. The hydrolysate of fat or oil is not particularly limited so long as the hydrolysate contains a fatty acid and/or glycerol. For example, a hydrolysate of fat or oil can be used as it is, a hydrolysate of fat or oil from which a portion of fatty acid and glycerol is removed can also be used, or a hydrolysate of fat or oil to which a fatty acid or glycerol is added can also be used. In such a case, the weight ratio of glycerol to the fatty acid can be 5 to 20:100, or 7.5 to 15:100.

The concentration of fatty acid can be measured by gas chromatography (Hashimoto, K. et al., 1996, Biosci. Biotechnol. Biochem., 70:22-30) or HPLC (Lin, J. T. et al., 1998, J. Chromatogr. A., 808:43-49).

The fatty acid to be added to the medium or fatty acid contained in a hydrolysate of fat or oil to be added to the medium can be used as an alkali metal salt of sodium, potassium, or the like, which can be micellized in water. However, the solubility of a sodium salt or potassium salt of fatty acid may not be sufficient for use as a fermentation raw material. Therefore, in order that a fatty acid can be more efficiently utilized as a carbon source by the bacterium having an L-amino acid-producing ability, a step can be employed for promoting homogenization, for example, performing emulsification. For example, as the emulsification method, addition of an emulsification enhancer or a surfactant can be contemplated. Examples of the emulsification enhancer referred to here include phospholipids and sterols. Examples of the surfactant include: as nonionic surfactants, poly(oxyethylene) sorbitan fatty acid esters such as poly(oxyethylene) sorbitan monooleic acid ester (Tween 80); alkyl glucosides such as n-octyl β-D-glucoside; sucrose fatty acid esters such as sucrose stearate; polyglycerin fatty acid esters such as polyglycerin stearic acid ester; and so forth. Examples of the surfactant include, as ampholytic surfactants, N,N-dimethyl-N-dodecylglycine betaine, which is an alkylbetaine, and so forth. Besides these, surfactants generally used in the field of biology such as Triton X-100, polyoxyethylene (20) cetyl ether (Brij-58), and nonylphenol ethoxylate (Tergitol NP-40) can be used.

Furthermore, an operation for promoting emulsification or homogenization of fatty acid is also effective. This operation can be any operation so long as an operation that promotes emulsification or homogenization of fatty acid is chosen. Specific examples thereof include homogenizer treatments, homomixer treatments, ultrasonication, high pressure treatments, high temperature treatments, and so forth. Homogenizer treatments, ultrasonication, and combinations thereof are particular examples.

It is a particular example to use a combination of the aforementioned treatment with a surfactant and homogenizer treatment and/or ultrasonication. These treatments can be carried out under an alkaline condition under which fatty acids are more stable. As the alkaline condition, pH not lower than 9 is one example, and pH not lower than 10 is another example.

The fatty acid or alcohol can be contained in the medium used in the methods described herein in any amount so long as the bacterium used for the method can utilize it as a carbon source. However, when the fatty acid or alcohol is added to the medium as the sole carbon source, it can be present at a concentration of 10 w/v % or lower, 5 w/v % or lower, or 2 w/v % or lower. When the fatty acid or alcohol is added to the medium as the sole carbon source, it can be present at a concentration of 0.2 w/v % or higher, 0.5 w/v % or higher, or 1.0 w/v % or higher.

Furthermore, the medium used for the methods described herein can contain other carbon sources in addition to the fatty acid or alcohol. Other carbon sources can include saccharides such as glucose, fructose, sucrose, lactose, galactose, blackstrap molasses, starch hydrolysate, and sugar solutions obtained by hydrolysis of biomass, and organic acids such as fumaric acid, citric acid, and succinic acid. These other carbon sources can be used in such amount that the ratio of the fatty acid or alcohol in the carbon source is 10% by weight or more, 30% by weight or more, or 50% by weight or more. In addition, a strain not having sucrose-utilizing ability can be made into a strain that can utilize sucrose as a carbon source by introducing a gene for sucrose utilization (U.S. Pat. No. 5,175,107).

When a fatty acid or glycerol is added to a feed medium as the sole carbon source, it is can be present in the feed medium at such a concentration that the concentration thereof in the medium after feeding is 5 w/v % or lower, 2 w/v % or lower, or 1 w/v % or lower. When a fatty acid or glycerol is added to a feed medium as the sole carbon source, the amount thereof can be controlled to be 0.01 w/v % or higher, 0.02 w/v % or higher, or 0.05 w/v % or higher.

A fatty acid or an alcohol can be contained at a certain constant concentration throughout the culture process, it can be added only to the feed medium or the starting medium, or if other carbon sources are contained at a sufficient level, there can be a period where a fatty acid and/or an alcohol temporarily runs short. The term "temporarily" means that, for example, a fatty acid and/or an alcohol can run short for a period corresponding to 10%, 20%, or 30% at most, of the entire fermentation period. Even such a case as described above, where the concentration of a fatty acid and/or an alcohol can temporarily become zero, is included in the scope of the expression "to culture in a medium containing a fatty acid or an alcohol as a carbon source", so long as there is a period of culture in a medium containing a fatty acid or an alcohol.

As components other than the carbon source to be added to the medium, a nitrogen source, inorganic ions, and other organic components can be used, as required. As the nitrogen source contained in the medium, one or more of the following can be used: ammonia; ammonium salts such as ammonium sulfate, ammonium carbonate, ammonium chloride, ammonium phosphate, ammonium acetate, and urea; nitrates; or so forth. Ammonia gas and aqueous ammonia used for pH adjustment can also be used as the nitrogen source. Furthermore, peptone, yeast extract, meat extract, malt extract, corn steep liquor, soybean hydrolysate, and so forth can also be used as the nitrogen source. The medium can contain only one kind of these nitrogen sources, or two or more kinds of these nitrogen sources. These nitrogen sources can also be used for both the starting medium and the feed medium. Furthermore, the same nitrogen source can be used for both the starting medium and the feed medium, or the nitrogen source of the feed medium may be different from that of the starting medium.

The medium of the present disclosure can contain a phosphoric acid source and a sulfur source in addition to the carbon source and the nitrogen source. As the phosphoric acid source, potassium dihydrogenphosphate, dipotassium hydrogenphosphate, phosphoric acid polymers such as pyrophosphoric acid, and so forth, can be used. Although the sulfur source can be any substance containing sulfur atoms, sulfuric acid salts such as sulfates, thiosulfates, and sulfites; and sulfur-containing amino acids such as cysteine, cystine, and glutathione are examples, and ammonium sulfate is a particular example.

Furthermore, the medium may contain a growth promoting factor (nutrient having a growth promoting effect) in addition to the aforementioned components. As the growth promoting factor, trace metals, amino acids, vitamins, nucleic acids as well as peptone, casamino acid, yeast extract, soybean protein degradation product and so forth containing the foregoing substances can be used. Examples of the trace metals include iron, manganese, magnesium, calcium and so forth. Examples of the vitamins include vitamin $B_1$, vitamin $B_2$, vitamin $B_6$, nicotinic acid, nicotinamide, vitamin $B_{12}$ and so forth. These growth promoting factors may be contained in the starting medium or the feed medium.

Furthermore, when an auxotrophic mutant that requires an amino acid or the like for growth thereof is used, a required nutrient can be supplemented to the medium. In particular, since the L-lysine biosynthetic pathway is enhanced and L-lysine degrading ability is often attenuated in L-lysine-producing bacteria that can be used as described below, one or more types of substances selected from L-threonine, L-homoserine, L-isoleucine, and L-methionine can be added. The starting medium and the feed medium may have the same or different medium composition. Furthermore, the starting medium and the feed medium may have the same or different sulfur concentration. Furthermore, when the feed medium is fed at multiple stages, the compositions of the feed medium fed at the stages may be the same or different.

When a substance that reduces intracellular hydrogen peroxide concentration of the bacterium is added to the medium, this substance may be contained throughout all the process of the culture, or added only to the feed medium or the starting medium. Concentration of the substance in the medium can be 0.01 to 25 mM.

The culture can be performed as an aeration culture at a fermentation temperature of 20 to 45° C., or 33 to 42° C. The oxygen concentration is controlled to be about 5 to 50%, or about 10%. Furthermore, the aeration culture is can be performed while controlling pH to be 5 to 9. If pH of the medium is lowered during the culture, the medium can be neutralized by, for example, adding calcium carbonate or an alkaline such as ammonia gas and aqueous ammonia. If culture is performed under such conditions as described above, for about 10 to 120 hours, a marked amount of L-amino acid is accumulated in the culture medium.

In order to keep the accumulation of L-amino acid at a certain level or higher, the culture of the bacterium can be carried out as separate seed culture and main culture. The seed culture can be carried out as shake culture or batch culture using a flask or the like, and the main culture can be carried out as fed-batch culture or continuous culture. Both the seed culture and main culture can be carried out as batch culture.

When fed-batch culture or continuous culture is performed, the feed medium can be intermittently fed so that feeding of a fatty acid or alcohol, or other carbon sources, is temporarily stopped. For example, the supply of the feed medium can be stopped so that duration per feeding is 30% or less, 20% or less, or 10% or less, of the total period for the feeding of multiple times. When the feed medium is intermittently fed, the feed medium can be initially added over a certain period of time, and the second and following additions can be controlled so that they are started when elevation of pH or elevation of dissolved oxygen concentration, due to the depletion of the carbon source in the fermentation medium during an addition-stopped period prior to a certain medium-addition period, is detected by a computer, and thus the substrate concentration in the culture tank is always automatically maintained at a low level (U.S. Pat. No. 5,912,113).

The feed medium used for the fed-batch culture can be a medium containing a fatty acid or an alcohol, another carbon source, and a nutrient having growth-promoting effect (growth-promoting factor), and fatty acid concentration in the fermentation medium can be controlled to be a certain level or lower.

As the other carbon source added to the feed medium, glucose, sucrose and fructose are particular examples. As the growth-promoting factor, nitrogen source, phosphoric acid, amino acids and so forth are particular examples. As the nitrogen source, ammonia, ammonium salts (such as ammonium sulfate, ammonium carbonate, ammonium chloride, ammonium phosphate, ammonium acetate, and urea), nitrates, and so forth, can be used. Furthermore, as the phosphoric acid source, potassium dihydrogenphosphate and dipotassium hydrogenphosphate can be used. As for the amino acids, when an auxotrophic mutant strain is used, a required nutrient can be added. Furthermore, the feed medium can consist of one type of medium, or a mixture of two or more types of media. When two or more types of feed media are used, the media can be mixed and fed by using one feed tube, or the media can be fed by using two or more feed tubes.

When the continuous culture method is used, the medium can be extracted and fed simultaneously, or after a part of the medium is extracted, the medium can be fed. Furthermore, there can also be used a continuous culture method including recycling cells in which the culture medium containing an L-amino acid and bacterial cells is extracted, and only the cells are returned to the fermentation tank (refer to French Patent No. 2669935). As the method for continuously or intermittently feeding a nutrient source, the same method as used in the fed-batch culture is used.

The continuous culture method including recycling cells is a method of intermittently or continuously extracting the fermentation medium when an intended amino acid concentration is obtained, collecting only the L-amino acid from the medium, and recycling the filtration residue containing the cells into the fermentation tank, and such a method can be performed with reference to, for example, French Patent No. 2669935.

When the culture medium is intermittently extracted, it is recommendable that a part of the L-amino acid is extracted when the L-amino acid concentration reaches a predetermined level, and a fresh medium is fed to continue the culture. Furthermore, the medium can be added in such a volume that the final volume of the medium becomes an equal volume to the volume of the culture medium before the extraction. The term "equal volume" means a volume corresponding to about 93 to 107% of the volume of the medium before the extraction.

When the culture medium is continuously extracted, the extraction can be started at the same time as or after the feeding of the nutrient medium. For example, within 5 hours, 3 hours, or 1 hour, after the start of the feeding, the extraction can be started. Furthermore, the extraction volume of the culture medium can be equal to the volume of the medium fed.

When a basic amino acid such as L-lysine is produced, the production can be performed by a method in which fermentation is performed by controlling pH of the medium during culture to be 6.5 to 9.0 and pH of the medium at the end of the culture to be 7.2 to 9.0, while securing a culture period where the medium contains 20 mM or more of bicarbonate ions and/or carbonate ions, so that these bicarbonate ions and/or carbonate ions act as counter ions of the basic amino acid, and the objective basic amino acid is then collected (Japanese Patent Laid-open No. 2002-65287, U.S. Patent Application Pub. No. 2002/0025564A, EP 1813677 A).

When a microorganism having a basic amino acid-producing ability is cultured in a medium under aerobic conditions, carbonate ions, bicarbonate ions, or both can be used as major counter ions of the basic amino acid. To provide bicarbonate ions and/or carbonate ions in the medium in an amount required to act as counter ions of the basic amino acid, it is known that the pH of the medium can be controlled to be 6.5 to 9.0, 6.5 to 8.0, during the culture, and can be controlled to be 7.2 to 9.0 at the end of the culture, and the pressure in the fermentation tank can be controlled so that it is positive during fermentation, or carbon dioxide or a mixed gas containing carbon dioxide can be supplied into the medium (Japanese Patent Laid-open No. 2002-65287, U.S. Patent Published Application No. 2002/0025564, EP 1813677 A).

Both controlling the pressure in the fermentation tank to be positive during the fermentation, and supplying carbon dioxide gas or a mixed gas containing carbon dioxide gas to the medium, can be performed. In either case, the above operations can be performed so that there is a culture period where 20 mM or more, 30 mM or more, or 40 mM or more, of bicarbonate ions and/or carbonate ions are present in the medium. The internal pressure of the fermentation tank, the supply amount of carbon dioxide or mixed gas containing carbon dioxide, or the limited gas supply volume can be determined by, for example, measuring bicarbonate ions or carbonate ions in the medium, or measuring pH or ammonia concentration of the medium.

In the above embodiment, pH of the medium is controlled to be 6.0 to 9.0, or 6.5 to 8.0, during the culture, and 7.2 to 9.0 at the end of the culture. According to the above embodiment, pH of the medium for ensuring the presence of bicarbonate ions and/or carbonate ions in an amount required as counter ions can be made lower compared with the conventional methods. When pH is controlled with ammonia, ammonia is supplied in order to increase the pH, and it can also act as a nitrogen source for the basic amino acid. Examples of cations other than the basic amino acid in the medium include K, Na, Mg, Ca, etc., originating in medium components. These can exist in an amount of 50% or less of the total cations.

Furthermore, the internal pressure of the fermentation tank during fermentation can be made positive by, for example, making the gas supply pressure higher than the exhaust pressure. By making the internal pressure of the fermentation tank positive, the carbon dioxide generated by fermentation dissolves in the culture medium to generate bicarbonate ions or carbonate ions, and these can act as counter ions of the basic amino acid. The internal pressure of the fermentation tank can be, specifically, 0.03 to 0.2 MPa, 0.05 to 0.15 MPa, or 0.1 to 0.3 MPa, in terms of the gage pressure (pressure difference with respect to the atmospheric pressure). Moreover, by supplying carbon dioxide or a mixed gas containing carbon dioxide to the culture medium, carbon dioxide can be dissolved in the medium. Furthermore, while supplying carbon dioxide or a mixed gas containing carbon dioxide to the medium, the internal pressure of the fermentation tank can also be adjusted to be positive.

The internal pressure of the fermentation tank can be adjusted to be positive by, for example, making the gas supply pressure higher than the exhaust pressure. Furthermore, when carbon dioxide is supplied to the medium, for example, pure carbon dioxide or a mixed gas containing 5 volume % or more of carbon dioxide can be bubbled in the medium.

The aforementioned methods for dissolving bicarbonate ions and/or carbonate ions in the medium can be used independently, or as a combination of two or more of them.

In the conventional methods, a sufficient amount of ammonium sulfate or ammonium chloride is usually added to the medium to provide counter anions of the basic amino acid to be produced and sulfuric acid or hydrochloric acid decomposition products of proteins etc. are also added to the medium as nutrient components, and hence, sulfate ions and chloride ions generated from these are present in the medium. Therefore, the concentration of the weakly acidic carbonate ions is extremely low during the culture, i.e., it is at a ppm order. The above embodiment is characterized in that these sulfate ions and chloride ions are reduced, and the carbon dioxide released by the microorganism during fermentation is dissolved in the medium under the aforementioned fermentation environment and used as counter ions. Therefore, in the above embodiment, it is not required to add sulfate ions or chloride ions to the medium in an amount more than the amount required for the growth. An appropriate amount of ammonium sulfate or the like is fed to the medium at an early stage of the culture, and the feeding is terminated in the middle of the culture. Alternatively, ammonium sulfate or the like can be fed while maintaining the balance with the dissolved amount of carbonate ions or bicarbonate ions in the medium. Moreover, as a nitrogen source of the basic amino acid, ammonia can be fed to the medium. Ammonia can be supplied to the medium independently, or together with other gases.

The concentrations of anions other than bicarbonate ions and/or carbonate ions in the medium are low so long as they are present in amounts that are required for the growth of the microorganism. Examples of such anions include chloride ions, sulfate ions, phosphate ions, ionized organic acids, hydroxide ions, and so forth. The total molar concentration of these other ions can be usually 900 mM or lower, 700 mM or lower, 500 mM or lower, 300 mM or lower, or 200 mM or lower.

To reduce the amounts of sulfate ions and/or chloride ions to be used is one of the aspects of the above embodiment, and the amount of sulfate ions or chloride ions or the total amount of the both contained in the medium is usually 700 mM or lower, 500 mM or lower, 300 mM or lower, 200 mM or lower, or 100 mM or lower.

If ammonium sulfate is added to a medium as a counter ion source of a basic amino acid, carbon dioxide in the culture medium is usually eliminated by sulfate ions. By contrast, in the above embodiment, it is not necessary to add an excess amount of ammonium sulfate to the medium, and therefore carbon dioxide can be easily dissolved in the fermentation medium.

Furthermore, in the above embodiment, the total ammonia concentration in the medium can be controlled to such an extent that "production of the basic amino acid is not inhibited". Examples of such conditions include, for example, conditions giving yield and/or productivity corresponding to 50% or more, 70% or more, or 90% or more, of the yield and/or productivity obtainable in the production of the basic amino acid under optimal conditions. Specifically, the total ammonia concentration in the medium can be 300 mM or lower, 250 mM or lower, or 200 mM or lower. The dissociation degree of ammonia decreases as the pH becomes higher. Non-dissociating ammonia is more toxic to bacteria compared with ammonium ions. Therefore, the upper limit of the total ammonia concentration should be determined also depending on the pH of the culture medium. That is, as the pH of the culture medium increases, the acceptable total ammonia concentration decreases. Therefore, the aforementioned total ammonia concentration at which "production of the basic amino acid is not inhibited" can be determined for each specific pH value. However, the total ammonia concentration range that is acceptable at the highest pH level during the culture can be used as the upper limit of the total ammonia concentration throughout the entire culture period.

On the other hand, the total concentration of ammonia as a source of nitrogen required for growth of the microorganism and production of the basic substance is not particularly limited, and can be appropriately determined, so long as depletion of ammonia does not continue during the culture, and thus decrease of productivity for the objective substance of the microorganism due to the shortage of the nitrogen source does not occur. For example, the ammonia concentration can be measured over time during the culture, and if ammonia in the medium is depleted, a small amount of ammonia can be added to the medium. Although the ammonia concentration after the addition of ammonia is not particularly limited, the total ammonia concentration can be, for example, 1 mM or higher, 10 mM or higher, or 20 mM or higher.

The L-amino acid can usually be collected from fermentation broth by a combination of conventionally known methods such as an ion-exchange resin method (Nagai, H. et al., Separation Science and Technology, 39(16), 3691-3710), a precipitation method, a membrane separation method (Japanese Patent Laid-open Nos. 9-164323 and 9-173792), a crystallization method (WO2008/078448, WO2008/078646), and other methods. When the L-amino acid accumulates in the cells, the cells can be disrupted with, for example, ultrasonic waves or the like, and the L-amino acid can be collected by the ion exchange resin method or the like from the supernatant obtained by removing the cells from the cell-disrupted suspension by centrifugation.

The collected L-amino acid can contain bacterial cells, medium components, moisture, and by-product metabolites of the bacterium in addition to the objective L-amino acid. Purity of the collected L-amino acid can be 50% or higher, 85% or higher, or 95% or higher (Japanese Patent No. 1214636, U.S. Pat. Nos. 5,431,933, 4,956,471, 4,777,051, 4,946,654, 5,840,358, 6,238,714, U.S. Patent Application Pub. No. 2005/0025878).

Furthermore, when L-amino acid deposits in the medium, it can be collected by centrifugation, filtration, or the like. L-Amino acid deposited in the medium and L-amino acid dissolved in the medium can be isolated together after the L-amino acid dissolved in the medium is crystallized.

EXAMPLES

Hereafter, the present disclosure will be more specifically explained with reference to examples.

Example 1

Culture of *Escherichia coli* in Minimal Medium Containing Fatty Acid as a Sole Carbon Source and Measurement of Intracellular Hydrogen Peroxide Concentration MG1655/pTWV228 strain obtained by introducing plasmid pTWV228 (Takara Bio Inc.) into the *Escherichia coli* MG1655 strain (ATCC 47076) in a conventional manner was cultured at 37° C. in the L medium containing 50 mg/L of ampicillin until the final $OD_{600}$ became about 0.6, then a 40% glycerol solution was added to the culture medium in the same volume as that of the culture medium, and the mixture was stirred, divided into appropriate volumes, and stored at −80° C. This preparation was called glycerol stock.

The glycerol stock of the MG1655/pTWV228 strain was scraped off with a loop, and one loop of the cells were plated on the M9 glucose agar medium, and cultured for 24 hours as static culture. The grown cells were scraped off, suspended in a 0.85% NaCl aqueous solution, and inoculated into 10 mL of the M9 sodium oleate liquid medium for test tube or the M9 glucose liquid medium for test tube contained in an L-shaped test tube at a turbidity of 0.02 measured at a wavelength of 600 nm. The culture was continued at 37° C. and 70 rpm for 44 hours by using a constant-temperature shaking incubator TN-2612 (Advantech). The turbidity was measured using a spectrophotometer U-2000 (Hitachi, Ltd.) (the same shall apply to the following experiments).

Compositions of the aforementioned media are shown below. All the concentrations are final concentrations.

[Composition of M9 Glucose Agar Medium]

| | |
|---|---|
| Glucose | 2 g/L |
| $Na_2HPO_4$ | 6 g/L |
| $KH_2PO_4$ | 3 g/L |
| NaCl | 0.5 g/L |
| $NH_4Cl$ | 1 g/L |
| $MgSO_4 \cdot 7H_2O$ | 0.246 g/L |
| Thiamine | 0.5 mg/L |
| Agar | 15 g/L |

[Composition of M9 Sodium Oleate Liquid Medium for Test Tube]

| | |
|---|---|
| Sodium oleate (Junsei Chemical) | 1 g/L |
| Tween 80* (Nakalai Tesque) | 0.5% (v/v) |
| $Na_2HPO_4$ | 6 g/L |
| $KH_2PO_4$ | 3 g/L |
| NaCl | 0.5 g/L |
| $NH_4Cl$ | 1 g/L |
| $MgSO_4 \cdot 7H_2O$ | 0.246 g/L |
| Thiamine | 0.5 mg/L |

*Poly(oxyethylene)sorbitan monooleate

[Composition of M9 Glucose Liquid Medium for Test Tube]

| | |
|---|---|
| Glucose | 1 g/L |
| Tween 80 (Nakalai Tesque) | 0.5% (v/v) |
| $Na_2HPO_4$ | 6 g/L |
| $KH_2PO_4$ | 3 g/L |
| NaCl | 0.5 g/L |
| $NH_4Cl$ | 1 g/L |
| $MgSO_4 \cdot 7H_2O$ | 0.246 g/L |
| Thiamine | 0.5 mg/L |

During the culture, an appropriate volume of each liquid medium was sampled, appropriately diluted, and inoculated on the LB medium, the number of living bacterial cells was measured, and turbidity was measured at a wavelength of 600 nm. Furthermore, hydrogen peroxide concentration in the cells contained in the liquid medium was measured according to the descriptions of the following references: Beatriz Gonzalez-Flecha, and Bruce Demple, Journal Of Bacteriology, 1994, Vol. 176, pp. 2293-2299; and Ken-ichi Setsukinai et al., 2003, The Journal Of Biological Chemistry, Vol. 278, pp. 3170-3175.

Specifically, 400 µL of the aforementioned culture medium was taken, and centrifuged at 4° C. and 13,800×g for 2 minutes, 360 µL of the supernatant was removed, and the cells were suspended in 360 µL of a 100 mM phosphate buffer, pH 7.3, and left standing for 10 minutes. Then, the suspension was centrifuged at 4° C. and 13,800×g for 2 minutes, 10 μL of the obtained supernatant was sampled, and the following reaction solution (i) or (ii) was added to the supernatant on a 96-well plate.

Reaction solution (i): horseradish peroxidase (final concentration, 2 μM; Wako Pure Chemical Industries), 10 μM fluorescent color developing substrate HPF (Sekisui Medical), and phosphate buffer (final concentration, 100 mM; pH 7.3)

Reaction mixture (ii): catalase (final concentration, 2 μM; Wako Pure Chemical Industries), 10 μM fluorescent color developing substrate HPF (Sekisui Medical), and phosphate buffer (final concentration, 100 mM; pH 7.3)

The supernatant was treated with each reaction solution at 37° C. for 75 minutes on the 96-well plate in a dark place, fluorescence obtained by excitation at an excitation wavelength of 490 nm was measured at 515 nm, and the fluorescence intensity obtained with the reaction mixture (ii) was subtracted from the fluorescence intensity obtained with the reaction mixture (i) to determine hydrogen peroxide concentration in the bacterial cells.

It was separately confirmed that *Escherichia coli* could not utilize the surfactant Tween 80 by using the M9 minimal medium containing Tween 80. Consumption of all the glucose added to the medium was separately confirmed by using a Biotech Analyzer AS310. Furthermore, consumption of all the oleate added to the medium was separately confirmed by using a gas chromatograph GC-2014 (Shimadzu).

Figure 2:
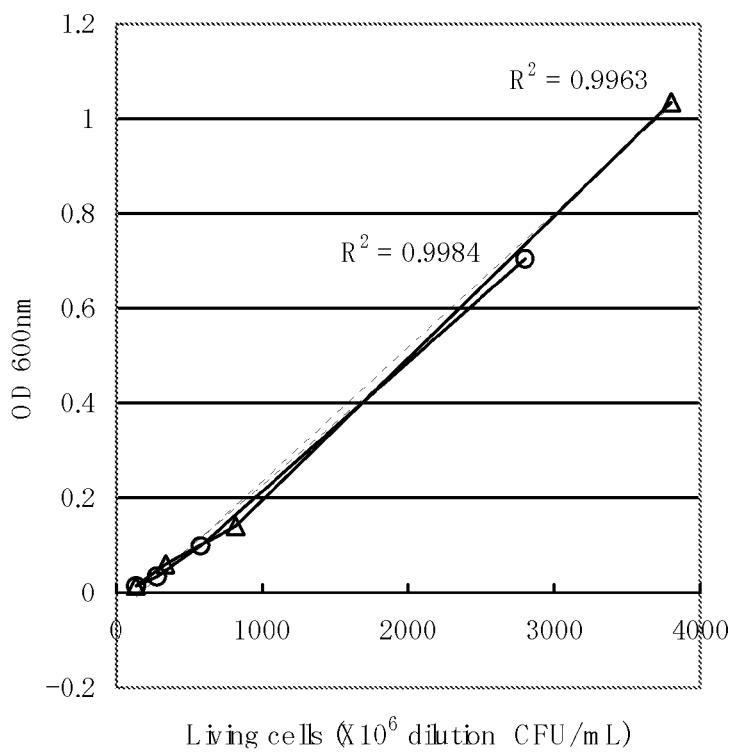
FIG. 2 shows a relation between growth (OD600) of *E. coli* in a minimal medium containing glucose (O) or oleic acid (Δ) as a carbon source and the numbers of living bacteria.
Figure 3:
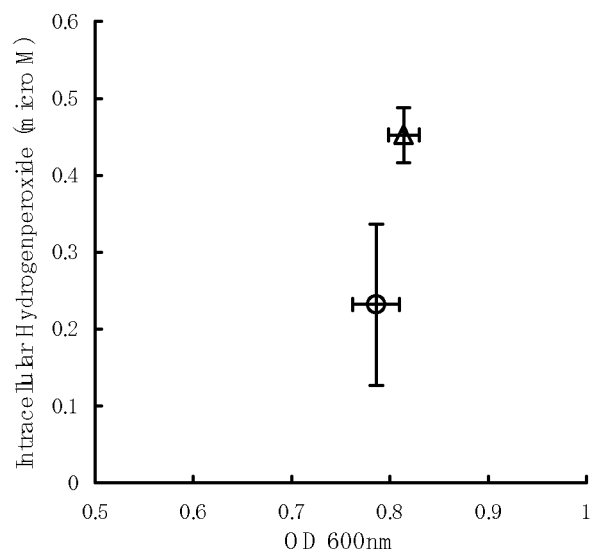
FIG. 3 shows a relation between growth (OD600) of *E. coli* in a minimal medium containing glucose (O) or oleic acid (Δ) as a carbon source and intracellular hydrogen peroxide concentration thereof.
Figure 4:
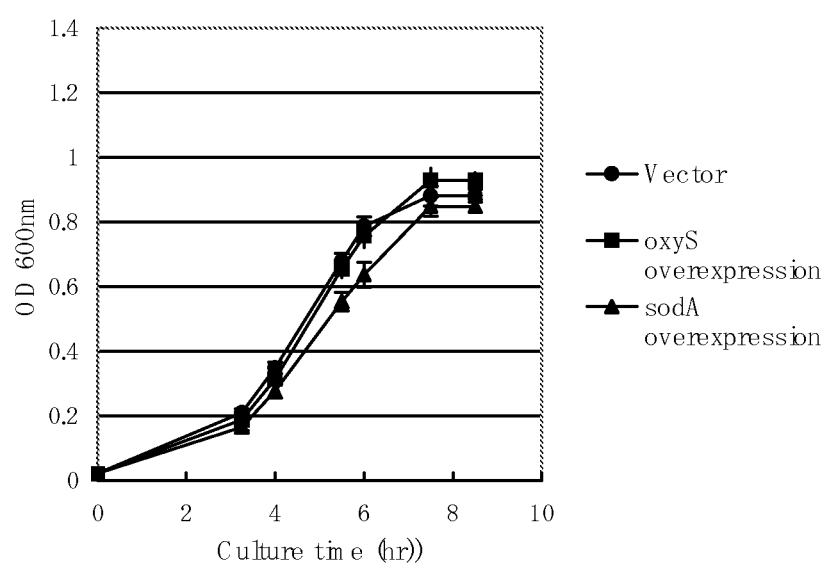
FIG. 4 shows growth (OD600) of *E. coli* oxyS gene-amplified strain (oxyS overexpression) and sodA gene-amplified strain (sodA overexpression) in a minimal medium containing glucose as a carbon source.
Figure 5:
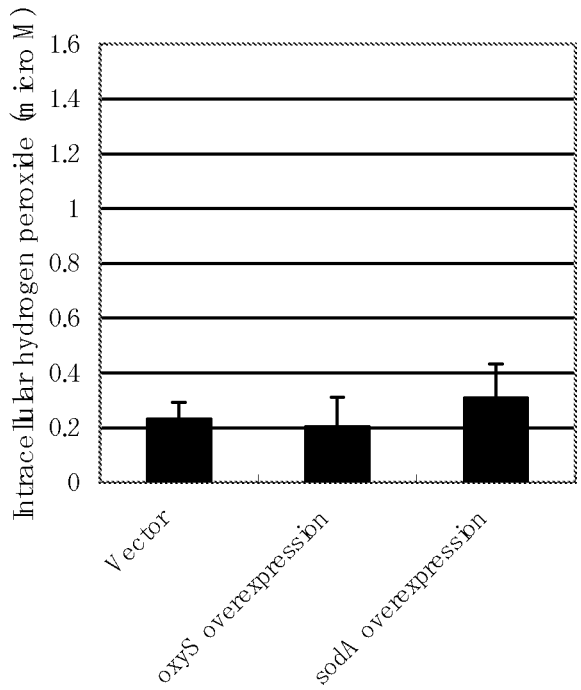
FIG. 5 shows intracellular hydrogen peroxide concentrations of *E. coli* oxyS gene-amplified strain (oxyS overexpression) and sodA gene-amplified strain (sodA overexpression) cultured in a minimal medium containing glucose as a carbon source.
Figure 6:
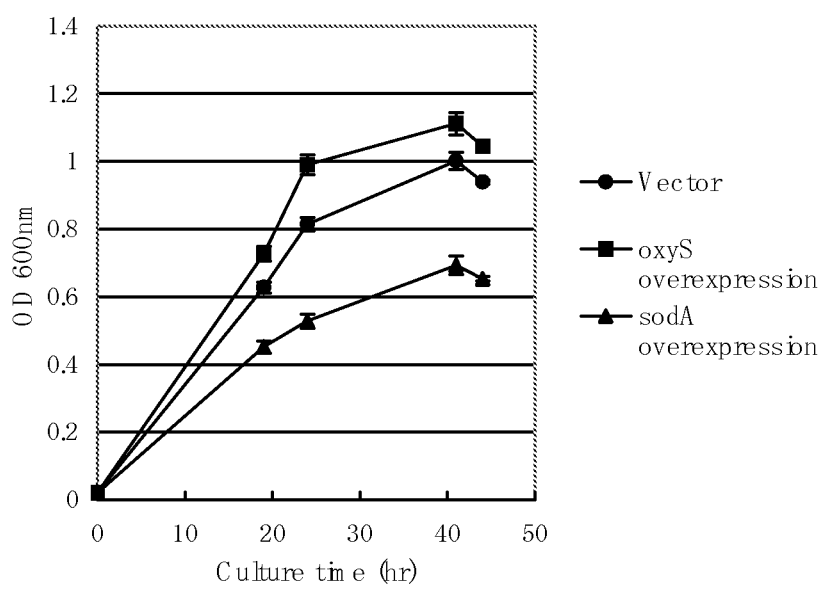
FIG. 6 shows growth (OD600) of *E. coli* oxyS gene-amplified strain (oxyS overexpression) and sodA gene-amplified strain (sodA overexpression) in a minimal medium containing oleic acid as a carbon source.
Figure 7:
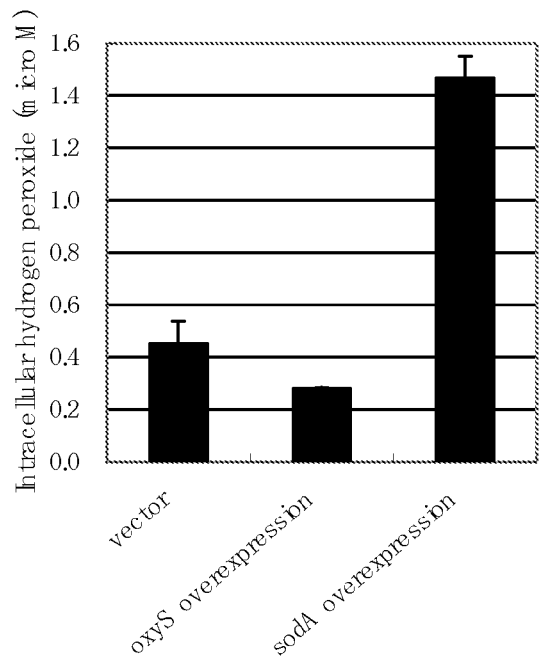
FIG. 7 shows intracellular hydrogen peroxide concentrations of *E. coli* oxyS gene-amplified strain (oxyS overexpression) and sodA gene-amplified strain (sodA overexpression) cultured in a minimal medium containing oleic acid as a carbon source.

The results of the culture are shown in FIGS. 1 to 3. As seen from the results shown in FIGS. 1 to 3, strong positive correlation was observed between the turbidity at the wavelength of 600 nm not higher than 1 shown by the MG1655/pTWV228 strain and the number of living bacterial cells. Furthermore, the MG1655/pTWV228 strain cultured with the M9 sodium oleate liquid medium for test tube showed a significantly higher intracellular hydrogen peroxide concentration as compared to the MG1655/pTWV228 strain cultured with the M9 glucose liquid medium for test tube. On the basis of these culture results, it was estimated that larger oxidation stress, mainly consisting of hydrogen peroxide, was imposed on *Escherichia coli* at the time of utilization of the fatty acid as compared to that imposed at the time of utilization of glucose.

Example 2

Culture of Hydrogen Peroxide Secretion-Promoted *Escherichia coli* in Minimal Medium Containing Fatty Acid as Sole Carbon Source and Measurement of Intracellular Hydrogen Peroxide Concentration Construction of oxyS Gene-Amplified *Escherichia coli*

In order to confirm the effect of amplification of the oxyS gene concerning contribution to growth of *Escherichia coli* in culture using a fatty acid as a carbon source, a plasmid for amplifying oxyS was constructed. PCR was performed using the synthetic oligonucleotides having the nucleotide sequences of SEQ ID NOS: 1 and 2 as the primers and the chromosomal DNA of the *Escherichia coli* MG1655 strain as the template. The PCR product was purified and ligated to the vector pTWV228 (Takara Bio Inc.) digested with SalI to construct a plasmid pTWV228-oxyS for amplification of oxyS.

MG1655/pTWV228-oxyS strain obtained by introducing the plasmid pTWV228-oxyS into the MG1655 strain in a conventional manner was cultured at 37° C. in the L medium containing 50 mg/L of ampicillin until the final $OD_{600}$ became about 0.6, and then glycerol stock was prepared and stored. The glycerol stock was prepared by adding a 40% glycerol solution to the culture medium in the same volume as that of the culture medium, stirring the mixture, dividing the mixture into appropriate volumes, and storing them at −80° C. (the same shall apply to the following descriptions).

(2) Construction of sodA Gene-Amplified *Escherichia coli*

In order to confirm the effect of amplification of the sodA gene shown in SEQ ID NO: 9 concerning contribution to growth of *Escherichia coli* in culture using a fatty acid as a carbon source, a plasmid for amplifying sodA was constructed. PCR was performed using synthetic oligonucleotides having the nucleotide sequences of SEQ ID NOS: 3 and 4 as the primers and the chromosomal DNA of the *Escherichia coli* MG1655 strain as the template. The PCR product was purified and ligated to the vector pTWV229 (Takara Bio Inc.) digested with HindIII and SalI to construct a plasmid pTWV229-sodA for amplification of sodA.

MG1655/pTWV229-sodA strain was constructed by introducing pTWV229-sodA into the MG1655 strain. The MG1655/pTWV228-sodA strain was cultured at 37° C. in the L medium containing 50 mg/L of ampicillin until the final $OD_{600}$ became about 0.6, and then glycerol stock of the MG1655/pTWV228-sodA strain was prepared and stored.

(3) Measurement of Hydrogen Peroxide Concentration in sodA Gene-Amplified Strain Cultured in Medium Containing Fatty Acid as Carbon Source Each of the glycerol stocks of the MG1655/pTWV228 strain, the MG1655/pTWV228-oxyS strain, and the MG1655/pTWV229-sodA strain was scraped off with a loop, and one loop of the cells were plated on the M9 glucose agar medium, and cultured for 24 hours as a static culture. The grown cells were scraped off, suspended in a 0.85% NaCl aqueous solution, and inoculated into 10 mL of the aforementioned M9 sodium oleate liquid medium for test tube or M9 glucose liquid medium for test tube contained in an L-shaped test tube at a turbidity of 0.02 measured at a wavelength of 600 nm. The culture was continued at 37° C. and 70 rpm for 44 hours by using a constant-temperature shaking incubator TN-2612 (Advantech).

During the culture, an appropriate volume of each liquid medium was sampled, and appropriately diluted, and turbidity was measured at a wavelength of 600 nm. Furthermore, hydrogen peroxide concentration in the cells at the logarithmic phase contained in the liquid medium and showing a turbidity of about 0.6 at a wavelength of 600 nm was measured according to the aforementioned method.

It was separately confirmed that *Escherichia coli* used for the culture could not utilize the surfactant Tween 80 by using the M9 minimal medium containing Tween 80. Consumption of all the glucose added to the medium was separately confirmed by using a Biotech Analyzer AS310. Furthermore, consumption of all the oleate added to the medium was separately confirmed by using a gas chromatograph GC-2014 (Shimadzu).

The results of the culture are shown in FIGS. 4 to 7. As seen from the results shown in FIGS. 4 to 7, significant reduction of the intracellular hydrogen peroxide concentration and significant improvement of growth due to the amplification of oxyS were observed in the culture using oleate as the carbon source. Furthermore, significant increase of the intracellular hydrogen peroxide concentration and significant degradation of growth due to the amplification of sodA were observed.

Example 3

L-Lysine Production with oxyS Expression-Enhanced Strain

Introduction of Plasmid for Enhancing oxyS Expression into L-Lysine-Producing Bacterium In order to confirm the effect of amplification of the oxyS gene concerning contribution to L-lysine-producing ability, pTWV228-oxyS prepared in Example 2 was introduced into the L-lysine-producing bacterium WC196ΔcadAΔldcC/pCABD2 constructed by the method described in U.S. Patent Application Pub. No. 2006/0160191 to construct WC196ΔcadAΔldcC/pCABD2,pTWV228-oxyS strain. The WC196ΔcadAΔldcC (also referred to as "WC196LC") strain is a strain obtained from the Escherichia coli WC1-96 strain by disrupting the lysine decarboxylase genes, cadA and ldc, according to the method using the Red-driven integration method (Datsenko K. A., Wanner, B. L., 2000, Proc. Natl. Acad. Sci. USA, 97, 6640-6645) and the excision system derived from λ-phage (Cho, E. H., Gumport, R. I., Gardner, J. F., 2002, J. Bacteriol., 184:5200-5203) in combination (refer to WO2005/010175). A strain obtained by introducing pCABD2 into this strain is the WC196ΔcadAΔldcC/pCABD2 (WC196LC/pCABD2) strain. The plasmid pCABD2 contains a mutant dapA gene coding for dihydrodipicolinate synthase (DDPS) derived from Escherichia coli having a mutation for desensitization to feedback inhibition by L-lysine, a mutant lysC gene coding for aspartokinase III derived from Escherichia coli having a mutation for desensitization to feedback inhibition by L-lysine, the dapB gene coding for dihydrodipicolinate reductase derived from Escherichia coli, and the ddh gene coding for diaminopimelate dehydrogenase derived from Brevibacterium lactofermentum. The WC196LC/pCABD2,pTWV228-oxyS strain was cultured at 37° C. in the L medium containing 20 mg/L of streptomycin and 50 mg/L of ampicillin until the final $OD_{600}$ became about 0.6, and then glycerol stock was prepared and stored at −80° C.

Evaluation of L-Lysine-Producing Ability of oxyS Expression-Enhanced L-Lysine-Producing Bacterium Using Fatty Acid as Carbon Source The aforementioned glycerol stock was thawed, 100 μL of the thawed stock was uniformly applied to an L plate containing 20 mg/L of streptomycin and 50 mg/L of ampicillin, and cultured at 37° C. for 24 hours as static culture. About ¼ of the obtained cells on the plate were suspended in 0.5 mL of physiological saline, and turbidity was measured at a wavelength of 600 nm. The obtained suspension containing the bacterium was inoculated in 40 mL of the fermentation medium (described below) containing 20 mg/L of streptomycin contained in a 500-mL volume Erlenmeyer flask with baffles in such a volume that the turbidity measured at a wavelength of 600 nm became 0.2, and culture was performed at 37° C. for 48 hours at a rotation speed of 200 rpm for stirring by using a rotary shaking incubator, InnOva 4430 (New Brunswick Scientific).

As the carbon source for the main culture, sodium oleate was used. Tween 80 was added at a final concentration of 0.5% (v/v) as an emulsification enhancer. The total amount of the carbon source was 10 g/L. It was separately confirmed that Escherichia coli could not utilize Tween 80 by using the M9 minimal medium containing Tween 80.

The culture was performed for 48 hours under the aforementioned conditions, and amount of L-lysine accumulated in the medium was measured by using Biotech Analyzer AS310 (Sakura Seiki). Complete consumption of the oleate added to the medium was confirmed by using a gas chromatograph GC-2014 (Shimadzu). Furthermore, Tween 80 was added at a final concentration of 1.0% (v/v) immediately after the end of the culture, the resultant was appropriately diluted, and turbidity was measured at a wavelength of 600 nm to measure cell amount at the end of the culture.

Furthermore, hydrogen peroxide concentration in the cells contained in the medium was measured by the aforementioned method at the time of the end of the culture. The number of living bacterial cells in the medium was estimated on the basis of the common estimation that $10^9$ cells of Escherichia coli exist in 1 mL of a culture medium showing a turbidity of 1 determined at a wavelength of 600 nm.

The WC196LC/pCABD2,pTWV228 strain obtained by introducing pTWV228 into the WC196LC/pCABD2 strain was also cultured in the same manner as described above.

Composition of the fermentation medium used for the main culture containing oleate as the carbon source is shown below. The concentrations mentioned in the unit of g/L or % (in terms of volume/volume) are all final concentrations.

[Fermentation Medium Containing Oleate as Carbon Source]

| | |
|---|---|
| Sodium oleate (first grade, Junsei Chemical) | 10 g/L |
| Tween 80 | 0.5% |
| $MgSO_4 \cdot 7H_2O$ | 1 g/L |
| PIPES | 20 g/L |
| $(NH_4)_2SO_4$ | 16 g/L |
| $KH_2PO_4$ | 1 g/L |
| $FeSO_4 \cdot 7H_2O$ | 0.01 g/L |
| $MnSO_4 \cdot 7H_2O$ | 0.082 g/L |
| Yeast extract (Difco) | 2 g/L |

Sodium oleate was adjusted to pH 7.5 with HCl and autoclaved at 115° C. for 10 minutes.

Tween 80 was subjected to filter sterilization using Nalgene 0.45 μm filter (Nalgene).

$MgSO_4 \cdot 7H_2O$ was autoclaved at 115° C. for 10 minutes.

PIPES was adjusted to pH 7.5 with NaOH and autoclaved at 115° C. for 10 minutes.

The ingredients other than the above were mixed, adjusted to pH 7.5 with KOH, and autoclaved at 115° C. for 10 minutes.

As described above, the ingredients were divided into five groups, separately sterilized, and then mixed.

The results of the culture, i.e., L-lysine accumulation, yield based on oleate, cell turbidity (OD), and intracellular hydrogen peroxide concentration, are shown in Table 1. As seen from the results shown in Table 1, the WC196LC/pCABD2,pTWV228-oxyS strain showed significantly higher improvement in growth and L-lysine production compared with the WC196LC/pCABD2,pTWV228 strain, in which the oxyS gene expression was not enhanced. Moreover, the WC196LC/pCABD2,pTWV228-oxyS strain showed significantly lower intracellular hydrogen peroxide concentration as compared to the WC196LC/pCABD2,pTWV228 strain, in which the oxyS gene expression was not enhanced.

TABLE 1

| Strain | OD | Lys concentration (g/L) | Yield (%, w/w) | Intracellular hydrogen peroxide concentration (μM) |
|---|---|---|---|---|
| WC196LC/pCABD2, pTWV228 | 4.3 | 3.8 | 40.9 | 0.52 |
| WC196LC/pCABD2, pTWV228-oxyS | 6.2 | 4.2 | 45.3 | 0.26 |

Example 4

L-Lysine Production with fixABC Operon Expression-Enhanced Strain

Construction of fixABC Operon-Amplified Strain

PCR was performed using the primers shown in SEQ ID NOS: 5 and 6 and the chromosomal DNA of the W3110 strain as the template to obtain a PCR product containing the fixABC operon. The obtained PCR product was ligated with the pTWV228 vector (Takara Bio Inc.) digested with SalI by using In-Fusion™ Advantage PCR Cloning Kit (Clontech) to construct a plasmid pTWV-fixABC for amplification of the fixABC operon.

The WC196LC/pCABD2 strain was transformed with the plasmid pTWV-fixABC and the control vector pTWV228 in the same manner as that of Example 3 to obtain WC196LC/pCABD2/pTWV-fixABC and WC196 LC/pCABD2/pTWV228 strains, respectively.

Each of the aforementioned strains was cultured at 37° C. in the LB medium containing 50 mg/L of ampicillin and 20 mg/L of streptomycin until the final $OD_{600}$ became about 0.6, then a 40% glycerol solution was added to the culture medium in the same volume as that of the culture medium, and the mixture was stirred, divided into appropriate volumes, and stored at −80° C. as glycerol stock.

L-Lysine Production with fixABC Operon-Amplified Strain

Each of the glycerol stocks of the fixABC operon-amplified strain and the control strain was thawed, 100 µL of the thawed stock was uniformly applied to an LB plate containing 50 mg/L of ampicillin and 20 mg/L of streptomycin, and cultured at 37° C. for 24 hours. About ¼ of the obtained cells on the plate were suspended in 1.0 mL of physiological saline, and turbidity was measured at a wavelength of 600 nm. The obtained suspension containing the bacterium was inoculated into 40 mL of the fermentation medium described in Example 3 (provided that the concentration of $(NH_4)_2SO_4$ was changed to 24 g/L) containing 50 mg/L of ampicillin and 20 mg/L of streptomycin contained in a 500-mL volume Erlenmeyer flask with baffles in such a volume that the turbidity measured at a wavelength of 600 nm became 0.25, and culture was performed at 37° C. for 47 hours at a rotation speed of 200 rpm for stifling by using a rotary shaking incubator, InnOva 4430 (New Brunswick Scientific).

After 47 hours, the amount of L-lysine in the culture supernatant was measured using a Biotech Analyzer AS310 (Sakura SI). Complete consumption of the oleate added to the medium was separately confirmed by using a gas chromatograph GC-2014 (Shimadzu). Furthermore, Tween 80 was added at a final concentration of 1.0% (v/v) immediately after the end of the culture, the resultant was appropriately diluted, and turbidity was measured at a wavelength of 600 nm to measure cell amount at the time of the end of the culture. Furthermore, intracellular hydrogen peroxide concentration of the cells in the medium was measured by the aforementioned method at the time of the end of the culture.

The number of living bacterial cells in the medium was estimated on the basis of the common estimation that $10^9$ cells of *Escherichia coli* exist in 1 mL of a culture medium showing a turbidity of 1 determined at a wavelength of 600 nm.

L-Lysine accumulation, cell turbidity (OD), and intracellular hydrogen peroxide concentration are shown in Table 2. The fixABC operon-introduced strain showed significantly higher L-lysine production as compared to the control strain introduced with the vector pTWV228. Furthermore, the fixABC operon-introduced strain showed significantly lower intracellular hydrogen peroxide concentration as compared to the control strain introduced with the vector pTWV228.

TABLE 2

| Strain | OD | L-lysine (g/L) | Intracellular hydrogen peroxide concentration (µM) |
|---|---|---|---|
| WC196LC/pCABD2/pTWV228 | 3.8 | 3.5 | 0.52 |
| WC196LC/pCABD2/pTWV-fixABC | 7.4 | 4.3 | 0.34 |

Example 5

L-Lysine Production with fixABC Expression-Enhanced Strain of Ethanol-Utilizing Bacterium Impartation of Ethanol-Utilizing Ability to WC196LC Strain In order to impart ethanol-utilizing ability to the L-lysine-producing bacterium, a mutant alcohol dehydrogenase gene (adhE*) was introduced. As the mutant alcohol dehydrogenase gene, the gene derived from the MG1655::PL-tacadhE* strain (refer to WO2008/010565) was used. The MG1655:PL-tacadhE* strain is a strain obtained by inserting a DNA fragment having the chloramphenicol resistance gene (cat) and a mutant adhE gene controlled by the PL-tac promoter into the genome of the *Escherichia coli* MG1655 strain. The mutant adhE gene codes for a mutant protein in which the glutamic acid residue at position 568 is replaced with a lysine residue. *Escherichia coli* containing this alcohol dehydrogenase can utilize ethanol under aerobic conditions.

In order to make it possible to remove the cat gene from the genome of the MG1655::PL-tacadhE* strain, the cat gene was replaced with a DNA fragment obtained by ligating the attachment site of λ phage and the tetracycline resistance gene (att-tet).

For the replacement of the cat gene with the att-tet gene, the λ-red method (Datsenko, K. A. and Wanner, B. L., 2000, Proc. Natl. Acad. Sci. USA, 97:6640-6645) was used. As the primers for the replacement of the cat gene with the att-tet gene, the synthetic oligonucleotides of SEQ ID NOS: 7 and 8 were used. In this way, MG1655-att-tet-PL-tacadhE* strain, which is a strain of the MG1655::PL-tacadhE* strain in which the cat gene is replaced with the att-tet gene, was obtained.

In order to impart ethanol-utilizing ability to the L-lysine-producing bacterium, P1 lysate was obtained from the MG1655-att-tet-PL-tacadhE* strain in a conventional manner, and the L-lysine-producing bacterium WC196LC strain was used as a host to obtain WC196LC-att-tet-PL-tacadhE* strain by using the P1 transduction method.

Then, in order to remove the att-tet gene introduced upstream of the PL-tac promoter, a helper plasmid pMW-intxis-ts (U.S. Patent Application Pub. No. 2006/0141586) was used. pMW-intxis-ts is a plasmid carrying a gene coding for λ phage integrase (Int) and a gene coding for λ phage excisionase (Xis), and having temperature sensitive replication ability.

Competent cells of the WC196LC-att-tet-PL-tacadhE* strain obtained as described above were prepared in a conventional manner, transformed with the helper plasmid pMW-intxis-ts, and cultured at 30° C. on a plate of the LB agar medium containing 50 mg/L of ampicillin to select an ampicillin-resistant strain. Then, to remove the pMW-intxists plasmid, the transformant was cultured at 42° C. on the LB agar medium, and ampicillin resistance and tetracycline resistance of the obtained colonies were examined to obtain an ampicillin and tetracycline-sensitive strain, which was a PL-tacadhE*-introduced strain not containing att-tet and pMW-intxis-ts. This strain was designated as WC196LC PL-tacadhE* strain.

Introduction of plasmid for enhancing fixABC expression, pTWV228-fixABC, and plasmid for L-lysine production (pCABD2) into WC196LC PL-tacadhE* strain By introducing pCABD2 into the L-lysine-producing bacterium, WC196LC PL-tacadhE* strain, WC196LC PL-tacadhE*/pCABD2 strain was constructed. pTWV228-fixABC and pTWV228 were introduced into this strain to obtain WC196LC PL-tacadhE*/pCABD2,pTWV228-fixABC strain and WC196LC PL-tacadhE*/pCABD2,pTWV228 strain, respectively. Glycerol stocks of these strains were prepared.

Evaluation of L-Lysine-Producing Ability of fixABC Expression-Enhanced Strain from Ethanol The glycerol stocks of the aforementioned strains were thawed, 100 µL of each of the thawed stocks was uniformly applied to an L-plate containing 20 mg/L of streptomycin, and culture was performed at 37° C. for 15 hours. The obtained cells were suspended in a 0.85% NaCl aqueous solution, inoculated into 5 mL of a fermentation medium containing 20 mg/L of streptomycin and 50 mg/L of ampicillin contained in a large size test tube (internal diameter: 18 mm) at an initial $OD_{600}$ of 0.25, and cultured at 37° with stirring at 120 rpm by using a reciprocal incubator.

Composition of the fermentation medium containing ethanol as the carbon source is shown below.

[Composition of Fermentation Medium Containing Ethanol as Carbon Source]

| | |
|---|---|
| Ethanol | 10 ml/L |
| $(NH_4)_2SO_4$ | 24 g/L |
| $K_2HPO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 5H_2O$ | 0.082 g/L |
| Yeast extract | 2.0 g/L |
| $CaCO_3$ (Japanese Pharmacopoeia) | 30 g/L |
| Distilled water for the final volume of 1 L | |

$(NH_4)_2SO_4$, $K_2HPO_4$, $FeSO_4.7H_2O$, $MnSO_4.7H_2O$, and yeast extract were mixed, adjusted to pH 5.7 with KOH, and autoclaved at 115° C. for 10 minutes. $MgSO_4.7H_2O$ was separately sterilized, and ethanol was sterilized by filter filtration. $CaCO_3$ was subjected to dry sterilization at 180° C. for 2 hours and added to the medium. After culturing for 16 hours, 20 µL of ethanol was added. After culturing for 21 hours, the amount of L-lysine that accumulated in the medium was measured using a Biotech Analyzer AS210 (Sakura Seiki), and the ethanol concentration in the culture medium was measured using a biosensor (Oji Scientific Instruments Biosensor BF-5). The fixABC expression-enhanced strain (WC196LC PL-tacadhE*/pCABD2, pTWV228-fixABC strain) showed significantly higher growth and L-lysine production as compared to the control strain (WC196LC PL-tacadhE*/pCABD2,pTWV228 strain).

TABLE 3

| Strain | OD | Lys concentration (g/L) | Yield (%, w/w) |
|---|---|---|---|
| WC196LC PL-tacadhE*/pCABD2, pTWV228 | 4.7 | 5.5 | 47.1 |
| WC196LC PL-tacadhE*/pCABD2, pTWV228-fixABC | 5.6 | 6.1 | 49.1 |

Example 6

Evaluation of L-Lysine-Producing Ability of L-Lysine-Producing Bacterium from Fatty Acid as Carbon Source with Addition of Anti-Oxidant Thiourea to Medium Preculture The glycerol stock of the L-lysine-producing bacterium, WC196 LC/pCABD2 strain, was inoculated in an amount of one loop to the LB agar medium (1% of tryptone, 0.5% of yeast extract, 0.5% of sodium chloride, 1.5% of agarose) containing 20 mg/L of streptomycin, and cultured at 37° C. for 24 hours as static culture.

Main Culture Using Small Fermentation Tank Having Total Volume of 1 L

The cells grown in the aforementioned preculture were scraped off from the medium, suspended in a 0.85% NaCl aqueous solution, and inoculated into 300 mL of MS glucose liquid fermentation medium or MS fatty acid liquid fermentation medium having the following compositions and contained in a small fermentation tank having a total volume of 1 L at a turbidity of 0.04 measured at a wavelength of 600 nm to start the culture. With the MS glucose liquid fermentation medium, the culture was performed at a culture temperature of 37° C. and a stirring rate of 300 rpm for 16 hours with the addition of 20 mg/L of streptomycin and aeration of compressed air sterilized with a sterilization filter at 1 vvm. Furthermore, pH was maintained at 6.7 with ammonia gas. With the MS fatty acid liquid fermentation medium, the culture was performed at a culture temperature of 37° C. and a stirring rate of 700 rpm for 42 hours with addition of 20 mg/L of streptomycin and aeration of compressed air sterilized with a sterilization filter at 1 vvm. Furthermore, pH was maintained at 6.7 with ammonia gas.

The culture was performed with adding 1 mM or 5 mM thiourea as an antioxidant at the time of the start of the culture. As controls, the culture was performed under a condition in which thiourea was not added (referred to as a thiourea-free condition), and a condition in which urea was added at the same concentrations as thiourea (referred to as a urea addition condition).

During the culture, an appropriate volume of each liquid medium was sampled, and the amount of L-lysine in the culture supernatant was measured with a Biotech Analyzer AS310 (Sakura SI). Complete consumption of the oleate added to the medium was confirmed by using a gas chromatograph GC-2014 (Shimadzu). Complete consumption of the glucose added to the medium was separately confirmed by using a Biotech Analyzer AS310. Furthermore, a Tween 80 solution was added at a final concentration of 1.0% (v/v) immediately after the end of the culture, the resultant was appropriately diluted, and turbidity was measured at a wavelength of 600 nm to measure cell amount at the time of the end of the culture.

Furthermore, intracellular hydrogen peroxide concentration of the cells in the medium was measured by the aforementioned method at the end of the culture. The number of living bacterial cells in the medium was estimated on the basis of the common estimation that $10^9$ cells of Escherichia coli exist in 1 mL of a culture medium showing a turbidity of 1 determined at a wavelength of 600 nm.

[MS Glucose Liquid Fermentation Medium]

| | |
|---|---|
| Glucose | 10 g/L |
| Tween 80 | 0.5% |
| $MgSO_4 \cdot 7H_2O$ | 1 g/L |
| $(NH_4)_2SO_4$ | 24 g/L |
| $KH_2PO_4$ | 1 g/L |
| $FeSO_4 \cdot 7H_2O$ | 0.01 g/L |
| $MnSO_4 \cdot 7H_2O$ | 0.082 g/L |
| Yeast extract (Difco) | 2 g/L |

[MS Fatty Acid Liquid Fermentation Medium]

| | |
|---|---|
| Sodium oleate (first grade, Junsei Chemical) | 10 g/L |
| Tween 80 | 0.5% |
| $MgSO_4 \cdot 7H_2O$ | 1 g/L |
| $(NH_4)_2SO_4$ | 24 g/L |
| $KH_2PO_4$ | 1 g/L |
| $FeSO_4 \cdot 7H_2O$ | 0.01 g/L |
| $MnSO_4 \cdot 7H_2O$ | 0.082 g/L |
| Yeast extract (Difco) | 2 g/L |

Figure 8:
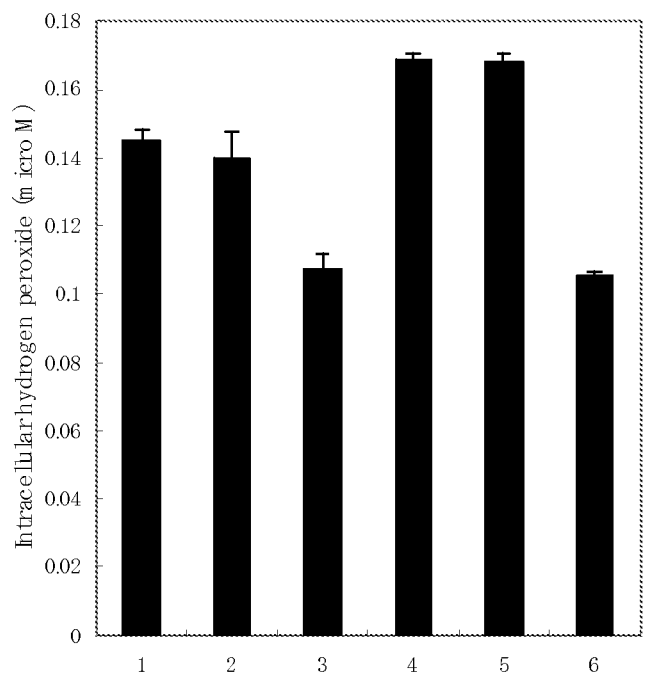
FIG. 8 shows intracellular hydrogen peroxide concentration observed in L-lysine production culture using glucose or a fatty acid as a carbon source and using the addition of thiourea or urea.
 1. Carbon source, glucose; additive-free
 2. Carbon source, glucose; addition of 1 mM urea
 3. Carbon source, glucose, addition of 1 mM thiourea
 4. Carbon source, oleic acid, additive-free
 5. Carbon source, oleic acid, addition of 1 mM urea
 6. Carbon source, oleic acid, addition of 1 mM thiourea

L-Lysine accumulation, and cell turbidity (OD) at the time of the end of culture, as well as the culture time required for consumption of all the carbon source in the culture medium, observed with the various culture conditions, are shown in Tables 4, 5, and 6, and the results of the hydrogen peroxide concentration measurement are shown in FIG. 8. In the L-lysine production culture using the fatty acid as the carbon source, the thiourea addition condition provided significantly higher L-lysine production and cell turbidity as compared to the control conditions (thiourea-free condition and urea addition condition). Furthermore, in the L-lysine production culture using the fatty acid as the carbon source, the fatty acid added to the medium was consumed within a significantly shorter time under the thiourea addition condition compared with the control conditions (thiourea-free condition and urea addition condition). Furthermore, in the L-lysine production culture using glucose as the carbon source and the L-lysine production culture using fatty acid as the carbon source, the thiourea addition condition provided a significantly lower intracellular hydrogen peroxide concentration as compared to the control conditions (thiourea-free condition and urea addition condition).

TABLE 4

OD600 at the end of culture

| | Carbon source | |
|---|---|---|
| Culture condition | Fatty acid | Glucose |
| Thiourea free | 6.6 | 5.3 |
| Thiourea free | 6.9 | 5.2 |
| 1 mM Thiourea | 7.3 | 5.3 |
| 5 mM Thiourea | 7.5 | 5.2 |
| 1 mM Urea | 6.8 | 5.2 |
| 5 mM Urea | 6.9 | 5.2 |

TABLE 5

L-Lysine accumulation (g/L) at the end of culture

| | Carbon source | |
|---|---|---|
| Culture condition | Fatty acid | Glucose |
| Thiourea free | 4.8 | 4.7 |
| Thiourea free | 4.8 | 4.7 |
| 1 mM Thiourea | 5.2 | 4.7 |
| 5 mM Thiourea | 5.2 | 4.7 |
| 1 mM Urea | 4.8 | 4.6 |
| 5 mM Urea | 4.8 | 4.6 |

TABLE 6

Culture time (hr) required for consumption of carbon source

| | Carbon source | |
|---|---|---|
| Culture condition | Fatty acid | Glucose |
| Thiourea free | 41.5 | 16.0 |
| Thiourea free | 41.5 | 16.0 |
| 1 mM Thiourea | 33.0 | 16.0 |
| 5 mM Thiourea | 33.0 | 16.0 |
| 1 mM Urea | 41.5 | 16.0 |
| 5 mM Urea | 41.5 | 16.0 |

Explanation of Sequence Listings

SEQ ID NO: 1: Primer for oxyS gene amplification
SEQ ID NO: 2: Primer for oxyS gene amplification
SEQ ID NO: 3: Primer for sodA gene amplification
SEQ ID NO: 4: Primer for sodA gene amplification
SEQ ID NO: 5: Primer for fixABC operon amplification
SEQ ID NO: 6: Primer for fixABC operon amplification
SEQ ID NO: 7: Primer for substitution of att-tet gene for cat gene
SEQ ID NO: 8: Primer for substitution of att-tet gene for cat gene
SEQ ID NO: 9: Nucleotide sequence of oxyS gene
SEQ ID NO: 10: Nucleotide sequence of fixA gene
SEQ ID NO: 11: Amino acid sequence encoded by fixA gene
SEQ ID NO: 12: Nucleotide sequence of fixB gene
SEQ ID NO: 13: Amino acid sequence encoded by fixB gene
SEQ ID NO: 14: Nucleotide sequence of fixC gene
SEQ ID NO: 15: Amino acid sequence encoded by fixC gene
SEQ ID NO: 16: Nucleotide sequence of sodA gene
SEQ ID NO: 17: Amino acid sequence encoded by sodA gene

INDUSTRIAL APPLICABILITY

As described herein, an L-amino acid can be efficiently produced by fermentation using a fatty acid or an alcohol as a carbon source.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing an L-amino acid, the method comprising:
   A) culturing a bacterium which belongs to the family Enterobacteriaceae and has an L-amino acid-producing ability, in a medium containing a carbon source selected from the group consisting of a fatty acid and an alcohol;
   B) reducing intracellular hydrogen peroxide concentration of the bacterium; and
   C) collecting the L-amino acid from the medium,
wherein said reducing is accomplished by modifying the bacterium by increasing the copy number of a fixABC gene, and/or replacing a promoter of a fixABC gene with a stronger promoter.

2. The method according to claim 1, wherein the bacterium belongs to the genus *Escherichia, Pantoea,* or *Enterobacter*.

3. The method according to claim 2, wherein the bacterium is *Escherichia coli, Pantoea ananatis,* or *Enterobacter aerogenes*.

4. The method according to claim 1, wherein fixABC encodes proteins comprising the amino acid sequences of SEQ ID NOS: 11, 13, and 15, or conservative variants of these sequences, wherein said conservative variants have the amino acid sequences of SEQ ID NOS: 11, 13, and 15 but include 1 to 5 amino acid substitutions, deletions, or insertions, and wherein the conservative variants have a function for reducing intracellular hydrogen peroxide concentration of the bacterium.

5. The method according to claim 1, wherein the carbon source is a fatty acid.

6. The method according to claim 5, wherein the fatty acid is oleic acid.

7. The method according to claim 5, wherein the fatty acid is a mixture of fatty acids derived from a fat or oil.

8. The method according to claim 1, wherein the carbon source is an alcohol.

9. The method according to claim 8, wherein the alcohol is glycerol.

10. The method according to claim 8, wherein the alcohol is ethanol.

11. The method according to claim 1, wherein the carbon source is a mixture of a fatty acid and glycerol obtained by hydrolyzing a fat or oil.

12. The method according to claim 10, wherein the bacterium is *Escherichia coli* which has been modified to be able to aerobically utilize ethanol.

13. The method according to claim 1, wherein the L-amino acid is L-lysine.

14. The method according to claim 13, further comprising:
   A) enhancing an activity of at least one enzyme selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyldiaminopimelate deacylase, wherein the activity of the enzyme is enhanced by increasing the copy number of a gene coding the enzyme, and/or replacing a promoter of a gene coding the enzyme with a stronger promoter; or
   B) disrupting lysine decarboxylase; or
   C) both.

* * * * *